(12) United States Patent
Marban et al.

(10) Patent No.: US 11,541,078 B2
(45) Date of Patent: Jan. 3, 2023

(54) CARDIOSPHERE-DERIVED CELLS AND THEIR EXTRACELLULAR VESICLES TO RETARD OR REVERSE AGING AND AGE-RELATED DISORDERS

(71) Applicant: Cedars-Sinai Medical Center, Los Angeles, CA (US)

(72) Inventors: Eduardo Marban, Santa Monica, CA (US); Lilian Grigorian, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 479 days.

(21) Appl. No.: 16/333,581

(22) PCT Filed: Sep. 19, 2017

(86) PCT No.: PCT/US2017/052350
§ 371 (c)(1),
(2) Date: Mar. 14, 2019

(87) PCT Pub. No.: WO2018/057542
PCT Pub. Date: Mar. 29, 2018

(65) Prior Publication Data
US 2019/0255119 A1  Aug. 22, 2019

Related U.S. Application Data

(60) Provisional application No. 62/397,061, filed on Sep. 20, 2016.

(51) Int. Cl.
| | | |
|---|---|---|
| *A61K 35/34* | (2015.01) | |
| *A61P 25/28* | (2006.01) | |
| *A61P 9/00* | (2006.01) | |
| *A61P 17/14* | (2006.01) | |
| *A61P 19/02* | (2006.01) | |
| *A61K 9/00* | (2006.01) | |
| *A61K 9/127* | (2006.01) | |
| *A61Q 19/08* | (2006.01) | |
| *C12N 9/12* | (2006.01) | |
| *C12N 9/38* | (2006.01) | |
| *C12N 5/077* | (2010.01) | |
| *A61P 9/04* | (2006.01) | |
| *A61P 39/00* | (2006.01) | |
| *A61K 39/00* | (2006.01) | |

(52) U.S. Cl.
CPC ............ *A61K 35/34* (2013.01); *A61K 9/0019* (2013.01); *A61K 9/127* (2013.01); *A61P 9/00* (2018.01); *A61P 9/04* (2018.01); *A61P 17/14* (2018.01); *A61P 19/02* (2018.01); *A61P 25/28* (2018.01); *A61P 39/00* (2018.01); *A61Q 19/08* (2013.01); *C12N 5/0657* (2013.01); *C12N 9/1276* (2013.01); *C12N 9/2471* (2013.01); *A61K 2039/55555* (2013.01); *C12Y 207/07049* (2013.01); *C12Y 302/01023* (2013.01)

(58) Field of Classification Search
None
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |

(Continued)

FOREIGN PATENT DOCUMENTS

| | | |
|---|---|---|
| CA | 2488346 | 12/2003 |
| CN | 1537646 | 10/2004 |

(Continued)

OTHER PUBLICATIONS

Carr et al., "Cardiosphere-derived cells improve function in the infarcted rat heart for at least 16 weeks—an MRI study", PLoS ONE 6(10): e25669. doi: 10.13171/journal.pone.0025669 (Year: 2011).*

(Continued)

*Primary Examiner* — Anand U Desai
(74) *Attorney, Agent, or Firm* — Knobbe, Martens, Olson & Bear, LLP

(57) ABSTRACT

Described herein are compositions and methods related to use of cardiosphere-derived cells and their extracellular vesicles, such as exosomes and microvesicles, for achieving anti-aging and rejuvenation. This includes discoveries for effects on heart structure, function, gene expression, and systemic parameters. For animal studies, intra-cardiac injections of neonatal rat CDCs was compared to in old and young rats including evaluation of blood, echocardiographic, haemodynamic and treadmill stress tests. For in vitro studies, human heart progenitors from older donors, or cardiomyocytes from aged rats were exposed to human CDCs or cardiosphere derived cell (CDC) derived exosomes (CDC-XO) from pediatric donors. CDCs and CDC-XOs were capable of effectuating youthful patterns of gene expression in the hearts of old, along with a variant of physiological and function benefits, including elongation of telomere length. Together, these results indicate capacity of CDCs and CDC-XO to ward off the effects of aging through rejuvenation.

16 Claims, 51 Drawing Sheets

(56) References Cited

U.S. PATENT DOCUMENTS

| | | |
|---|---|---|
| 5,028,588 A | 7/1991 | Hoffman et al. |
| 5,052,402 A | 10/1991 | Bencini et al. |
| 5,104,787 A | 4/1992 | Lindstrom et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |

(56) References Cited

U.S. PATENT DOCUMENTS

| | | |
|---|---|---|
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1* | 7/2004 | Schneider ............ C12N 5/0657 435/372 |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0189780 A1 | 7/2013 | Shoemaker et al. |
| 2013/0266543 A1 | 10/2013 | Nadal-Ginard |
| 2013/0280205 A1 | 10/2013 | Mozaffari et al. |
| 2013/0288962 A1 | 10/2013 | Anversa et al. |

(56) References Cited

U.S. PATENT DOCUMENTS

| | | |
|---|---|---|
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhaegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0140658 A1 | 5/2015 | Kamp et al. |
| 2015/0246030 A1 | 9/2015 | Armer et al. |
| 2015/0273113 A1 | 10/2015 | Marbán et al. |
| 2015/0328263 A1* | 11/2015 | Kaushal ............ A61K 38/1891 424/93.7 |
| 2016/0158291 A1 | 6/2016 | Kreke et al. |
| 2016/0244723 A1 | 8/2016 | Giacomello et al. |
| 2017/0037375 A1 | 2/2017 | Palecek et al. |
| 2017/0049793 A1 | 2/2017 | Moon et al. |
| 2017/0087087 A1 | 3/2017 | Leonard et al. |
| 2017/0290860 A1 | 10/2017 | Marbán et al. |
| 2017/0304368 A1 | 10/2017 | Marbán et al. |
| 2018/0100149 A1 | 4/2018 | Marbán et al. |
| 2019/0000888 A1 | 1/2019 | Marbán et al. |
| 2019/0062740 A1 | 2/2019 | Zhu |
| 2019/0160111 A1 | 5/2019 | Marbán et al. |
| 2020/0024604 A1 | 1/2020 | Marbán et al. |
| 2020/0121727 A1 | 4/2020 | Marbán et al. |
| 2020/0316226 A1 | 10/2020 | Marbán et al. |
| 2021/0032598 A1 | 2/2021 | Ibrahim et al. |
| 2021/0085724 A1 | 3/2021 | Marbán et al. |
| 2021/0207145 A1 | 7/2021 | Marbán et al. |

FOREIGN PATENT DOCUMENTS

| | | |
|---|---|---|
| CN | 1772300 | 5/2006 |
| CN | 1785430 | 6/2006 |
| EP | 1 254 952 | 11/2002 |
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |
| EP | 1 650 293 | 12/2010 |
| EP | 2 371 370 | 10/2011 |
| EP | 2 385 120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 687 219 | 1/2014 |
| JP | 2005-506845 | 3/2005 |
| JP | 2005-110565 | 4/2005 |
| JP | 2006-006125 | 1/2006 |
| JP | 2008-504816 | 2/2008 |
| JP | 2008-518730 | 6/2008 |
| KR | 100830889 | 5/2008 |
| KR | 10-1818560 | 1/2018 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 01/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |
| WO | WO 2014/013258 | 1/2014 |
| WO | WO 2014/028493 | 2/2014 |
| WO | WO 2014/114465 | 7/2014 |
| WO | WO 2014/160153 | 10/2014 |
| WO | WO 2015/055857 | 4/2015 |
| WO | WO 2015/085096 | 6/2015 |

(56) References Cited

FOREIGN PATENT DOCUMENTS

| | | |
|---|---|---|
| WO | WO 2015/092020 | 6/2015 |
| WO | WO 2015/120150 | 8/2015 |
| WO | WO 2016/054591 | 4/2016 |
| WO | WO 2016/057560 | 4/2016 |
| WO | WO 2017/160884 | 9/2017 |
| WO | WO 2017/173034 | 10/2017 |
| WO | WO 2019/015702 | 1/2019 |
| WO | WO 2019/028223 | 2/2019 |
| WO | WO 2019/050071 | 3/2019 |
| WO | WO 2019/126068 | 6/2019 |
| WO | WO 2019/152549 | 8/2019 |
| WO | WO 2020/227489 | 11/2020 |
| WO | WO 2021/178514 | 9/2021 |
| WO | WO 2021/188899 | 9/2021 |

OTHER PUBLICATIONS

Kasai-Brunswick et al., "Cardiosphere-derived cells do not improve cardiac function in rats with cardiac failure", Stem Cell Research & Therapy 8:36 (9 pages) DOI 10.1186/s13287-017-0481-x (Year: 2017).*

Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, vol. 23, No. 17 & 18, 2017, pp. 989-1000.

Magarotto et al., "Muscle Functional Recovery is Driven by Extracellular Vesicles Combined with Muscle Extracellular Matrix in a Volumetric Muscle Loss Murine Model", Biomaterials 269, 2021, pp. 1-15.

Pilia et al., "Transplantation and Perfusion of Microvascular Fragments in a Rodent Model of Volumetric Muscle Loss Injury", European Cells and Materials, vol. 28, 2014, pp. 11-24.

Sicari et al., "An Acellular Biologic Scaffold Promotes Skeletal Muscle Formation in Mice and Humans with Volumetric Muscle Loss", Science Translational Medicine, Apr. 30, 2014, vol. 6, No. 234, pp. 1-10.

Agrahari et al., "How Are We Improving the Delivery to Back of the Eye? Advances and Challenges of Novel Therapeutic Approaches", Expert Opinion on Drug Delivery, 2017, vol. 14, No. 10, pp. 1145-1162.

Aminzadeh et al., "Exosome-Mediated Benefits of Cell Therapy in Mouse and Human Models of Duchenne Muscular Dystrophy", Stem Cell Reports, Mar. 13, 2018, vol. 10, No. 3, pp. 942-955.

Aminzadeh et al., "Mitigation of Skeletal Myopathy After Intramyocardial Injection of Cardiosphere-derived Cells in the Mdx Mouse Model of Duchenne Muscular Dystrophy", Circulation Research, Dec. 4, 2015, No. 22919, pp. e122-e127.

Bryan et al., "Implications of Protein Fold Switching", Current Comments, posted Feb. 4, 2013, printed in 4 pages. web.archive.org/web/20160628060217/www.elsevierblogs.com/currentcomments/?p=962.

Cheng et al., "Focus on Mesenchymal Stem Cell-Derived Exosomes: Opportunities and Challenges in Cell-Free Therapy", Hindawi, Stem Cells International, 2017, Article ID 6305295, pp. 10.

Cooper et al., "Immunobiological Barriers to Xenotransplantation", International Journal of Surgery, 2015, vol. 23, pp. 211-216.

Dib et al., "Cell Therapy for Cardiovascular Disease: A Comparison of Methods of Delivery", Journal of Cardiovascular Translational Research, 2011, vol. 4, pp. 177-181.

Edelberg et al., "Platelet-Derived Growth Factor-AB Limits the Extent of Myocardial Infarction in a Rat Model: Feasibility of Restoring Impaired Angiogenic Capacity in the Aging Heart", Circulation, 2002, vol. 150, No. 5, pp. 608-613.

Fernandez-Aviles et al., "Experimental and Clinical Regenerative Capability of Human Bone Marrow Cells After Myocardial Infarction", Circulation Research, 2004, vol. 95, pp. 742-748.

Gallet et al, "Cardiosphere-Derived Cells Reverse Heart Failure with Preserved Ejection Fraction in Rats by Decreasing Fibrosis and Inflammation", JACC: Basic to Translational Science, Jan. 1, 2016, vol. 1, No. 1-2, pp. 14-28.

Gallet et al, "Exosomes Secreted by Cardiosphere-Derived Cells Reduce Scarring, Attenuate Adverse Remodeling, and Improve Function in Acute and Chronic Porcine Myocardial Infarction", European Heart Journal, Jan. 14, 2017, vol. 38, pp. 201-211.

Haderk et al., "Tumor-Derived Exosomes Modulate PD-L1 Expression in Monocytes", Science Immunology, Jul. 28, 2017, vol. 2, No. 13, pp. 1-11.

Heng et al., "Strategies for Directing the Differentiation of Stem Cells into the Cardiomyogenic Lineage in Vitro", Cardiovascular Research, 2004, vol. 62, pp. 34-42.

Hoppe et al., "Distinct Gene-Specific Mechanisms of Arrhythmia Revealed by Cardiac Gene Transfer of Two Long QT Disease Genes, HERG and KCNE1", Proceedings of the National Academy of Sciences of the United States of America, Apr. 24, 2001, vol. 98, No. 9, pp. 5335-5340.

Ikehara et al., "Grand Challenges in Stem Cell Treatments", Frontiers in Cell and Developmental Biology, Oct. 10, 2013, vol. 1, No. 2, pp. 2.

Kobashigawa et al., "A Randomized Active-Controlled Trial of Mycophenolate Mofetil in Heart Transplant Recipients", Transplantation, Aug. 27, 1998, vol. 66, No. 4, pp. 507-515.

Li et al., "IL-6 Contributes to the Defective Osteogenesis of Bone Marrow Stromal Cells from the Vertebral Body of the Glucocorticoid-Induced Osteoporotic Mouse", PLoS ONE, Apr. 29, 2016, vol. 11, No. 4, pp. 19.

Limana et al., "Exogenous High-Mobility Group Box 1 Protein Induces Myocardial Regeneration after Infarction via Enhanced Cardiac C-Kit+ Cell Proliferation and Differentiation", Circulation Research, Oct. 14, 2005, vol. 97, No. 8, pp. 73-83.

Liu et al., "The Immunogenicity and Immune Tolerance of Pluripotent Stem Cell Derivatives", Frontiers in Immunology, Jun. 2017, vol. 3, No. 645, pp. 1-6.

Makkar et al., "Intracoronary Cardiosphere-Derived Cells for Heart Regeneration After Myocardial Infarction (Caduceus): A Prospective, Randomised Phase 1 Trial", Lancet, Mar. 10, 2012, vol. 379, pp. 895-904.

Malliaras et al., "Intracoronary Cardiosphere-Derived Cells After Myocardial Infarction", Journal of the American College of Cardiology, 2014, vol. 63, No. 2, pp. 110-121.

Maqbool et al., The Substrate-Binding Protein in Bacterial ABC Transporters: Dissecting Roles in the Evolution of Substrate Specificity, Biochemical Society Transactions, 2015, vol. 43, Part 5, pp. 1011-1017.

Matsumura, Tsuyoshi, "Cardiaphal Association in Muscular Dystrophy", Nanbyo To Zaitaku Care (Intractable Diseases and Home Care), 2013, vol. 19, No. 8, pp. 55-57.

Menascheé et al., "Autologous Skeletal Myoblast Transplantation for Severe Postinfarction Left Ventricular Dysfunction", Journal of the American College of Cardiology, vol. 41, No. 7, Apr. 2, 2003, pp. 1078-1083.

Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.

North et al., "The Intersection Between Aging and Cardiovascular Disease", Circulation Research, Apr. 13, 2012, pp. 1097-1108.

Pfeffer et al., "Myocardial Infarct Size and Ventricular Function in Rats", Circulation Research, Apr. 1979, vol. 44, No. 4, pp. 503-512.

Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.

Schächinger et al., "Transplantation of Progenitor Cells and Regeneration Enhancement in Acute Myocardial Infarction: Final One-Year Results of the TOPCARE-AMI Trial", Journal of the American College of Cardiology, Oct. 19, 2004, vol. 44, No. 8, pp. 1690-1699.

Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.

Shimasaki et al., "Exosome Research and Co-culture Study", Biological and Pharmaceutical Bulletin, vol. 40, No. 9, 2018, pp. 1311-1321.

(56) References Cited

OTHER PUBLICATIONS

Siminiak et al., "Autologous Skeletal Myoblast Trans plantation for the Treatment of Postinfarction Myocardial Injury: Phase I Clinical Study with 12 Months of Follow-Up", American Heart Journal, Sep. 2004, vol. 148, No. 3, pp. 531-537.
Smits et al., "Catheter-Based Intramyocardial Injection of Autologous Skeletal Myoblasts as a Primary Treatment of Ischemic Heart Failure: Clinical Experience with Six-Month Follow-Up", Journal of the American College of Cardiology, 2003, vol. 42, No. 12, pp. 2063-2069.
Strauer et al., "Repair of infarcted Myocardium by Autologous Intracoronary Mononuclear Bone Marrow Cell Transplantation in Humans", Circulation, Oct. 8, 2002, vol. 106, No. 15, pp. 1913-1918.
Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.
Takeda et al., "Induced Pluripotant Stem (IPS) Cell-Based Cell Therapy for Duchenne Muscular Dystrophy", History of Medicine, Dec. 31, 2011, vol. 239, No. 14, pp. 1440-1444.
Taylor et al., "A Randomized, Multicenter Comparison of Tacrolimus and Cyclosporine Immunosuppressive Regimens in Cardiac Transplantation: Decreased Hyperlipidemia and Hypertension with Tacrolimus", Journal Heart Lung Transplant, Apr. 1, 1999, vol. 18, No. 4, pp. 336-345.
Tsutsui, Hiroyuki, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, Feb. 2014, vol. 103, No. 2, pp. 277-284.
Bioptome.com, Scholten Surgical Instruments, Inc., downloaded from http://www.bioptome.com, 2001, first date of publication unknown, printed on Nov. 1, 2005, pp. 2.
Wu et al., "Cell Delivery in Cardiac Regenerative Therapy", Ageing Research Reviews, 2012, vol. 11, pp. 32-40.
Zeger et al., "Longitudinal Data Analysis for Discrete and Continuous Outcomes", Biometrics, Mar. 1986, vol. 42, No. 1, pp. 121-130.
Anastasiou-Nana et al., "Relative Efficiency and Risk of Endomyocardial Biopsy: Comparisons in Heart Transplant and Nontransplant Patients," Catheter Cardiovascular Diagnosis Journal, Sep. 1989, vol. 18, No. 1, pp. 7-11.
Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.
Catalano, Mariadelva, "Engineering Exosomes Toward Folate Receptor Expressing Cells", Dec. 7, 2017, pp. 3.
Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.
De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).
Girard et al., "A Germline-Specific Class of Small RNAs Binds Mammalian Piwi Proteins", Nature, Jul. 13, 2006, vol. 442, pp. 199-202.
Ibrahim et al., "Augmenting Canonical Wnt Signaling in Therapeutically Inert Cells Converts them into Therapeutically Potent Exosome Factories", Nature Biomedical Engineering, Sep. 2019, vol. 3, pp. 695-705.
Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, pp. 7.
Kim, PhD et al., "Engineering Macrophage-Derived Exosomes for Targeted Paclitaxel Delivery to Pulmonary Metastases:in Vitroandin Vivoevaluations", Nanomedicine, Nanotechnology, Biology, and Medicine, vol. 14, 2018, pp. 195-204.
Kim, PhD et al., "Exosome Mediated Delivery of Paclitaxel for the Treatment of Multi Drug Resistant Pulmonary Metastases", Dissertation, Chapel Hill, Dec. 31, 2016, pp. 112.
Mason, "Techniques for Right and Left Ventricular Endomyocardial Biopsy", American Journal of Cardiology, 1978, vol. 41, No. 5, pp. 887-892.
Shen et al., "The Early Cryptic Transmission and Evolution of SARS-CoV-2 in Human Hosts", Available at SSRN 3724275, Aug. 2019, www.oyeyeah.com/wp-content/uploads/2020/11/SSRN-is3724275.pdf, pp. 22.
Smyth et al., "Surface Functionalization of Exosomes Using Click Chemistry", Bioconjugate Chemistry, vol. 25, No. 10, Sep. 30, 2014, pp. 1777-1784.
USPTO Patent Trial and Appeal Board., "Decision on Appeal", in U.S. Appl. No. 13/412,051, dated Jun. 8, 2020, 12 pages.
USPTO Patent Trial and Appeal Board., "Declaration of Rachel R. Smith, PhD," in U.S. Appl. No. 13/412,051, dated Oct. 13, 2017, 32 pages.
Vella et al., "PIWI-Interacting RNA (piRNA) Signatures in Human Cardiac Progenitor Cells", The International Journal of Biochemistry & Cell Biology, 2016, vol. 76, pp. 1-11.
Wan et al., "Aptamer-Conjugated Extracellular Nanovesicles for Targeted Drug Delivery", Cancer Research, vol. 78, No. 3, Dec. 7, 2017, pp. 798-808.
Wang et al., Challenges in the Development and Establishment of Exosome-Based Drug Delivery Systems, Journal of Controlled Release, 2021, vol. 329, pp. 894-906.
Wang et al., "The Use of RGD-Engineered Exosomes for Enhanced Targeting Ability and Synergistic Therapy Toward Angiogenesis", Nanoscale, vol. 9, No. 40, Jan. 1, 2017, pp. 15598-15605.
Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.
Zhao et al., "Exosomes as Drug Carriers for Cancer Therapy and Challenges Regarding Exosome Uptake" Biomedicine & Pharmacotherapy, 2020, vol. 128, 9 pages.
Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.
Abela et al., "A New Method for Isolation of Cardiac Myocytes by Percutaneous Endomyocardial Biopsy", Catheterization and Cardiovascular Diagnosis, 1996, vol. 37, pp. 227-230.
Ajijola et al., "Ventricular Tachycardia in Ischemic Heart Disease Substrates", Indian Heart Journal, 2014, pp. S24-S34, S28 & S30, vol. 66, Supplement 1.
Albini et al., "A Rapid in Vitro Assay for Quantitating the Invasive Potential of Tumor Cells", Cancer Research, Jun. 15, 1987, pp. 3239-3245, vol. 47.
Ames et al., "Oxidants, Antioxidants, and the Degenerative Diseases of Aging", Proceedings of the National Academy of Sciences of the United States of America, Sep. 1993, vol. 90, pp. 7915-7922.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Andersen et al., "Murine 'Cardiospheres' Are Not a Source of Stem Cells with Cardiomyogenic Potential," Stem Cells, 2009, vol. 27, No. 7, pp. 1571-1581.
Anversa et al., "Primitive Cells and Tissue Regeneration", Circulation Research, 2003, vol. 92, pp. 579-582.
Assmus et al., "Transplantation of Progenitor Cells and Regeneration Enhancement in Acute Myocardial Infarction (TOPCARE-AMI)", Circulation, Dec. 10, 2002, vol. 106, pp. 3009-3017.
"ATS/ACCP Statement on Cardiopulmonary Exercise Testing", American Thoracic Society/American College of Chest Physicians, American Journal of Respiratory and Critical Care Medicine, 2003, vol. 167, pp. 211-277.
Ausma et al., "Dedifferentiation of Atrial Cardiomyocytes: From in Vivo to In Vitro", Cardiovascular Research, Jul. 2002, vol. 55, No. 1, pp. 9-12.

(56) References Cited

OTHER PUBLICATIONS

Baker et al. "Adaptation to Culture of Human Embryonic Stem Cells and Oncogenesis in Vivo" Nature Biotechnology, Feb. 2007, vol. 25, No. 2, pp. 207-215.
Balser et al., "Global Parameter Optimization for Cardiac Potassium Channel Gating Models", Biophysical Journal, Mar. 1990, vol. 57, pp. 433-444.
Balser et al., "Local Anesthetics as Effectors of Allosteric Gating", Journal of Clinical Investigation, Dec. 1996, vol. 98, No. 12, pp. 2874-2886.
Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.
Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.
Barile et al., "Endogenous Cardiac Stem Cells", Progress in Cardiovascular Diseases, Jul.-Aug. 2007, vol. 50, No. 1, pp. 31-48.
Barile et al., "Human Cardiospheres as a Source of Multipotent Stem and Progenitor Cells", Hindawi Publishing Corporation, Stem Cells International, 2013, vol. 2013, pp. 10.
Barr et al., "Efficient Catheter-Mediated Gene Transfer Into the Heart Using Replication-Defective Adenovirus", Gene Therapy, Jan. 1994, vol. 1, No. 1, pp. 51-58.
Barry et al., "Differential Expression of Voltage-Gated $K^+$ Channel Subunits in Adult Rat Heart", Circulation Research, 1995, vol. 77, pp. 361-369.
Barth et al., "Lentiviral Vectors Bearing the Cardiac Promoter of the $Na^+$-$Ca^{2+}$ Exchanger Report Cardiogenic Differentiation in Stem Cells", Molecular Therapy, May 2008, vol. 16, No. 5, pp. 957-964.
Bearzi et al., "Human Cardiac Stem Cells", Proceedings of the National Academy of Sciences of the United States of America (PNAS), Aug. 28, 2007, pp. 14068-14073, vol. 104, No. 35.
Beltrami et al., "Adult Cardiac Stem Cells are Multipotent and Support Myocardial Regeneration", Cell, Sep. 19, 2003, vol. 114, No. 6, pp. 763-776.
Beltrami et al., "Evidence That Human Cardiac Myocytes Divide After Myocardial Infarction", The New England Journal of Medicine, Jun. 7, 2001, vol. 344, pp. 1750-1757.
Beltrami et al., "Multipotent Cells Can be Generated In Vitro from Several Adult Human Organs (Heart, Liver and Bone Marrow)", Stem Cells in Hematology, Blood, 2007, pp. 3438-3446, vol. 110, No. 9.
Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.
Bergmann et al., "Evidence for Cardiomyocyte Renewal in Humans", Science, Apr. 3, 2009, vol. 324, pp. 98-102.
Bernanke et al., "Effects of Hyaluronic Acid on Cardiac Cushion Tissue Cells in Collagen Matrix Cultures", Texas Reports on Biology and Medicine, 1979, pp. 271-285, vol. 39.
"Bioptome.com", Scholten Surgical Instruments, Inc., downloaded from www.bioptome.com/pages.php?page=Products, 2001, first date of publication unknown, printed on Nov. 1, 2005, pp. 2.
Bird et al., "The Human Adult Cardiomyocyte Phenotype", Cardiovascular Research, May 1, 2003, vol. 58, No. 2, pp. 423-434.
Birks et al., "Left Ventricular Assist Device and Drug Therapy for the Reversal of Heart Failure", The New England Journal of Medicine, 2006, vol. 355, No. 18, pp. 1873-1884.
Bjelakovic et al., "Mortality in Randomized Trials of Antioxidant Supplements for Primary and Secondary Prevention: Systematic Review and Meta-Analysis", JAMA, 2007, vol. 297, pp. 842-857.
Bosnali et al., "Generation of Transducible Versions of Transcription Factors Oct4 and Sox2", Biological Chemistry, Jul. 2008, vol. 389, pp. 851-861.
Bredemeyer et al., "ATM Stabilizes DNA Double-Strand-Break Complexes During V(D)J Recombination", Nature, Jul. 27, 2006, vol. 442, pp. 466-470.

Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.
Cai et al., "Injectable Glycosaminoglycan Hydrogels for Controlled Release of Human Basic Fibroblast Growth Factor," Biomaterials, 2005, vol. 26, pp. 6054-6067.
Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.
"CArdiosphere-Derived aUtologous StemCElls to Reverse ventricUlar dySfunction (CADUCEUS)", ClinicalTrials.gov, Identifier NCT00893360, 2009, pp. 6.
Chambers et al., "Functional Expression Cloning of Nanog, a Pluripotency Sustaining Factor in Embryonic Stem Cells", Cell, May 30, 2003, vol. 113, No. 5, pp. 643-655.
Chen et al., "Enhanced Tumorigenesis in p53 Knockout Mice Exposed in Utero to High-Dose Vitamin E", Carcinogenesis, 2006, vol. 27, No. 7, pp. 1358-1368.
Chen et al., "Mesenchymal Stem Cell Secretes Microparticles Enriched in Pre-MicroRNAs", Nucleic Acids Research, 2010, vol. 38, No. 1, pp. 215-224.
Chen et al., "Reduced Tumorigenesis in p53 Knockout Mice Exposed in Utero to Low-Dose Vitamin E", Cancer, Apr. 1, 2009, vol. 115, pp. 1563-1575.
Chen et al., "The Role of Notch 1 Activation in Cardiosphere Derived Cell Differentiation", Stem Cells and Development, 2012, pp. 2122-2129, vol. 21, No. 12.
Chen et al., "Vascular Endothelial Growth Factor Promotes Cardiomyocyte Differentiation of Embryonic Stem Cells", American Journal of Physiology—Heart and Circulatory Physiology, Oct. 2006, vol. 291, No. 4, pp. H1653-H1658.
Cheng et al., "Functional Performance of Human Cardiosphere-Derived Cells Delivered in an in situ Polymerizable Hyaluronan-Gelatin Hydrogel", Biomaterials, 2012, pp. 8.
Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.
Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.
Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.
Chimenti et al., "Abstract 3182: Paracrine Contribution versus Direct Regeneration in Cardiosphere-Derived Cell Therapy for Acute Myocardial Infarction", Circulation, 2009, vol. 120, p. S756.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
Chlopčíková et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.
Cho et al., "Secondary Sphere Formation Enhances the Functionality of Cardiac Progenitor Cells", Molecular Therapy, Sep. 2012, vol. 20, No. 9, pp. 1750-1766.
Christman et al., "Biomaterials for the Treatment of Myocardial Infarction", Journal of the American College Of Cardiology, 2006, vol. 48, No. 5, pp. 907-913.
Conkright et al., "A Gene Encoding an Intestinal-Enriched Member of the Krüppel-Like Factor Family Expressed in Intestinal Epithelia Cells", Nucleic Acids Research, 1999, vol. 27, No. 5, pp. 1263-1270.
Crisostomo et al., "Embryonic Stem Cells Attenuate Myocardial Dysfunction and Inflammation After Surgical Global Ischemia Via Paracrine Actions", American Journal of Physiology—Heart and Circulatory Physiology, 2008, vol. 295, pp. H1726-H1735.

(56) References Cited

OTHER PUBLICATIONS

Csete, Marie, "Oxygen in the Cultivation of Stem Cells", Annals New York Academy of Sciences, 2005, vol. 1049, pp. 1-8.
"Culture Media Database", EGM-2 (Endothelial Growth Medium 2)—ID 63, downloaded from bio.lonza.com/3018.html#ext-comp-1003:tab 63:change, printed on Jan. 14, 2013, p. 1.
Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.
Davis et al., "Validation of the Cardiosphere Method to Culture Cardiac Progenitor Cells from Myocardial Tissue", PLoS One, 2009, vol. 4, No. 9, e7195, pp. 1-8.
Davis et al., "Human Cardiospheres are a Source of Stem Cells with Cardiomyogenic Potential", Stem Cells, 2010, vol. 28, No. 5, pp. 903-904.
De Bakker et al, "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.
Deal et al., "Molecular Physiology of Cardiac Potassium Channels", Physiological Reviews, Jan. 1996, vol. 76, No. 1, pp. 49-67.
Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.
Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.
Derossi et al., "The Third Helix of the Antennapedia Homeodomain Translocates through Biological Membranes", The Journal of Biological Chemistry, Apr. 8, 1994, vol. 269, No. 14, pp. 10444-10450.
Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.
Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.
Dispersyn et al., "Dissociation of Cardiomyocyte Apoptosis and Dedifferentiation in Infarct Border Zones", European Heart Journal, 2002, vol. 23, pp. 849-857.
Dixon et al., "Quantitative Analysis of Potassium Channel mRNA Expression in Atrial and Ventricular Muscle of Rats", Circulation Research, Aug. 1994, vol. 75, No. 2, pp. 252-260.
Dixon et al., "Role of the Kv4.3 $K^+$ Channel in Ventricular Muscle", Circulation Research, 1996, vol. 79, pp. 659-668.
Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.
Donahue et al., "Ultrarapid, Highly Efficient Viral Gene Transfer to the Heart", Proceedings of the National Academy of Sciences of the United States of America, Apr. 1997, vol. 94, pp. 4664-4668.
Dong et al., "Islet Cell and Extrapancreatic Expression of the LIM Domain Homeobox Gene isl-1", Molecular Endocrinology, 1991, vol. 5, No. 11, pp. 1633-1641.
Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.
Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.
Driesen et al., "Structural Remodeling of Cardiomyocytes in the Border Zone of Infarcted Rabbit Heart", Molecular and Cellular Biochemistry, 2007, pp. 225-232, vol. 302.
Duff et al., "CD105 is Important for Angiogenesis: Evidence and Potential Applications," FASEB Journal, Jun. 2003, vol. 17, No. 9, pp. 984-992.
Eguchi, Masakatsu, "Recent Advances in Selective Opioid Receptor Agonists and Antagonists", Medicinal Research Reviews, 2004, vol. 24, No. 2, pp. 182-212.
Elliott et al., "Intercellular Trafficking and Protein Delivery by a Herpesvirus Structural Protein", Cell, Jan. 24, 1997, vol. 88, pp. 223-233.
Elliott et al., "Intercellular Trafficking of VP22-GFP Fusion Proteins", Gene Therapy, 1999, vol. 6, pp. 149-151.
Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.
Engel et al. "p38 MAP Kinase Inhibition Enables Proliferation of Adult Mammalian Cardiomyocytes", Genes & Development, May 2005, vol. 19, No. 10, pp. 1175-1187.
Eppenberger-Eberhardt et al., "Reexpression of α-Smooth Muscle Acting Isoform in Cultured Adult Rat Cardiomyocytes", Developmental Biology, Jun. 1990, vol. 139, No. 2, pp. 269-278.
Eschenhagen et al., "Engineering Myocardial Tissue", Circulation Research, 2005, vol. 97, pp. 1220-1231.
Falck et al., "Conserved Modes of Recruitment of ATM, ATR and DNA-PKcs to Sites of DNA Damage", Nature, Mar. 31, 2005, vol. 434, pp. 605-611.
Fehrer et al., "Reduced Oxygen Tension Attenuates Differentiation Capacity of Human Mesenchymal Stem Cells and Prolongs their Lifespan", Aging Cell, 2007, vol. 6, pp. 745-757.
Fiset et al., Shal-Type Channels Contribute to the $Ca^{2+}$-Independent Transient Outward $K^+$ Current in Rat Ventricle, Journal of Physiology, 1997, vol. 500, No. 1, pp. 51-64.
Foreman et al., "Reactive Oxygen Species Produced by NADPH Oxidase Regulate Plant Cell Growth", Nature, Mar. 27, 2003, vol. 422, pp. 442-446.
Frankel et al., "Cellular Uptake of the Tat Protein from Human Immunodeficiency Virus", Cell, vol. 55, Dec. 23, 1988, pp. 1189-1193.
Freyman et al., "A Quantitative, Randomized Study Evaluating Three Methods of Mesenchymal Stem Cell Delivery Following Myocardial Infarction", European Heart Journal, 2006, vol. 27, pp. 1114-1122.
Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.
Gallet et al, "Intracoronary Delivery of Self-Assembling Heart-Derived Microtissues (Cardiospheres) For Prevention of Adverse Remodeling In a Pig Model of Convalescent Myocardial Infarction", circinterventions.ahajournals.org, Dec. 8, 2015, pp. 21.
Galli et al., "Neural Stem Cells: An Overview", Circulation Research, 2003, vol. 92, No. 6, pp. 598-608.
Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.
George et al, "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.
Gibco, "Insulin-Transferrin-Selenium", Product Sheet, 2014.
Gibco, "Insulin-Transferrin-Selenium: 100X (For General Tissue Culture Applications)", Product Sheet, Form No. 2672, Jun. 2001, p. 1.

(56) References Cited

OTHER PUBLICATIONS

Gidh-Jain et al., Differential Expression of Voltage-Gated K+ Channel Genes in Left Ventricular Remodeled Myocardium After Experimental Myocardial Infarction, Circulation Research, 1996, vol. 79, pp. 669-675.
Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology—Heart and Circulatory Physiology, Apr. 2005, vol. 288, No. 4, pp. H1851-H1858.
Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.
Good et al., "β-Amyloid Peptide Blocks the Fast-Inactivating K+ Current in Rat Hippocampal Neurons", Biophysical Journal, Jan. 1996, vol. 70, pp. 296-304.
Goumans et al., "TGF-β1 Induces Efficient Differentiation of Human Cardiomyocyte Progenitor Cells into Functional Cardiomyocytes In Vitro", Stem Cell Research, 2008, vol. 1, pp. 138-149.
Grayson et al. "Hypoxia Enhances Proliferation and Tissue Formation of Human Mesenchymal Stem Cells", Biochemical and Biophysical Research Communications, 2007, vol. 358, pp. 948-953.
Green et al, "Autonomous Functional Domains of Chemically Synthesized Human Immunodeficiency Virus Tat Trans-Activator Protein", Dec. 23, 1988, Cell, vol. 55, pp. 1179-1188.
Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.
Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, pp. 99624-99636.
Grossman et al., "Contractile State of the Left Ventricle in Man as Evaluated from End-Systolic Pressure-Volume Relations", Circulation, vol. 56, No. 5, Nov. 1977, pp. 845-852.
Gu, Yiping, "Bispecific Antibody Targeted Stem Cell Therapy for Myocardial Repair", Dissertation, University of California San Francisco and University of California Berkeley, 2008, pp. 94.
Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.
Hacein-Bey-Abina et al., "LMO2-Associated Clonal T Cell Proliferation in Two Patients after Gene Therapy for SCID-X1", Science, Oct. 17, 2003, vol. 302, pp. 415-419 with Erratum in 1 page.
Hagège, Md, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. I108-I113.
Haider et al., "Bone Marrow Stem Cell Transplantation for Cardiac Repair", American Journal of Physiology—Heart and Circulatory Physiology, 2005, H2557-H2567, vol. 288.
Hainsworth et al., "The Nitrone Disodium 2,4-Sulphophenyl-N-Tert-Butylnitrone is Without Cytoprotective Effect on Sodium Nitroprusside-Induced Cell Death in N1E-115 Neuroblastoma Cells in vitro", Journal of Cerebral Blood Flow & Metabolism, 2008, vol. 28, pp. 24-28.
Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.
Harvey, "Molecular Determinants of Cardiac Development and Congenital Disease," Mouse Development, Patterning, Morphogenesis, and Organogensis, 2002, pp. 331-370, Chapter 16.
Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.

Hergenreider et al., "Atheroprotective Communication Between Endothelial Cells and Smooth Muscle Cells Through miRNAs", Nature Cell Biology, Mar. 2012, vol. 14, No. 3, pp. 249-256.
Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.
Hierlihy et al., "The Post-Natal Heart Contains a Myocardial Stem Cell Population", FEBS Letters, 2002, vol. 530, No. 1-3, pp. 239-243.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hochedlinger et al., "Nuclear Reprogramming and Pluripotency", Nature, Jun. 29, 2006, vol. 441, pp. 1061-1067.
Hu et al., "MicroRNA-210 as a Novel Therapy for Treatment of Ischemic Heart Disease", Circulation, Sep. 14, 2010, vol. 122, Supplement 11, S124-S131, pp. 17.
Hullinger et al., Inhibition of miR-15 Protects Against Cardiac Ischemic Injury, Circulation Research, Jan. 6, 2012, vol. 110, No. 1, pp. 71-81.
Ibrahim et al., "Exosomes as Critical Agents of Cardiac Regeneration Triggered by Cell Therapy", Stem Cell Reports, May 6, 2014, vol. 2, pp. 606-619.
Ibrahim et al., "Exosomes: Fundamental Biology and Roles in Cardiovascular Physiology", Annual Review of Physiology, 2016, vol. 78, pp. 67-83.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
Ivanovic, Zoran, "Hypoxia or In Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal of Clinical Investigation, Jun. 2001, pp. 1395-1402, vol. 107, No. 11.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Johnston, Md, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.
Jutkiewicz, Emily, The Antidepressant-Like Effects of Delta-Opioid Receptor Agonists, Molecular Interventions, 2006, vol., No. 3, pp. 162-169.
Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.
Kamdar et al., "Dystrophin-Deficient Cardiomyopathy", Journal of the American College of Cardiology, 2016, vol. 67, No. 21, pp. 2533-2546.
Karlsson et al., "Insulin Gene Enhancer Binding Protein Isl-1 is a Member of a Novel Class of Proteins Containing Both a Homeo-and a Cys-His Domain", Nature, Apr. 26, 1990, vol. 344, pp. 879-882.
Karoubi et al., "Single-Cell Hydrogel Encapsulation for Enhanced Survival of Human Marrow Stromal Cells", Biomaterials, 2009, vol. 30, pp. 5445-5455.
Kaspar et al., "Current Understanding and Management of Dilated Cardiomyopathy in Duchenne and Becker Muscular Dystrophy", Journal of the American Association of Nurse Practitioners, May 2009, vol. 21, No. 5, pp. 241-249.
Kawaguchi et al., "Cell Shape and Cardiosphere Differentiation: A Revelation by Proteomic Profiling", Hindawi Publishing Corporation, Biochemistry Research International, vol. 2013, Article ID 730874, pp. 1-9.

(56) References Cited

OTHER PUBLICATIONS

Kim et al., "Generation of Human Induced Pluripotent Stem Cells by Direct Delivery of Reprogramming Proteins", Cell Stem Cell, Jun. 5, 2009, vol. 4, No. 6, pp. 472-476.
Kisselbach et al., "CD90 Expression on Human Primary Cells and Elimination of Contaminating Fibroblasts from Cell Cultures", Cytotechnology, 2009, pp. 31-44, vol. 59.
Kooijmans et al., "PEGylated and Targeted Extracellular Vesicles Display Enhanced Cell Specificity and Circulation Time", Journal of Controlled Release, 2016, vol. 224, pp. 77-85.
Kühn et al., "Periostin Induces Proliferation of Differentiated Cardiomyocytes and Promotes Cardiac Repair", Nature Medicine, Aug. 2007, vol. 13, No. 8, pp. 962-969.
Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. I167-I173.
Kwon et al., "Cellular Manipulation of Human Embryonic Stem Cells by TAT-PDX1 Protein Transduction," Molecular Therapy, Jul. 1, 2005, vol. 12, No. 1, pp. 28-32.
Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.
Laflamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.
Lai et al., "Exosome Secreted by MSC Reduces Myocardial Ischemia/Reperfusion Injury", Stem Cell Research, 2010, vol. 4, pp. 214-222.
Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.
Landázuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.
Lavon et al., "Derivation of Euploid Human Embryonic Stem Cells from Aneuploid Embryos", Stem Cells, 2008, vol. 26, pp. 1874-1882.
Lee et al., "Antibody Targeting of Stem Cells to Infarcted Myocardium", Stem Cells: Translational and Clinical Research, 2007, pp. 712-717, vol. 25.
Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Leferovich et al., "Heart Regeneration in Adult MRL Mice", Proceedings of the National Academy of Sciences of the United States of America (PNAS), Aug. 14, 2001, vol. 98, No. 17, pp. 9830-9835.
Leor, Md, et al., "Transplantation of Fetal Myocardial Tissue Into the Infarcted Myocardium of Rat", Circulation, Nov. 1, 1996, vol. 94, No. 9, II-332-II-336.
Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.
Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.
Li et al., "Cardiospheres Recapitulate a Niche-Like Microenvironment Rich in Stemness and Cell-Matrix Interactions, Rationalizing Their Enhanced Functional Potency for Myocardial Repair", Stem Cells: Translational and Clinical Research, 2010, pp. 2088-2098, vol. 28.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.
Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.
Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105, No. 12, p. e58.
Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.
Li, Md, PhD et al., "Imaging Survival and Function of Transplanted Cardiac Resident Stem Cells", Journal of the American College of Cardiology, Apr. 7, 2009, vol. 53, No. 14, pp. 1229-1240.
Liao et al., "Enhanced Efficiency of Generating Induced Pluripotent Stem (iPS) Cells from Human Somatic Cells by a Combination of Six Transcription Factors", Cell Research, 2008, vol. 18, pp. 600-603.
Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.
Lindsay, Mark A., "Peptide-Mediated Cell Delivery: Application in Protein Target Validation", Current Opinion in Pharmacology, 2002, vol. 2, pp. 587-594.
Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.
Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.
Liu et al. "Autologous Stem Cell Transplantation for Myocardial Repair", American Journal of Physiology, Heart and Circulatory Physiology, 2004, pp. H501-H511, vol. 287.
Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, pp. 3405-3416, vol. 12, No. 12.
Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.
Lum et al., "The New Face of Bispecific Antibodies: Targeting Cancer and Much More", Experimental Hematology, 2006, pp. 1-6, vol. 34.
Lyngbaek et al., "Cardiac Regeneration by Resident Stem and Progenitor Cells in the Adult Heart", Basic Research in Cardiology, 2007, vol. 102, pp. 101-114.
Maitra et al., Genomic Alterations in Cultured Human Embryonic Stem Cells, Nature Genetics, Oct. 2005, vol. 37, No. 10, pp. 1099-1103.
Maletic-Savatic et al., "Differential Spatiotemporal Expression of $K^+$ Channel Polypeptides in Rat Hippocampal Neurons Developing In Situ and In Vitro", The Journal of Neuroscience, May 1995, vol. 15, No. 5, pp. 3840-3851.

(56) References Cited

OTHER PUBLICATIONS

Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.

Marbán, Eduardo, "Big Cells, Little Cells, Stem Cells: Agents of Cardiac Plasticity", Circulation Research, 2007, vol. 100, No. 4, pp. 445-446.

Marshall et al., "The Jellyfish Green Fluorescent Protein: A New Tool for Studying Ion Channel Express and Function", Neuron, Feb. 1995, vol. 14, pp. 211-215.

Martens et al., "Percutaneous Cell Delivery Into the Heart Using Hydrogels Polymerizing In Situ", Cell Transplantation, 2009, vol. 18, No. 3, pp. 297-304.

Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.

McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.

Mehmel et al., "The Linearity of the End-Systolic Pressure-Volume Relationship in Man and its Sensitivity for Assessment of Left Ventricular Function", Circulation, 1981, vol. 63, pp. 1216-1222.

Messina et al., "Isolation and Expansion of Adult Cardiac Stem Cells from Human and Murine Heart", Oct. 29, 2004, Circulation Research, Cellular Biology, American Heart Association, vol. 95, pp. 911-921.

Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.

Miller III, et al., Meta-Analysis: High-Dosage Vitamin E Supplementation May Increase All-Cause Mortality, Annals of Internal Medicine, 2005, vol. 142, pp. 37-46.

Miltenyi et al., "High Gradient Magnetic Cell Separation With MACS[1]", Cytometry, 1990, pp. 231-238, vol. 11.

Mitsui et al., "The Homeoprotein Nanog is Required for Maintenance of Pluripotency in Mouse Epiblast and ES Cells", Cell, May 30, 2003, vol. 113, No. 5, pp. 631-642.

Miyazono et al. "Latent High Molecular Weight Complex of Transforming Growth Factor β1", May 5, 1988, vol. 263, No. 13, pp. 6407-6415.

Montessuit et al., "Regulation of Glucose Transporter Expression in Cardiac Myocytes: p38 MAPK is a Strong Inducer of GLUT4", Cardiovascular Research, Oct. 1, 2004, vol. 64, No. 1, pp. 94-104.

Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.

Moss et al., "Conservation of the Heterochronic Regulator Lin-28, its Developmental Expression and MicroRNA Complementary Sites", Developmental Biology, 2003, vol. 258, No. 2, pp. 432-442.

Moss, M.D., et al., Prophylactic Implantation of a Defibrillator in Patients with Myocardial Infarction and Reduced Ejection Fraction, The New England Journal of Medicine, Mar. 21, 2002, vol. 346, No. 12, pp. 877-883.

Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.

Nadal-Ginard et al., "Myocyte Death, Growth, and Regeneration in Cardiac Hypertrophy and Failure", Circulation Research, 2003, vol. 92, pp. 139-150.

Nadal-Ginard et al, "A Matter of Life and Death: Cardiac Myocyte Apoptosis and Regeneration", Journal of Clinical Investigation, May 2003, vol. 111, No. 10, pp. 1457-1459.

Naka et al., "Regulation of Reactive Oxygen Species and Genomic Stability in Hematopoietic Stem Cells", Antioxidants & Redox Signaling, 2008, vol. 10, No. 11, pp. 1883-1894.

Nakagawa et al., "Generation of Induced Pluripotent Stem Cells without Myc from Mouse and Human Fibroblasts", Nature Biotechnology, Jan. 2008, vol. 26, No. 1, pp. 101-106.

Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.

Nelson et al., "CXCR4+/FLK-1+ Biomarkers Select a Cardiopoietic Lineage from Embryonic Stem Cells", Stem Cells, 2008, vol. 26, pp. 1464-1473.

Nelson, Md, PhD et al., "Repair of Acute Myocardial Infarction with iPS Induced by Human Stemness Factors", Circulation, Aug. 4, 2009, vol. 120, No. 5, pp. 408-416.

Niethammer et al., "A Tissue-Scale Gradient of Hydrogen Peroxide Mediates Rapid Wound Detection in Zebrafish", Nature, Jun. 18, 2009, vol. 459, pp. 996-999.

Noguchi et al., "Protein Transduction Technology: A Novel Therapeutic Perspective", Acta Medica Okayama, 2006, vol. 60, No. 1, pp. 1-11.

Nussbaum et al., "Transplantation of Undifferentiated Murine Embryonic Stem Cells in the Heart: Teratoma Formation and Immune Response", The FASEB Journal, Research Communication, May 2007, vol. 21, No. 7, pp. 1345-1357.

Odelberg et al., "Dedifferentiation of Mammalian Myotubes Induced by msx1", Cell, Dec. 22, 2000, vol. 103, No. 7, pp. 1099-1109.

Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.

Offord et al., "Photoprotective Potential of Lycopene, -Carotene, Vitamin E, Vitamin C and Carnosic in UVA-Irradiated Human Skin Fibroblasts", Free Radical Biology & Medicine, 2002, vol. 32, No. 12, pp. 1293-1303.

Oh et al., "Cardiac Muscle Plasticity in Adult and Embryo by Heart-Derived Progenitor Cells", Annals of the New York Academy of Sciences, 2004, vol. 1015, pp. 182-189.

Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, pp. 12313-12318, vol. 100, No. 21.

Okita et al., Generation of Mouse Induced Pluripotent Stem Cells Without Viral Vectors, Nov. 7, 2008, Science, vol. 322, pp. 949-953.

Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, circ.ahajournals.org/content/132/Suppl 3/A13381.short.

Owusu-Ansah et al., "Reactive Oxygen Species Prime *Drosophila* Haematopoietic Progenitors for Differentiation", Nature, Sep. 24, 2009, vol. 461, pp. 537-541.

Park et al., "Reprogramming of Human Somatic Cells to Pluripotency with Defined Factors", Nature, Jan. 10, 2008, vol. 451, pp. 141-146.

Passier et al., "Stem-Cell-Based Therapy and Lessons from the Heart", May 15, 2008, Nature, vol. 453, pp. 322-329.

Passier et al., "Origin and Use of Embryonic and Adult Stem Cells in Differentiation and Tissue Repair", Cardiovascular Research, 2003, vol. 58, No. 2, pp. 324-335.

Payne, Anthony G., "Using Immunomagnetic Technology and Other Means to Facilitate Stem Cell Homing", Medical Hypotheses, 2004, pp. 718-720, vol. 62.

Peterson, Md, MPH, et al., "Risk Stratification After Myocardial Infarction", Annals of Internal Medicine, 1997, vol. 126, No. 7, pp. 561-582.

Pike et al., "Heparin-Regulated Release of Growth Factors In Vitro and Angiogenic Response In Vivo to Implanted Hyaluronan Hydrogels Containing VEGF and bFGF," Biomaterials, 2006, vol. 27, pp. 5242-5241.

Piper et al. "Determinants of Cardiomyocyte Development in Long-Term Primary Culture", Journal of Molecular and Cellular Cardiology, 1988, vol. 20, pp. 825-835.

Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.

Potapova et al., "Enhanced Recovery of Mechanical Function in the Canine Heart by Seeding an Extracellular Matrix Patch with Mesenchymal Stem Cells Committed to a Cardiac Lineage", Ameri-

(56) References Cited

OTHER PUBLICATIONS can Journal of Physiology—Heart and Circulatory Physiology, 2008, vol. 295, pp. H2257-H2263.

Prestwich et al., "The Translational Imperative: Making Cell Therapy Simple and Effective", Acta Biomaterialia, 2012, vol. 8, pp. 4200-4207.

Prunier et al., "Delayed Erythropoietin Therapy Reduces Post-MI Cardiac Remodeling Only at a Dose that Mobilizes Endothelial Progenitor Cells", American Journal of Physiology—Heart and Circulatory Physiology, 2007, vol. 292, pp. H522-H529.

Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.

Qin et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.

Quaini et al., "Chimerism of the Transplanted Heart", The New England Journal of Medicine, Jan. 3, 2002, vol. 346, No. 1, pp. 5-15.

Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United States of America (PNAS), Aug. 18, 2009, vol. 106, No. 33, p. 14022-14027.

Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.

Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.

Reiffel, James A., MD, FACC "Ten Pearls for the Use of Antiarrhythmic Drugs for Atrial Fibrillation", Aug. 17, 2012, Retrieved from www.acc.org/latest-in-cardiology/articles/2014/07/18/15/12/ten-pearls-for-the-use-of-antiarrhythmic-drugs-for-atrial-fibrillation, pp. 17.

Riazifar et al., "Stem Cell Extracellular Vesicles: Extended Messages of Regeneration", Reviews in Advance, Oct. 19, 2016, vol. 14, No. 1, pp. 1-30.

Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.

Risebro et al., "Hand1 Regulates Cardiomyocyte Proliferation Versus Differentiation in the Developing Heart", Development, Nov. 2006, vol. 133, No. 22, pp. 4595-4606.

Rossi et al., "Deficiencies in DNA Damage Repair Limit the Function of Haematopoietic Stem Cells with Age", Nature, Jun. 7, 2007, vol. 447, pp. 725-729.

Rotwein et al., "Organization and Sequence of the Human Insulin-Like Growth Factor I Gene", The Journal of Biological Chemistry, Apr. 15, 1986, vol. 261, No. 11, pp. 4828-4832.

Rubio et al., "Spontaneous Human Adult Stem Cell Transformation", Cancer Research, 2005, vol. 65, pp. 3035-3039.

Rücker-Martin et al., "Dedifferentiation of Atrial Myocytes During Atrial Fibrillation: Role of Fibroblast Proliferation in Vitro", Cardiovascular Research, 2002, vol. 55, pp. 38-52.

Rudy, B. "Diversity and Ubiquity of K Channels", Neuroscience, 1988, vol. 25, No. 3, pp. 729-749.

Saito et al., "Cell Death Caused by Selenium Deficiency and Protective Effect of Antioxidants", The Journal of Biological Chemistry, Oct. 10, 2003, vol. 278, No. 41, pp. 39428-39434.

Sareen et al., Chromosome 7 and 19 Trisomy in Cultured Human Neural Progenitor Cells, PLoS One, Oct. 2009, vol. 4, No. 10, e7630, pp. 12.

Sasano et al., "Molecular Ablation of Ventricular Tachycardia after Myocardial Infarction", Natural Medicine, 2006, vol. 12, No. 11, pp. 1256-1258.

Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.

Scaria et al., "Host-Virus Genome Interactions: Marco Roles for MicroRNAs", Cellular Microbiology, 2007, vol. 9, No. 12, pp. 2784-2794.

Seifried et al., "A Review of the Interaction Among Dietary Antioxidants and Reactive Oxygen Species", Journal of Nutritional Biochemistry, 2007, vol. 18, pp. 567-579.

Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.

Serôdio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.

Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.

Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.

Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.

Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.

Shen et al. "Isolation of an Insulin-Like Growth Factor II cDNA with a Unique 5' Untranslated Region from Human Placenta", Mar. 1988, Proceedings of the National Academy of Sciences of the United States of America (PNAS), vol. 85, pp. 1947-1951.

Shenje et al., "Lineage Tracing of Cardiac Explant Derived Cells", PLoS One, Apr. 2008, vol. 3, No. 4, e1929, pp. 10.

Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.

Shu et al., "Disulfide-Crosslinked Hyaluronan-Gelatin Hydrogel Films: A Covalent Mimic of the Extracellular Matrix for In Vitro Cell Growth", Biomaterials, 2003, vol. 24, pp. 3825-3834.

Sigma-Aldrich, Inc., "Nutrient Mixture F12 Ham Kaighn's Modification (F12K)", Product Description, May 2007, pp. 2.

Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.

Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.

Singh, et al. "High-Dose α-Tocopherol Therapy Does Not Affect HDL Subtractions in Patients with Coronary Artery Disease on Statin Therapy", Clinical Chemistry, 2007, vol. 53, No. 3, pp. 525-528.

Slaughter, Md et al., "Clinical Management of Continuous-Flow Left Ventricular Assist Devices in Advanced Heart Failure", The Journal of Heart and Lung Transplantation, Apr. 2010, vol. 29, No. 4S, pp. S1-39.

Smart et al., "De Novo Cardiomyocytes from Within the Activated Adult Heart After Injury", Nature, Jun. 30, 2011, vol. 474, pp. 640-646.

Smith, PhD et al., "Stem Cells in the Heart: What's the Buzz all About? Part 1: Preclinical Considerations", Heart Rhythm, May 2008, vol. 5, No. 5, pp. 749-757.

Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.

Smith et al., "Regenerative Potential of Cardiosphere-Derived Cells Expanded From Percutaneous Endomyocardial Biopsy Specimens", Circulation, Feb. 5, 2007, pp. 896-908, vol. 115.

(56) References Cited

OTHER PUBLICATIONS

Smith et al., "Unique Phenotype of Cardiospheres Derived from Human Endomyocardial Biopsies", Circulation, Supplement II, Oct. 25, 2005, pp. 2, vol. 112, No. 17.

Smith et al., "Unselected Human Cardiosphere-derived Cells are Functionally Superior to c-Kit- or CD90-Purified Cardiosphere-Derived Cells", Circulation, Supplement 2, Oct. 28, 2008, vol. 118, No. 17, p. 1.

Smits, Anke Maria, "Cell-Based Cardiac Repair", Thesis, Utrecht University, The Netherlands, 2009, pp. 180.

Srivastava et al., "Thymosin β4 Is Cardioprotective after Myocardial Infarction", Annals of the New York Academy of Sciences, Sep. 2007, vol. 1112, pp. 161-170. Abstract only.

Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.

Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.

Sussman, Mark A., "Myocardial Aging and Senescence: Where Have the Stem Cells Gone?" Annual Review of Physiology, 2004, vol. 66, pp. 29-48.

Takahashi et al., "Induction of Pluripotent Stem Cells from Adult Human Fibroblasts by Defined Factors," Cell, vol. 131, Nov. 30, 2007, pp. 861-872.

Takahashi et al., "Induction of Pluripotent Stem Cells from Fibroblast Cultures, Nature Protocols", 2007, vol. 2 No. 12, pp. 3081-3089.

Takeda et al., "Human Oct3 Gene Family: cDNA Sequences, Alternative Splicing, Gene Organization, Chromosomal Location, and Expression at Low Levels in Adult Tissues", Nucleic Acids Research, 1992, vol. 20, No. 17, pp. 4613-4620.

Takehara, Md, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.

Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.

Tateishi et al., "Clonally Amplified Cardiac Stem Cells are Regulated by Sca-1 Signaling for Efficient Cardiovascular Regeneration", Journal of Cell Science, 2007, vol. 120, No. 10, pp. 1791-1800.

Ten Dijke et al. "Identification of Another Member of the Transforming Growth Factor Type β Gene Family", Proceedings of the National Academy of Sciences of the United States of America (PNAS), 1988, vol. 85, pp. 4715-4719.

Terrovitis, Md, et al., "Assessment and Optimization of Cell Engraftment after Transplantation into the Heart", Circulation Research, Feb. 19, 2010, vol. 106, No. 3, pp. 479-494.

Terrovitis, Md, et al., "Noninvasive Quantification and Optimization of Acute Cell Retention by In Vivo Positron Emission Tomography after Intramyocardial Cardiac-Derived Stem Cell Delivery", Journal of the American College of Cardiology, Oct. 20, 2009, vol. 54, No. 17, pp. 1619-1626.

Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.

Torella et al., "Cardiac Stem Cell and Myocyte Aging, Heart Failure, and Insulin-Like Growth Factor-1 Overexpression", Circulation Research, 2004, vol. 95, pp. 514-524.

Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.

Trevethick et al., "Treating Lung Inflammation with Agonists from the Adenosine A2A Receptor: Promises, Problems and Potential Solutions", British Journal of Pharmacology, 2008, vol. 155, pp. 463-474.

Tsagalou, Md, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.

Tseliou et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.

Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.

Uemura et al., "Bone Marrow Stem Cells Prevent Left Ventricular Remodeling of Ischemic Heart Through Paracrine Signaling", Circulation Research, 2006, vol. 98, pp. 1414-1421.

Ueno et al., "Biphasic Role for Wnt/β-Catenin Signaling in Cardiac Specification in Zebrafish and Embryonic Stem Cells", Proceedings of the National Academy of Sciences of the United States of America (PNAS), Jun. 5, 2007, vol. 104, No. 23, pp. 9685-9690.

Ulloa-Montoya et al., "Culture Systems for Pluripotent Stem Cells", Journal of Bioscience and Bioengineering, 2005, vol. 100, No. 1, pp. 12-27.

Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.

Urbanek et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.

Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.

Van Der Geest et al., "Quantification in Cardiac MRI", Journal of Magnetic Resonance Imaging, 1999, vol. 10, pp. 602-608.

Van Gent et al., "Chromosomal Stability and the DNA Double-Stranded Break Connection", Nature, Mar. 2001, vol. 2, pp. 196-206.

Van Vliet et al., "Progenitor Cells Isolated from the Human Heart: a Potential Cell Source for Regenerative Therapy", Netherlands Heart Journal, May 2008, vol. 16, No. 5, pp. 163-169.

Van Winkle et al, "Cardiogel: A Biosynthetic Extracellular Matrix for Cardiomyocyte Culture", In Vitro Cellular & Developmental Biology—Animal, Sep. 1996, vol. 21, pp. 478-485.

Vela et al., "Quest for the Cardiovascular Holy Grail: Mammalian Myocardial Regeneration", Cardiovascular Pathology, 2008, vol. 17, No. 1-5.

Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, May 11, 2007, vol. 282, No. 19, pp. 14243-14252.

Von Harsdorf, R., "Can Cardiomyocytes Divide?" Heart, 2001, vol. 86, pp. 481-482.

Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.

Wagner, Richard, "The State of the Art in Antisense Research", Nature Medicine, Nov. 1995, vol. 1, No. 11, pp. 1116-1118.

Walder et al., "Up-Regulation of Neural Stem Cell Markers Suggests the Occurrence of Dedifferentiation in Regenerating Spinal Cord", Development Genes and Evolution, 2003, vol. 213, pp. 625-630.

Walravens et al., "Cardiosphere-Derived Cell and Mesenchymal Stem Cell Extracellular Vesicles Contain Distinct RNA Cargo", Scientific Program, ISEV2017, Dec. 2017, p. 173.

(56) References Cited

OTHER PUBLICATIONS

Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.
Wang et al., "Establishment of New Mouse Embryonic Stem Cell Lines is Improved by Physiological Glucose and Oxygen", Cloning and Stem Cells, 2006, vol. 8, No. 2, pp. 108-116.
WERNIG el al., "c-Myc Is Dispensable for Direct Reprogramming of Mouse Fibroblasts", Cell Stem Cell, Jan. 2008, vol. 2, pp. 10-12.
White et al. "Intrinsic Cardiac Origin of Human Cardiosphere-Derived Cells", European Heart Journal, 2013, vol. 34, pp. 68-75.
Wilmut et al., "Viable Offspring Derived from Fetal and Adult Mammalian Cells", Nature, Feb. 27, 1997, vol. 385, pp. 810-813.
Wilson et al., "Bioluminescence Reporter Gene Imaging of Human Embryonic Stem Cell Survival, Proliferation, and Fate", Methods in Molecular Biology, 2009, vol. 574, pp. 87-103.
Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.
Wu et al., "Cellular Therapy and Myocardial Tissue Engineering: The Role of Adult Stem and Progenitor Cells", European Journal of Cardio-Thoracic Surgery, 2006, vol. 30, pp. 770-781.
Yamada et al., "Type V Collagen-Induced Oral Tolerance Plus Low-Dose Cyclosporine Prevents Rejection of MHC Class I and II Incompatible Lung Allografts", The Journal Immunology, Jul. 1, 2009, vol. 183, No. 1, pp. 237-245.
Yang et al., "Human Cardiovascular Progenitor Cells Develop from a KDR+ Embryonic-Stem-Cell-Derived Population", Nature, May 22, 2008, vol. 453, pp. 524-528.
Yau Md et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.
Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", PLOS One, Dec. 2, 2014, pp. 1-29.
Yu et al., "Induced Pluripotent Stem Cell Lines Derived from Human Somatic cells," Science, Dec. 21, 2007, vol. 318, pp. 1917-1920.
Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.
Zammit et al., "The Skeletal Muscle Satellite Cell: Stem Cell or Son of Stem Cell?" Differentiation, 2001, vol. 68, pp. 193-204.
Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.
Zhang et al., "Do Cardiac Stem Cells Arise from Cardiomyocyte Dedifferentiation?" Circulation Research, Nov. 2006, vol. 99, No. 11, p. 1278. Abstract only.
Zhao et al., "Targeting Human CD34+ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.
Zhou et al., "Down-Regulation of microRNA-26a Promotes Mouse Hepatocyte Proliferation During Liver Regeneration", PLoS ONE, Apr. 2012, vol. 7, No. 4, e33577, pp. 1-7.
Zhou et al., "Generation of Induced Pluripotent Stem Cells Using Recombinant Proteins", Cell Stem Cell, May 1, 2009, vol. 4, No. 5, pp. 381-384.
Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.
International Search Report and Written Opinion received in PCT Application No. PCT/US2017/052350, dated Dec. 11, 2017 in 8 pages.
International Preliminary Report on Patentability and Written Opinion received in PCT/US2017/052350, dated Apr. 4, 2019 in 7 pages.

* cited by examiner

Figure 2.
Fig. 2A
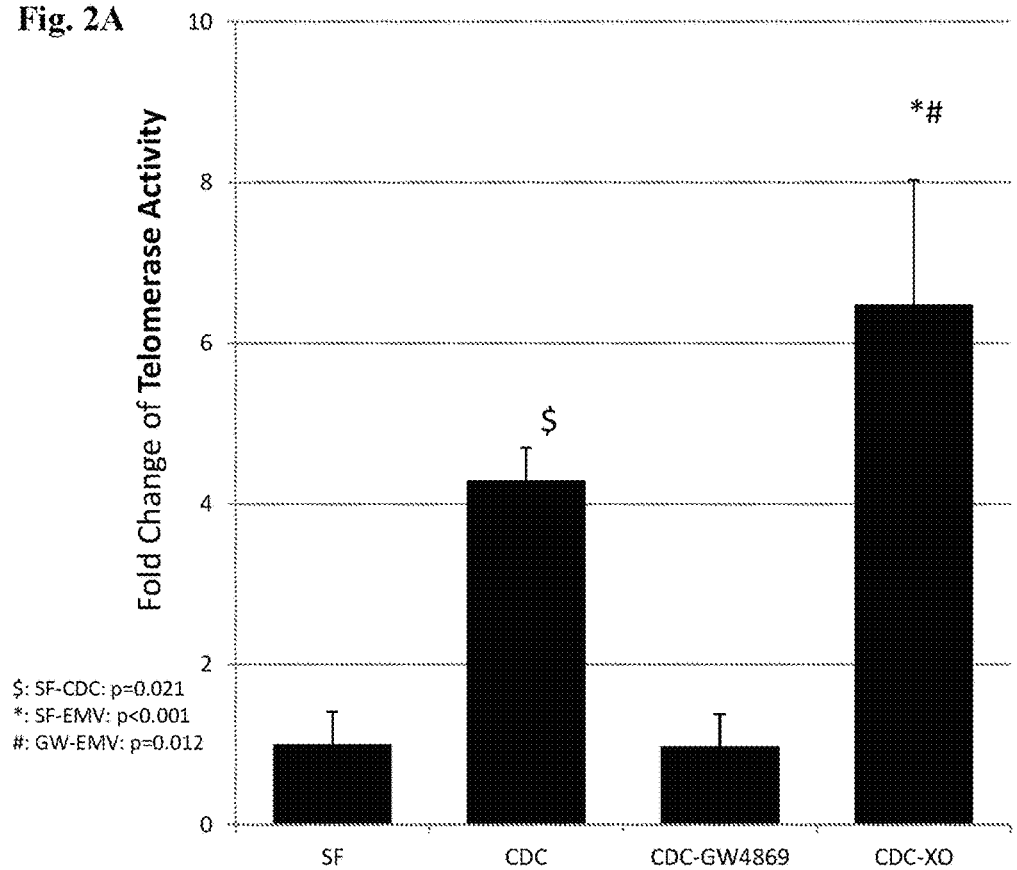
Fig. 2B
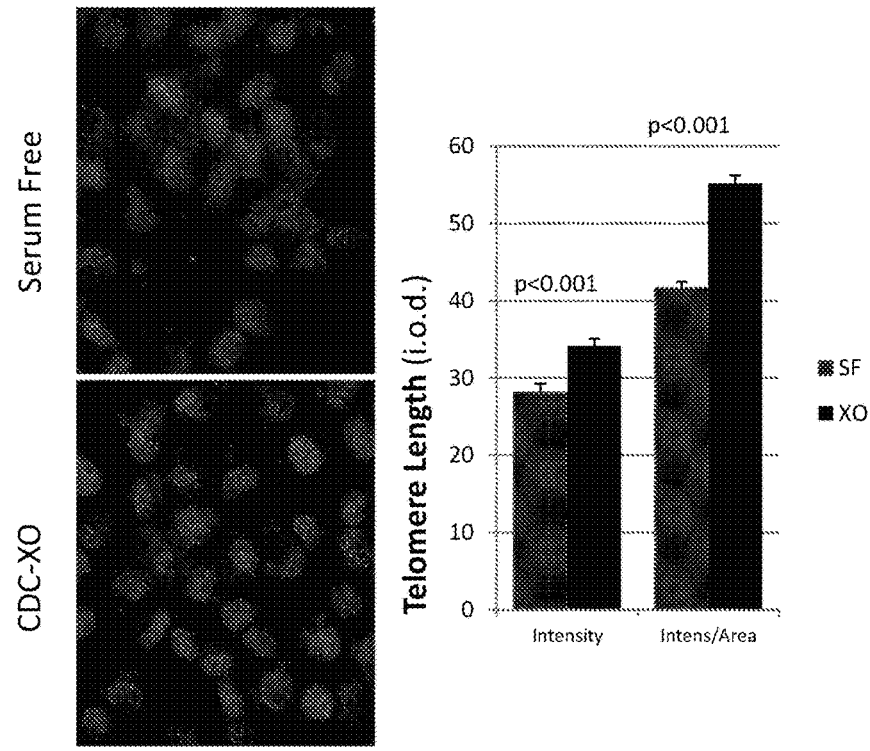

Figure 2.
Fig. 2C
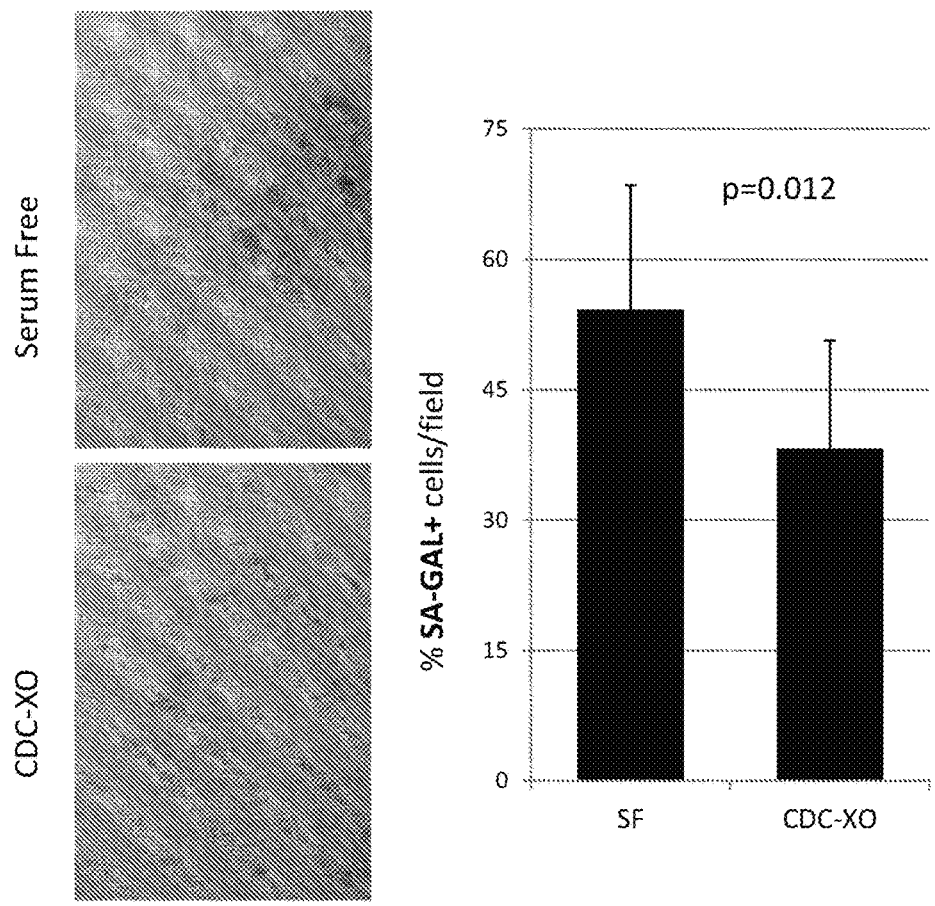
Fig. 2D
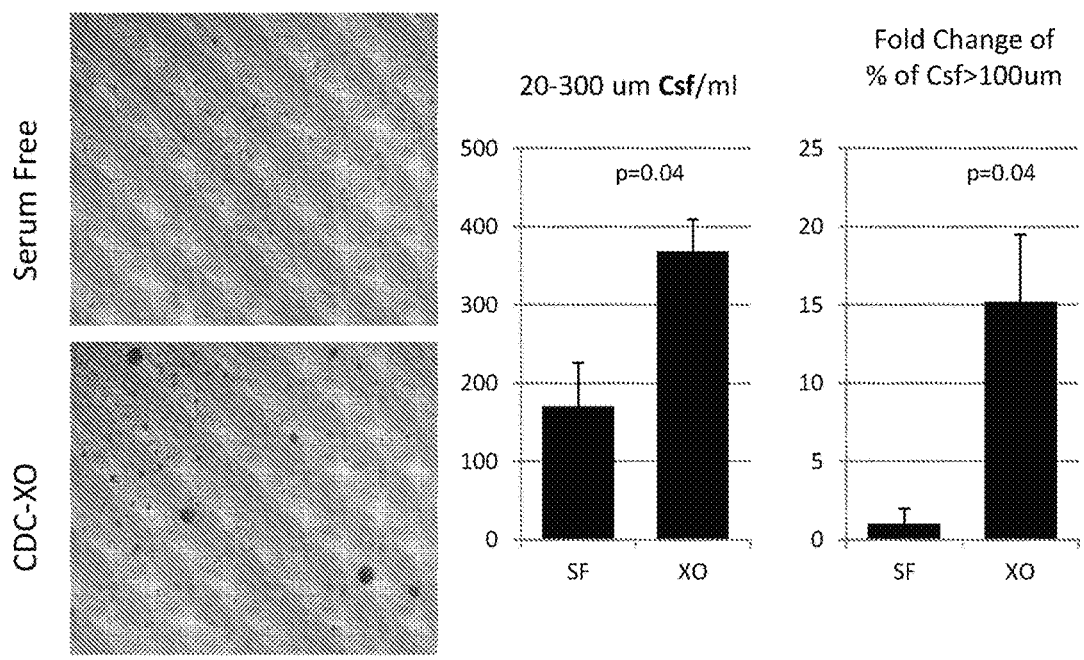

Figure 3.
Fig. 3A
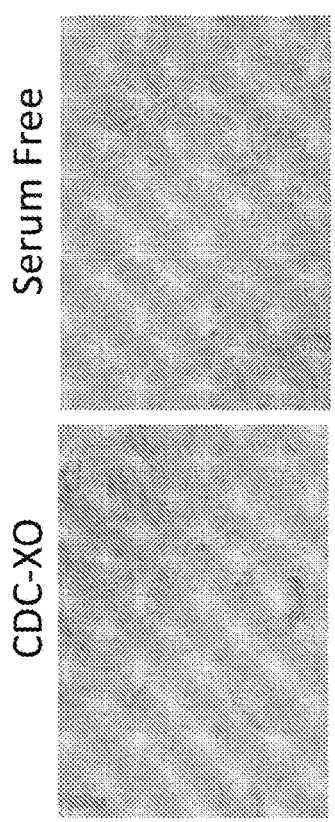
Fig. 3B
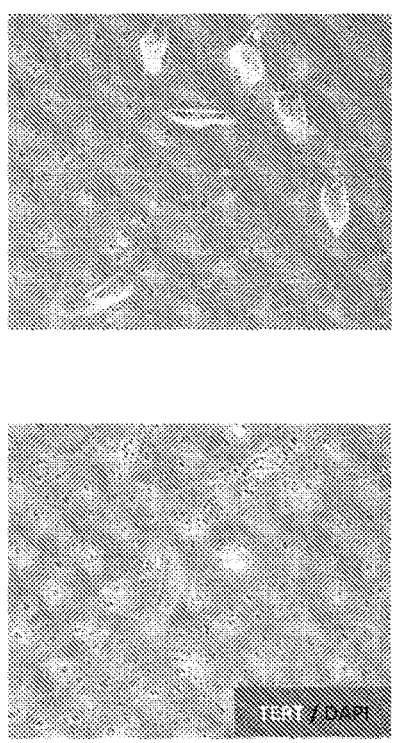
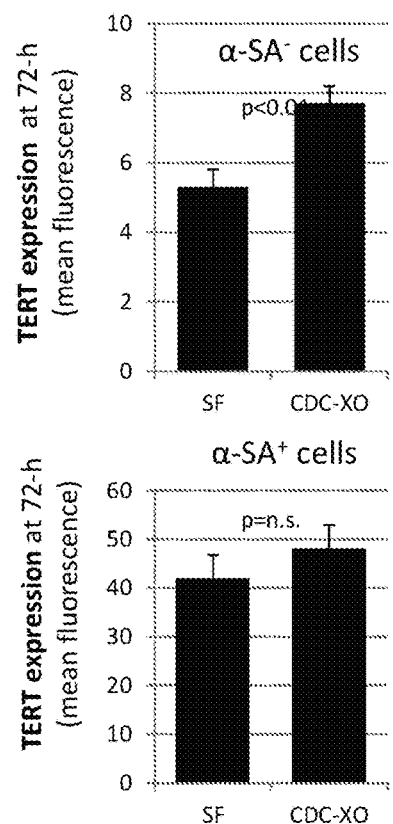
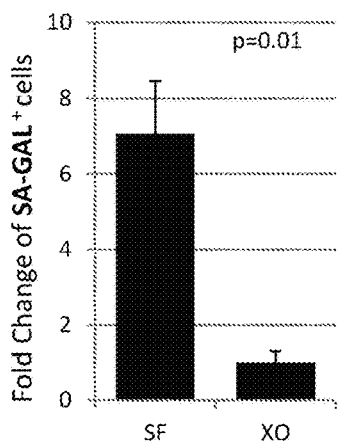
Fig. 3C
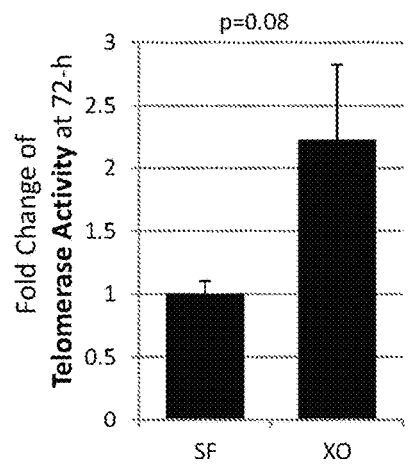

Figure 8.
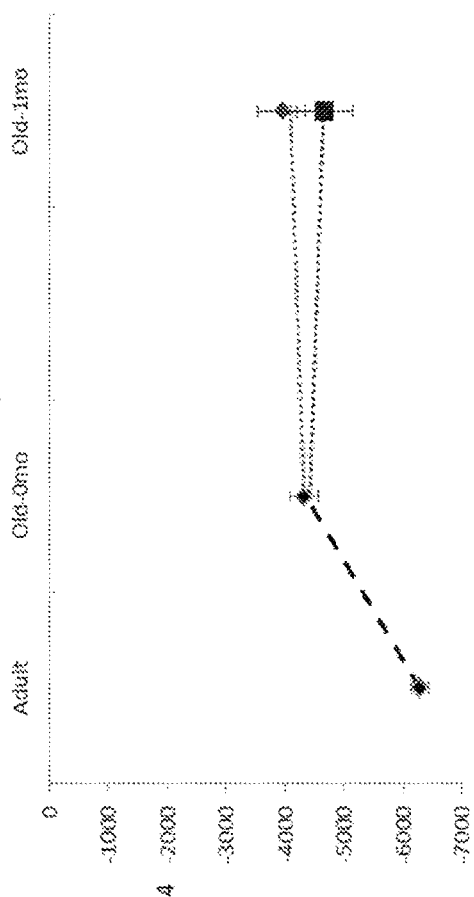
Fig. 8A
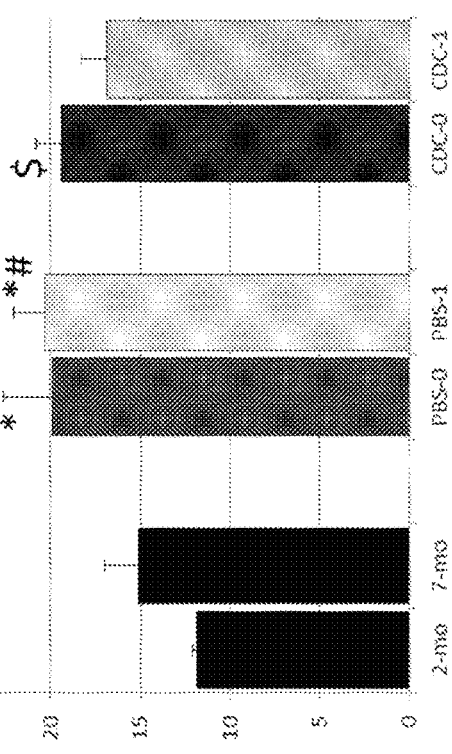
Fig. 8C
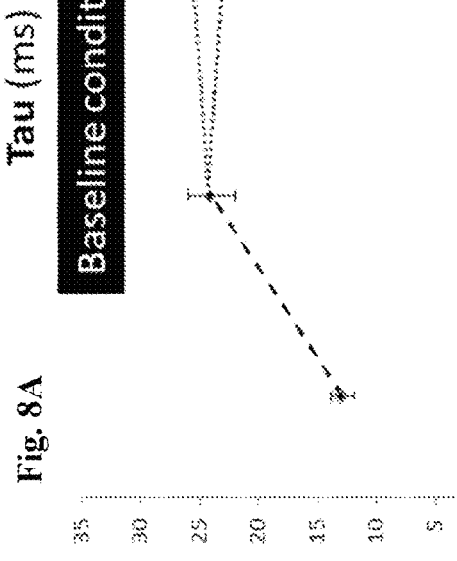
Fig. 8B

Figure 9.
Fig. 9A.
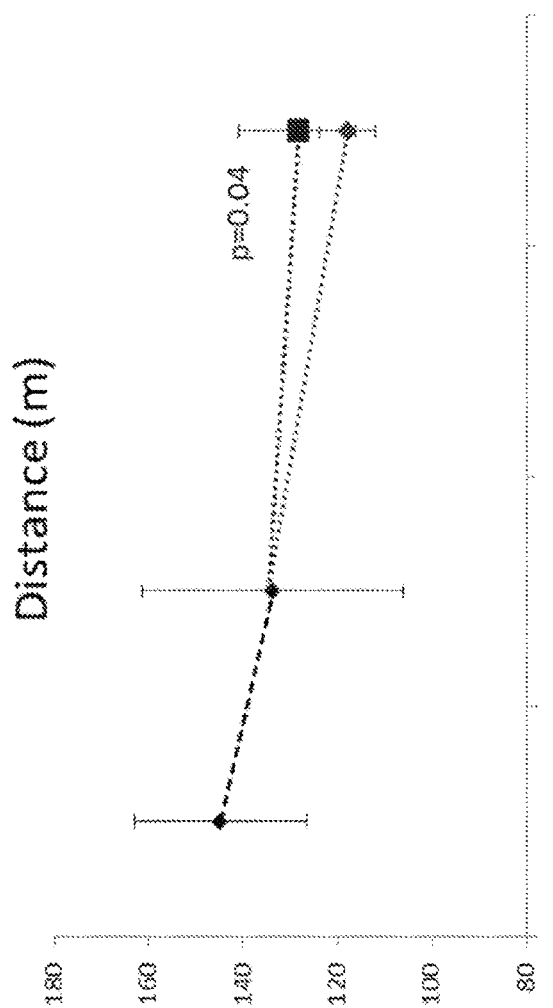
Fig. 9B.
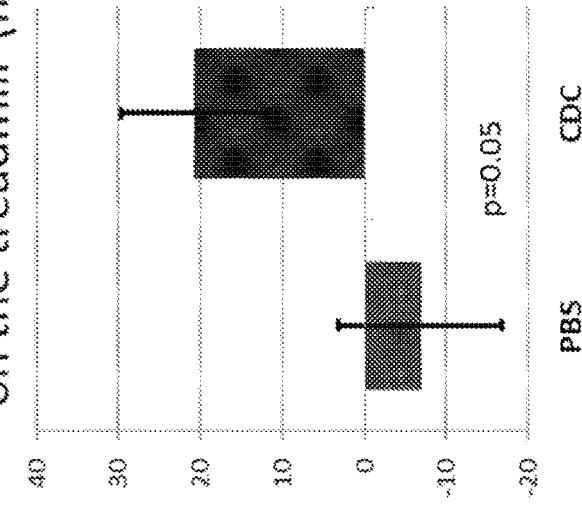

Figure 10.
Fig. 10A.
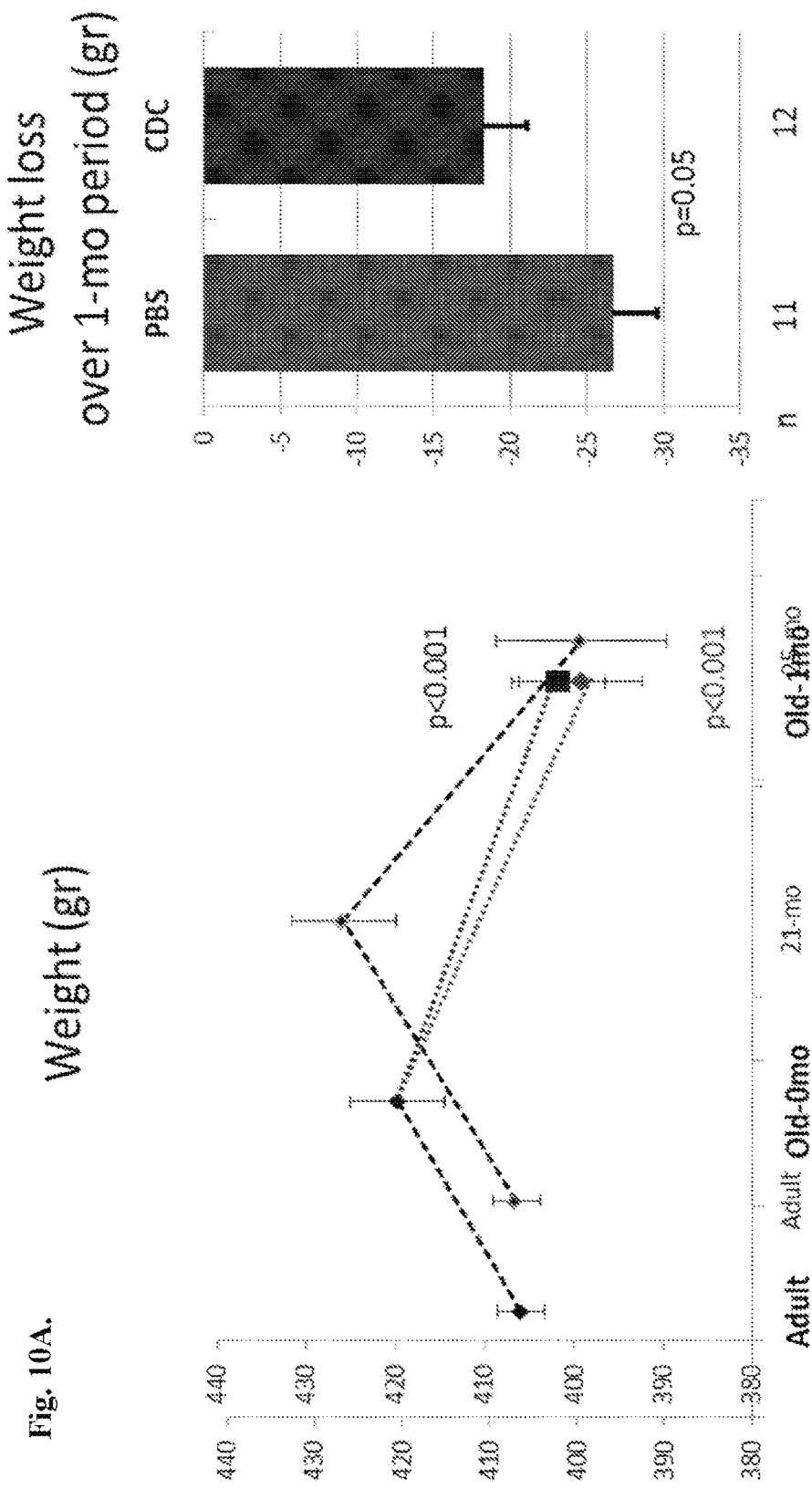
Fig. 10B.
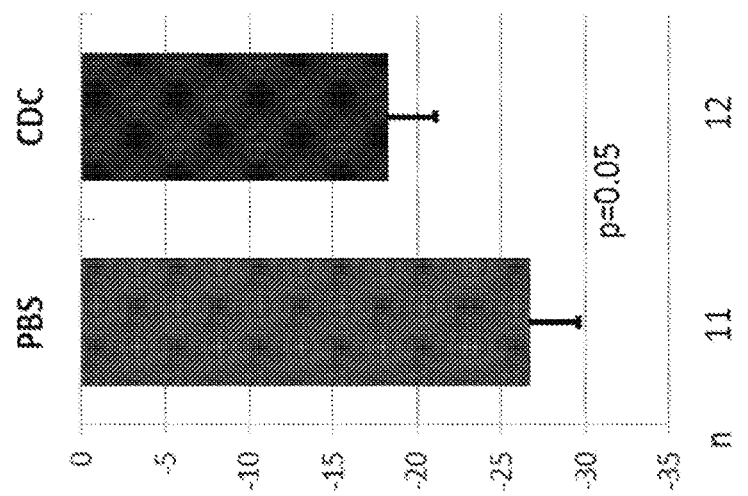

Figure 13.
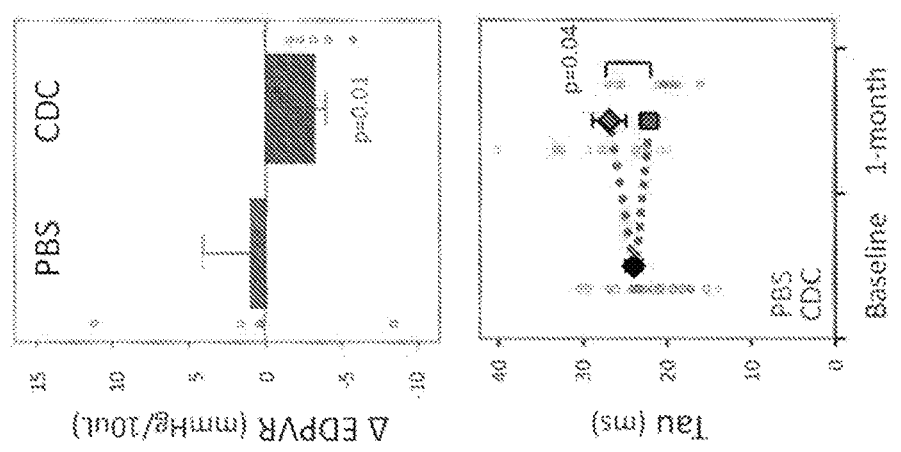
Fig. 13D
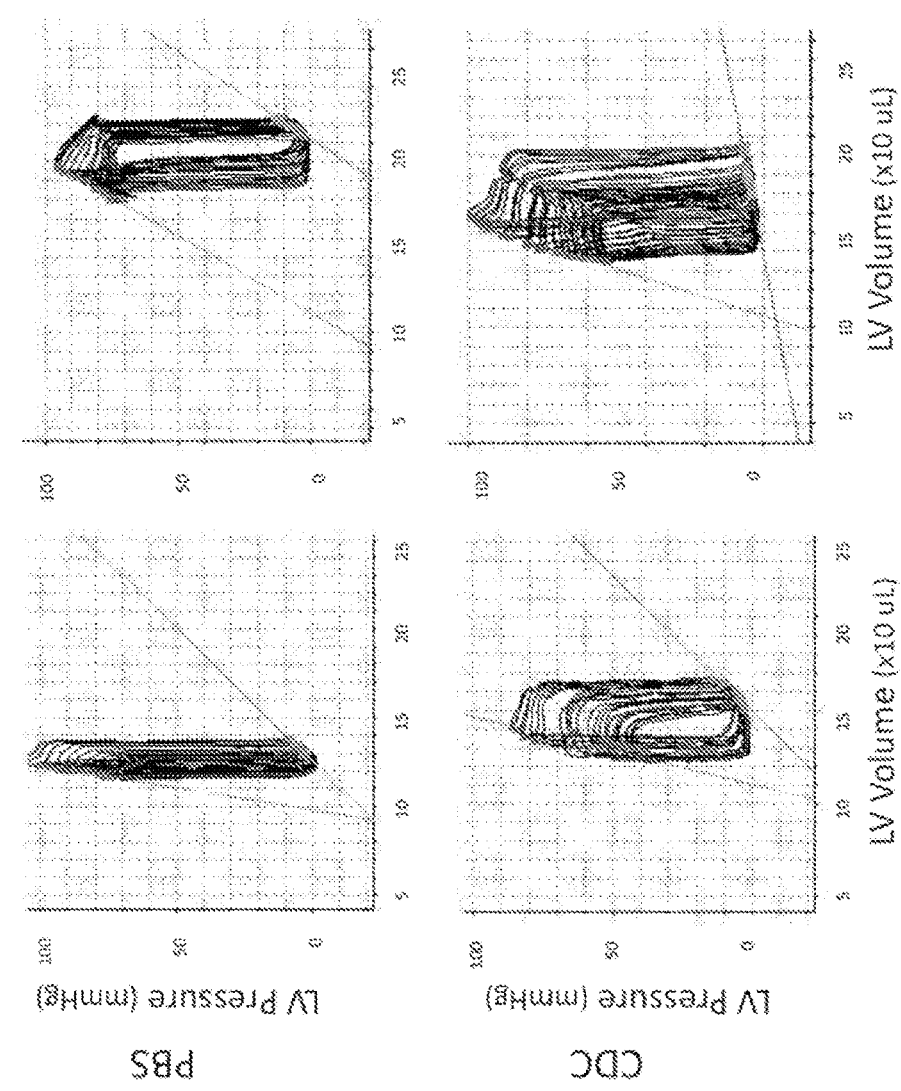
Fig. 13C

Figure 14.
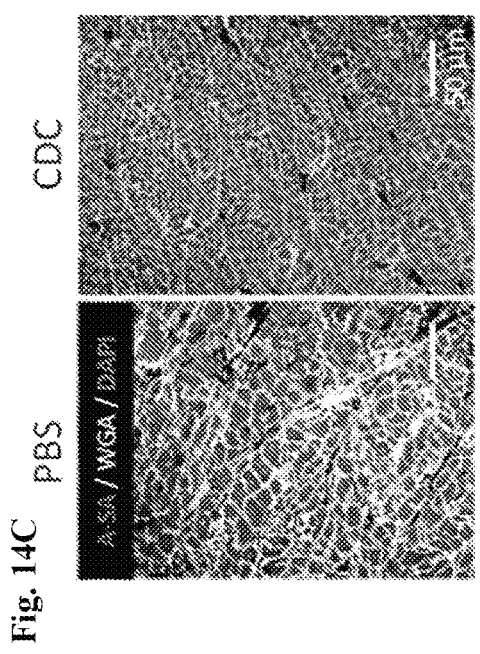
Fig. 14A
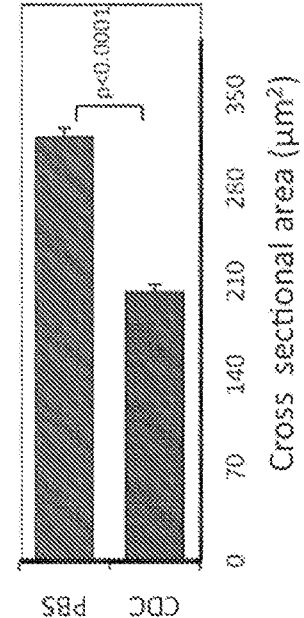
Fig. 14C
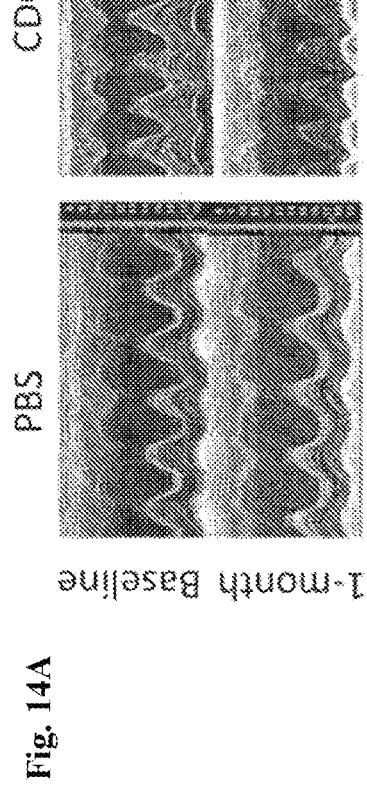
Fig. 14B
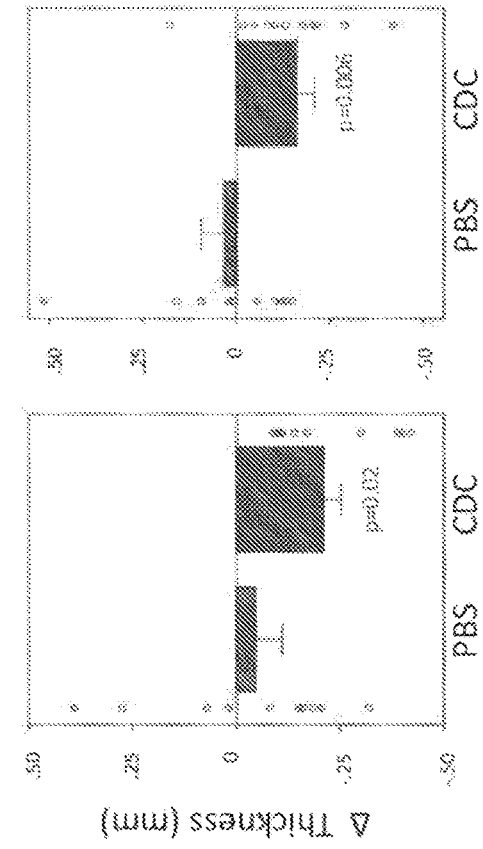
Fig. 14D

Figure 14.
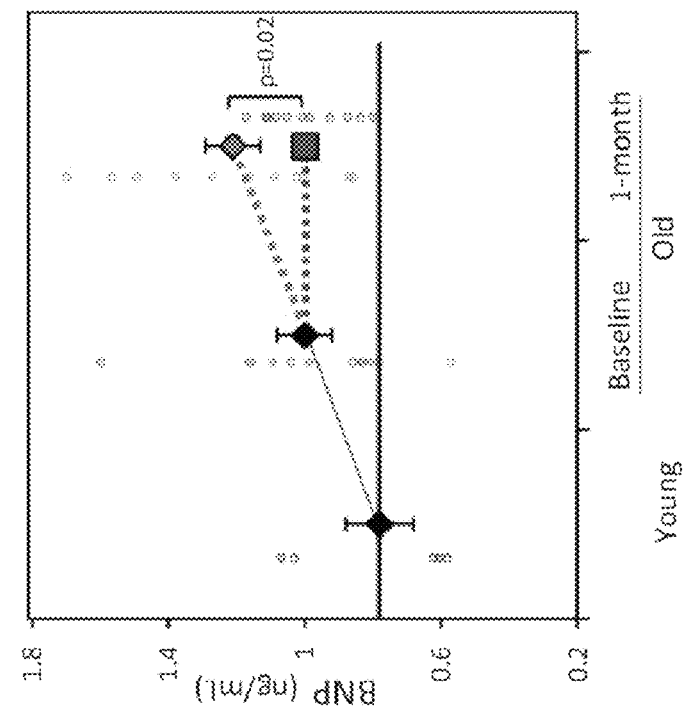
Fig. 14G
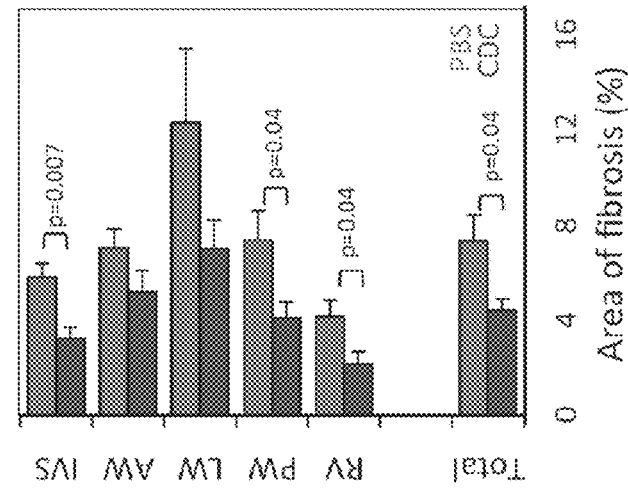
Fig. 14F
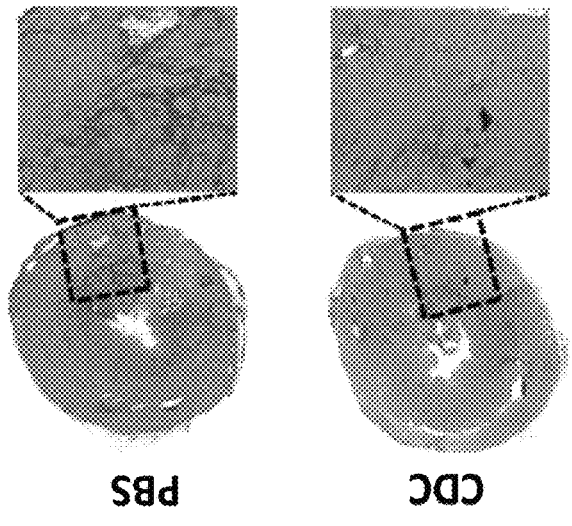
Fig. 14E

Figure 15.
Fig. 15A
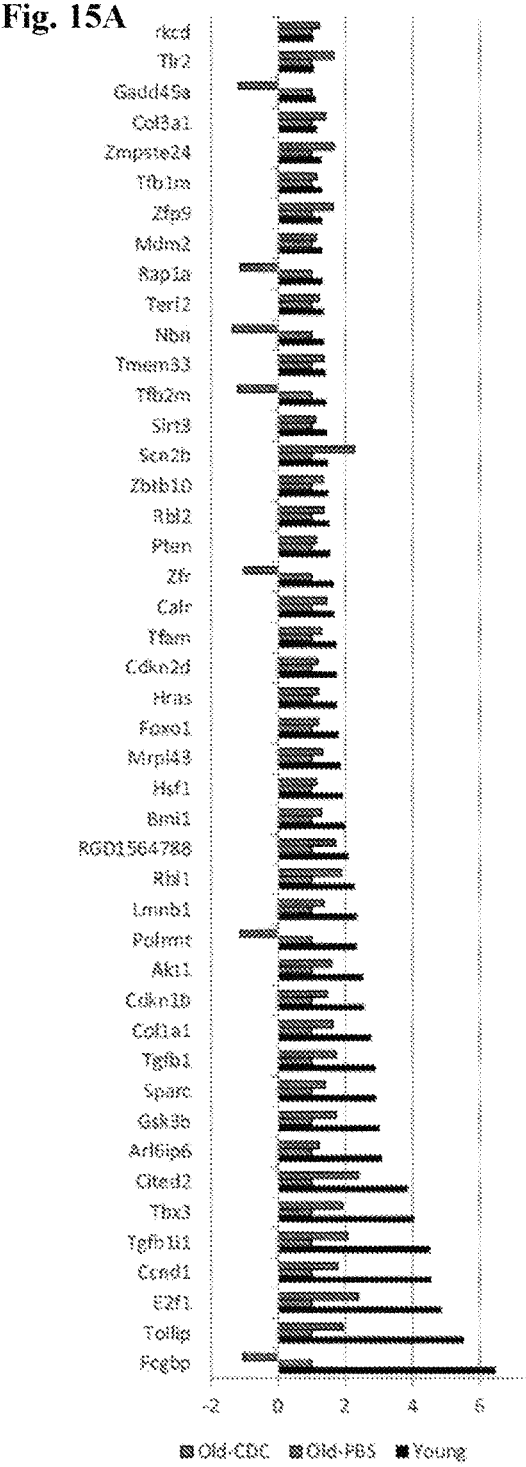
Fig. 15B
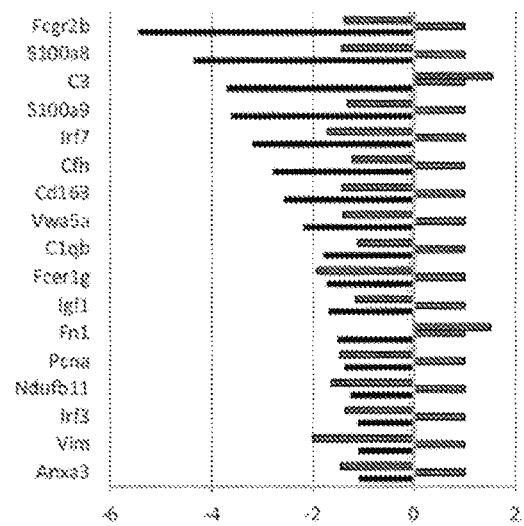
Fig. 15C
Fig. 15D
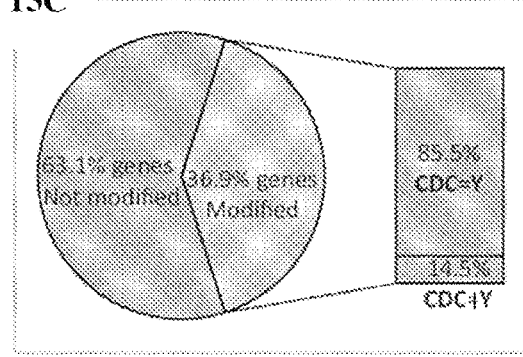

Figure 17.
Fig. 17A
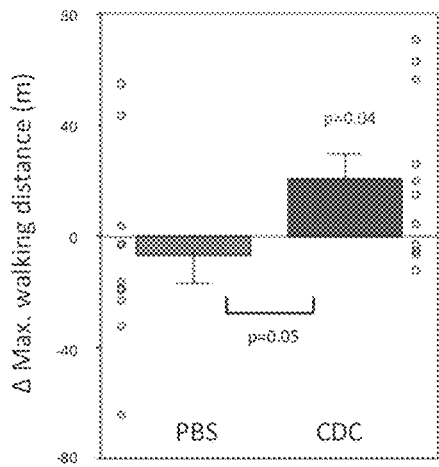
Fig. 17C
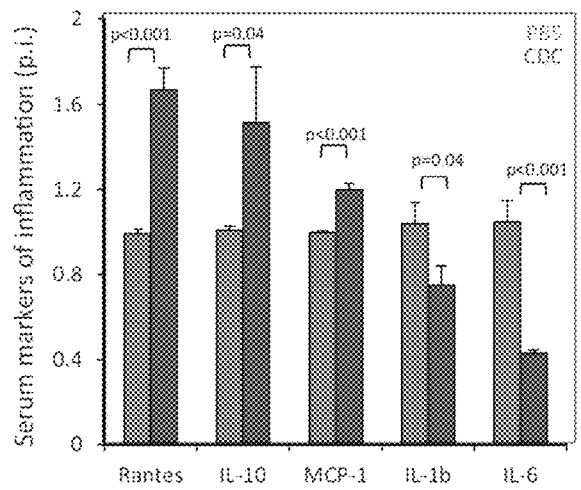
Fig. 17B
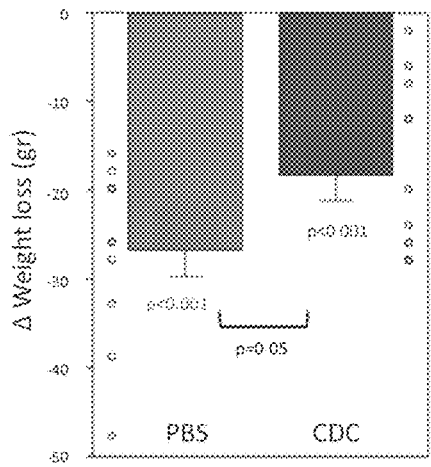
Fig. 17D
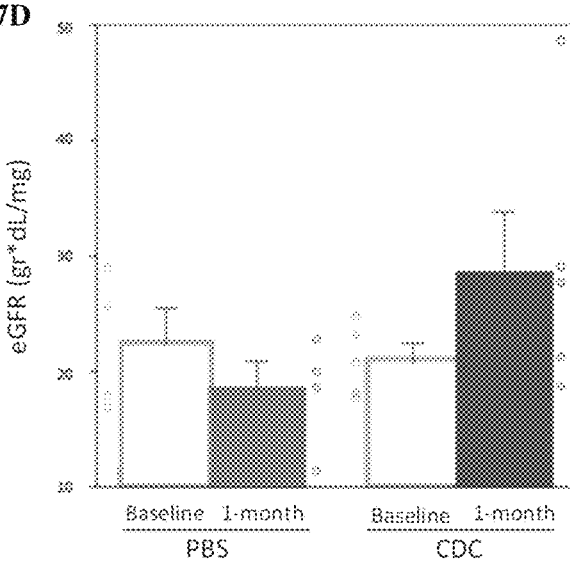
Fig. 17E
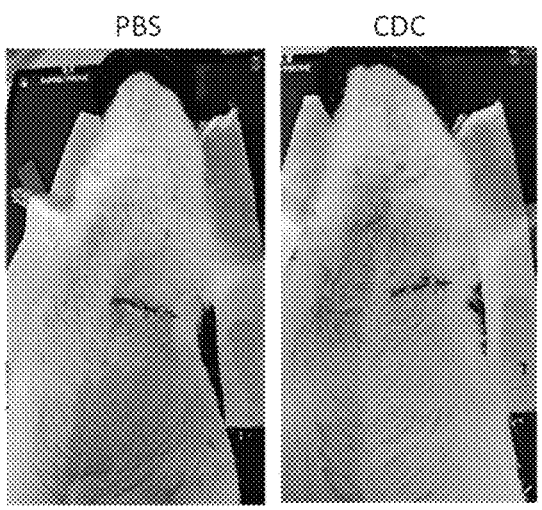
Fig. 17F
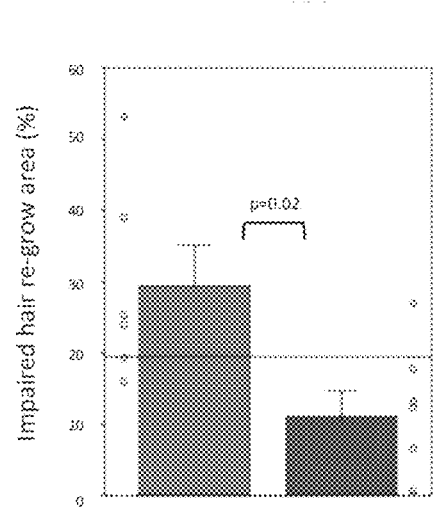

Figure 18.
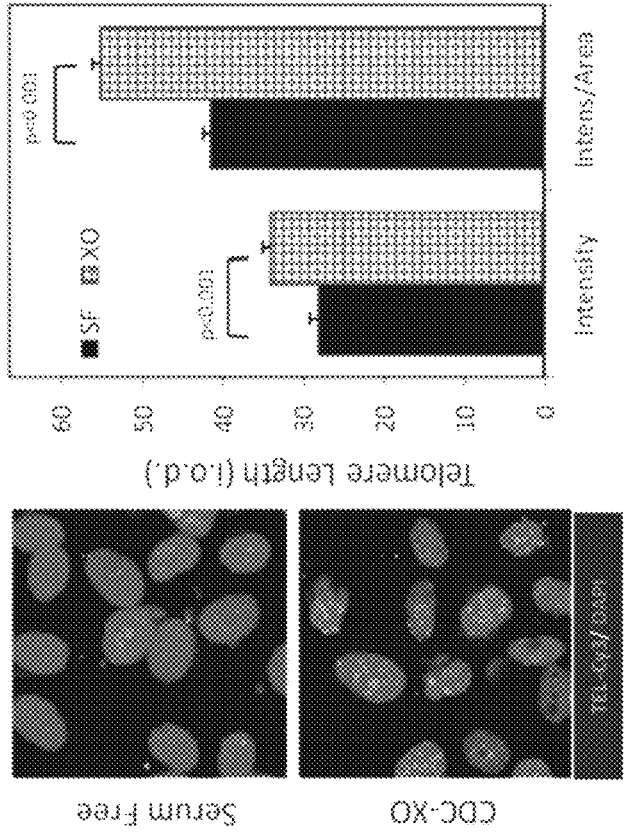
Fig. 18A
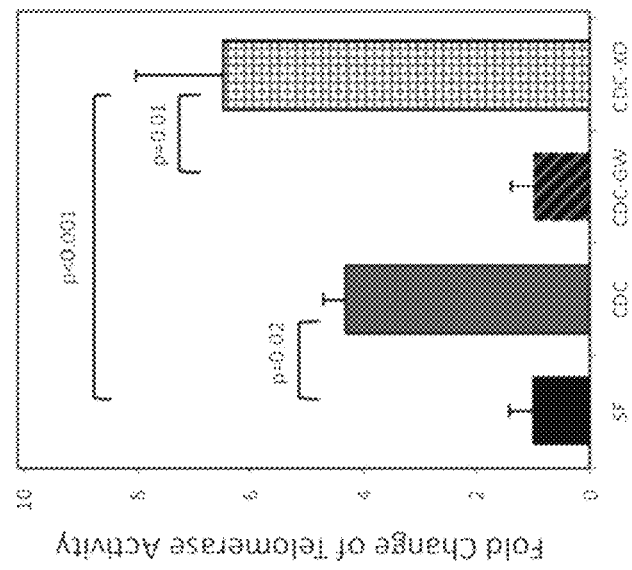
Fig. 18B
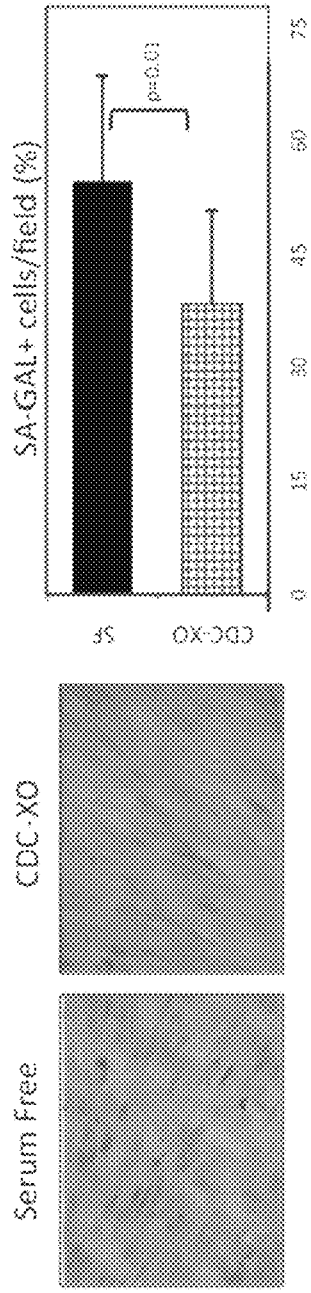
Fig. 18C

Figure 20.
Fig. 20A
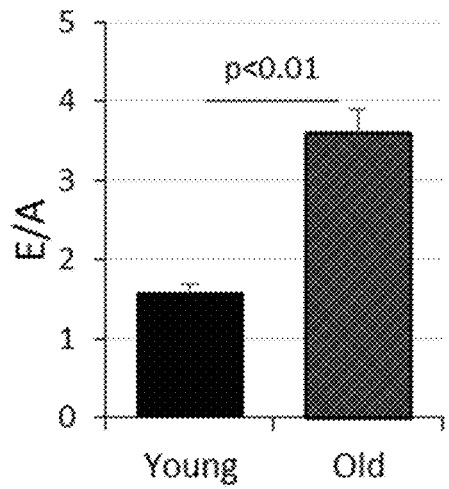
Fig. 20D
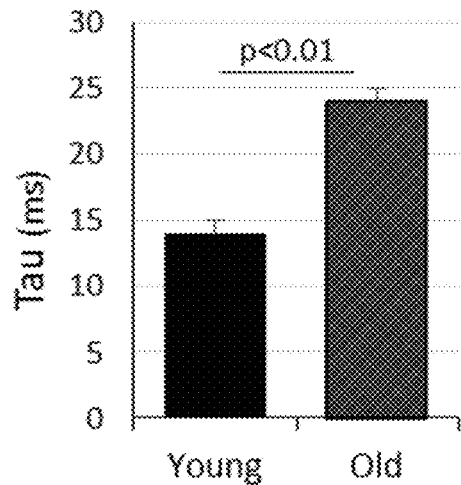
Fig. 20B
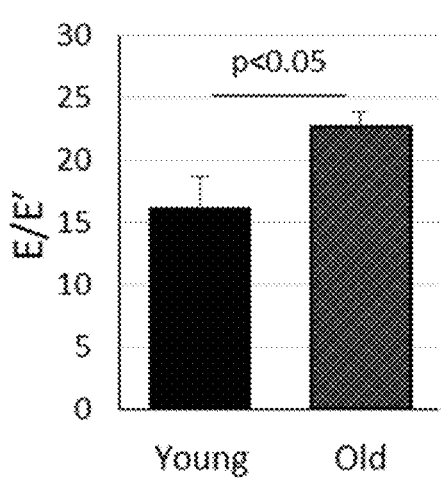
Fig. 20E
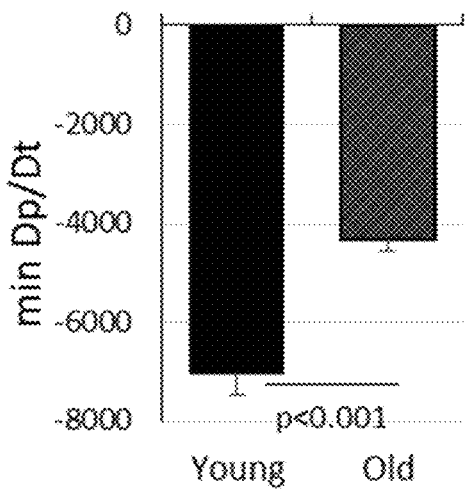
Fig. 20C
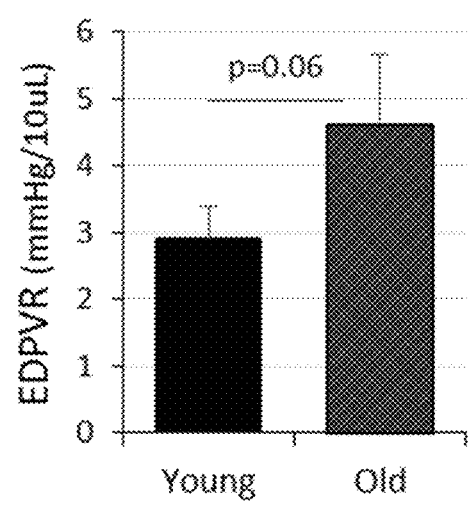
Fig. 20F
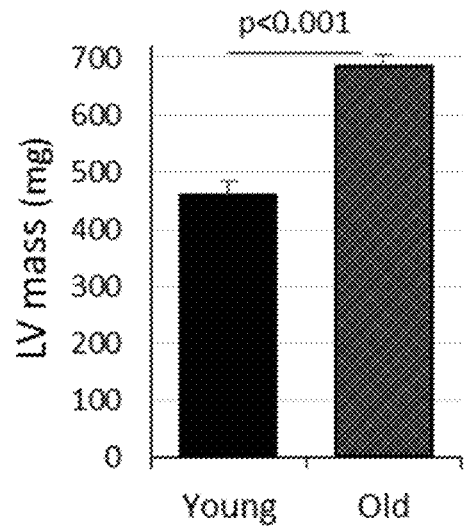

Figure 20.
Fig. 20G
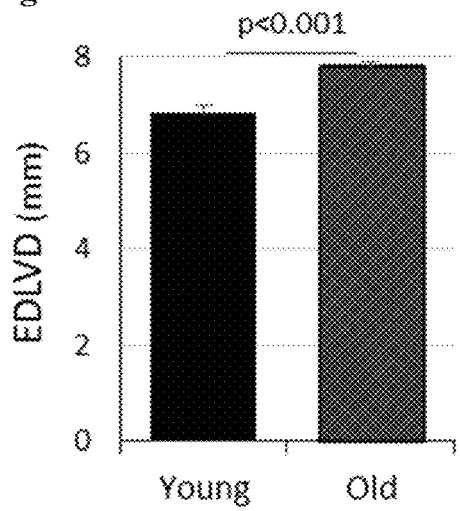
Fig. 20J
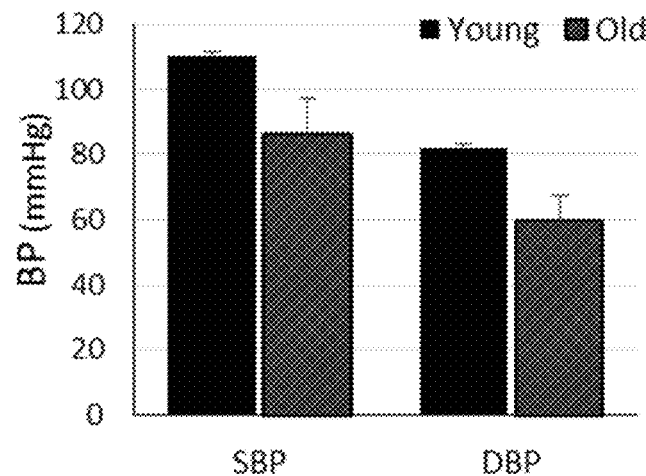
Fig. 20H
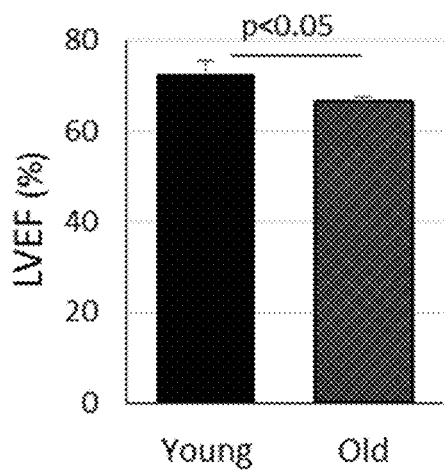
Fig. 20K
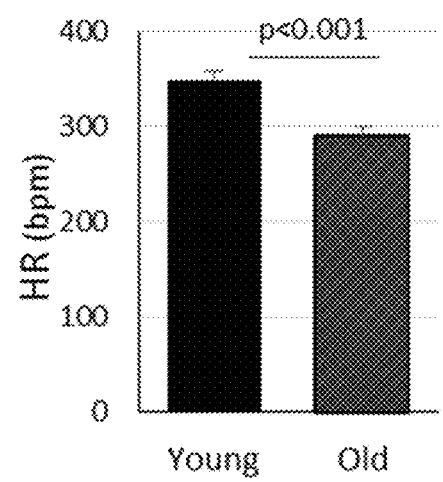
Fig. 20I
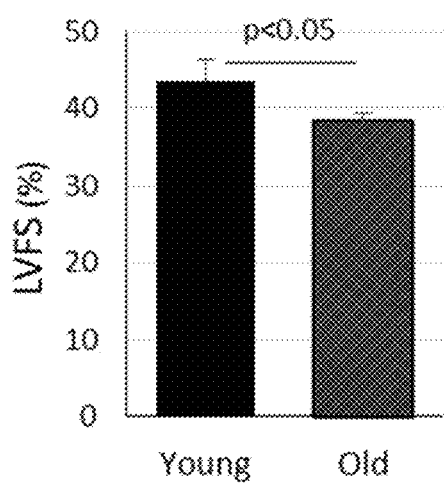
Fig. 20L
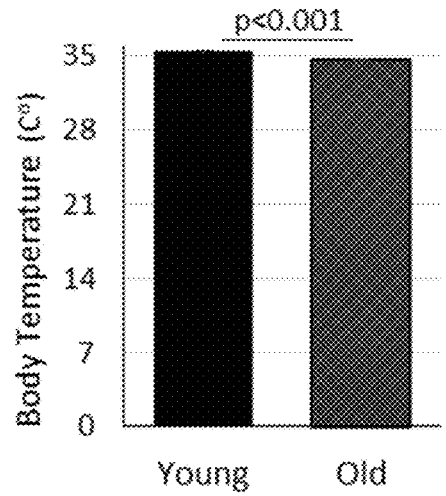

| | Regression Coeff. | p-value |
|---|---|---|
| E/A | | <0.01 |
| E/E' | | <0.05 |
| EDPVR | | n.s. |
| Tau | | 0.01 |
| Min Dp/Dt | | 0.001 |
| LV mass | | 0.001 |
| EDLVD | | 0.01 |
| LVEF | | n.s. |
| LVFS | | n.s. |
| SBP | | n.s. |
| HR | | 0.01 |
| Temperature | | 0.001 |
| Distance | | 0.01 |

Figure 22.
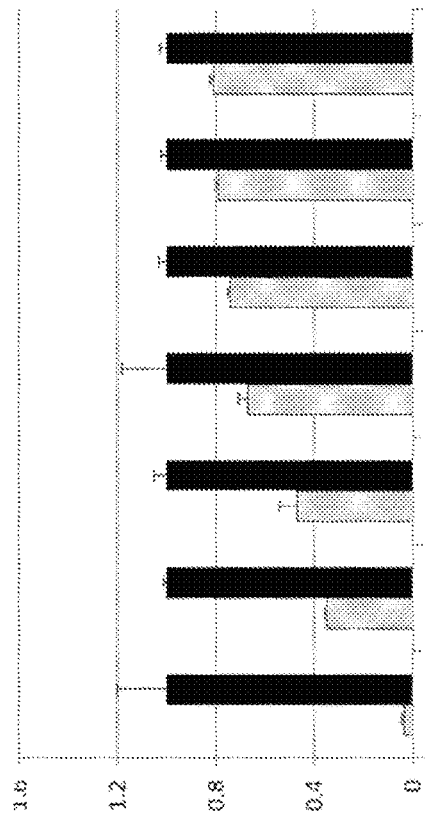
Fig. 22A
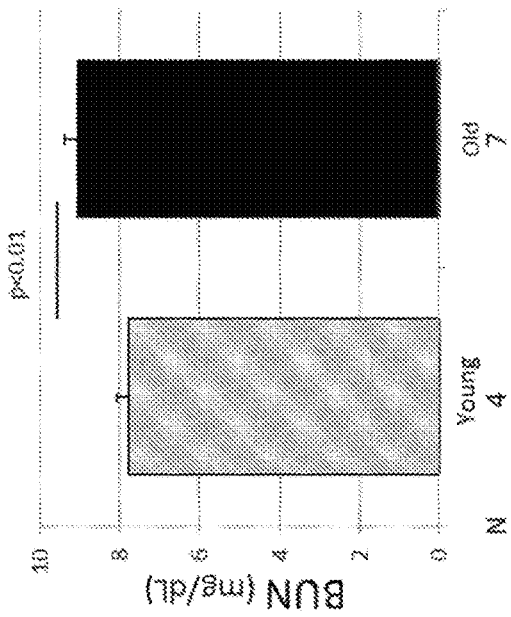
Fig. 22B
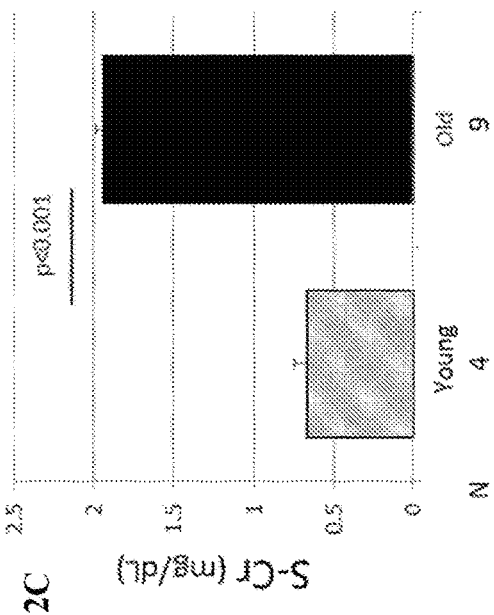
Fig. 22C
Fig. 22D Figure 23.
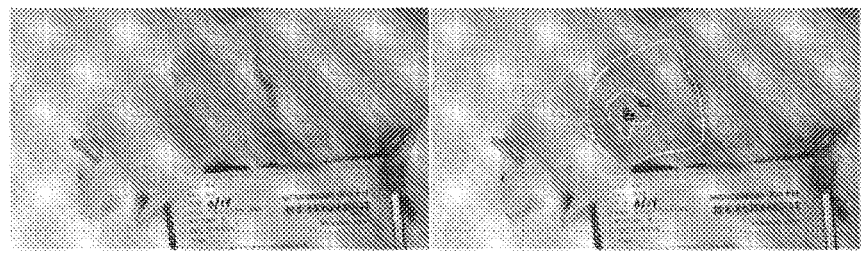
Fig. 23C
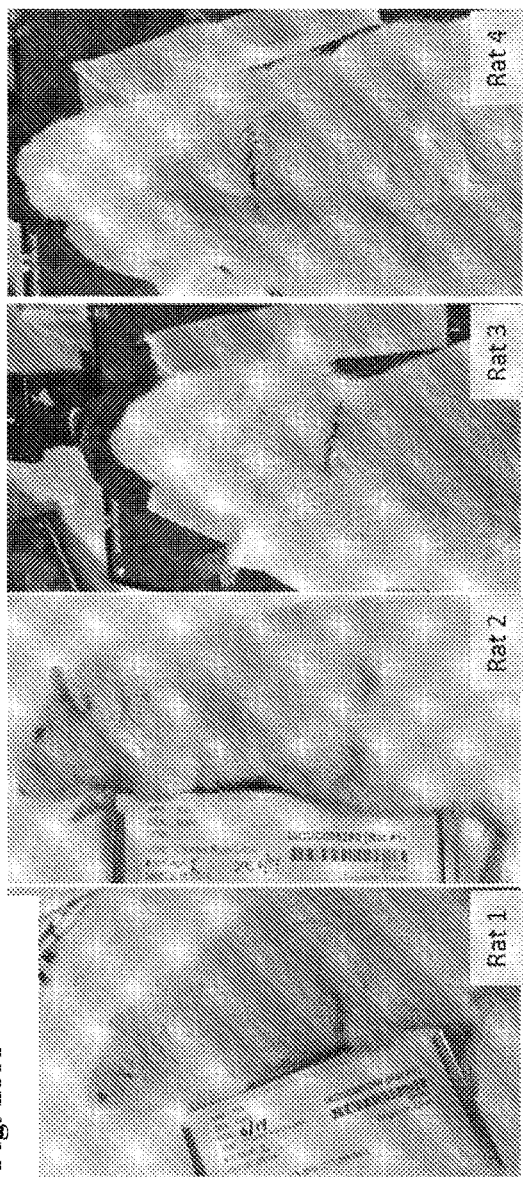
Fig. 23A
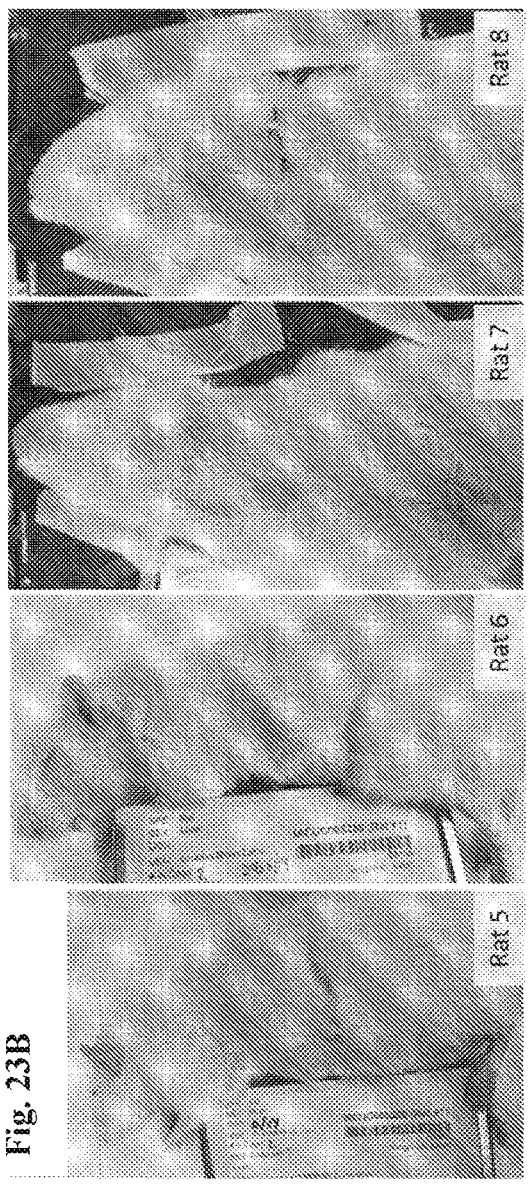
Fig. 23B

Figure 25.
Fig. 25A
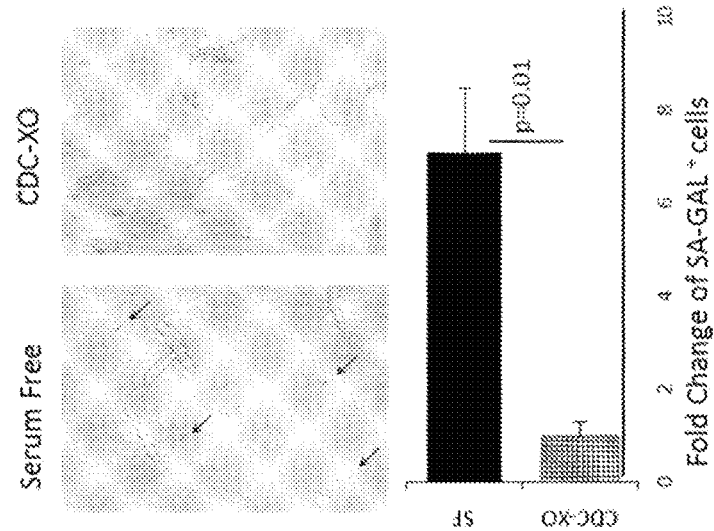
Fig. 25B
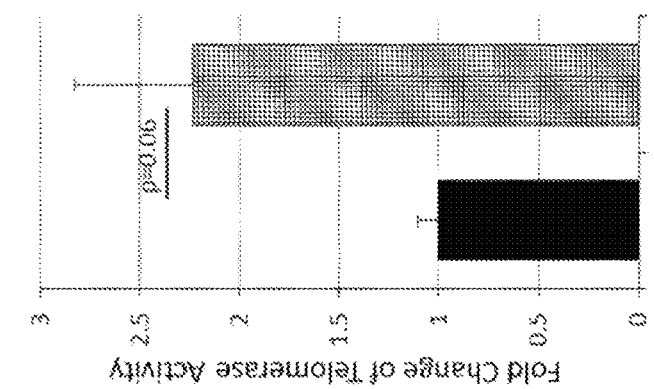
Fig. 25C
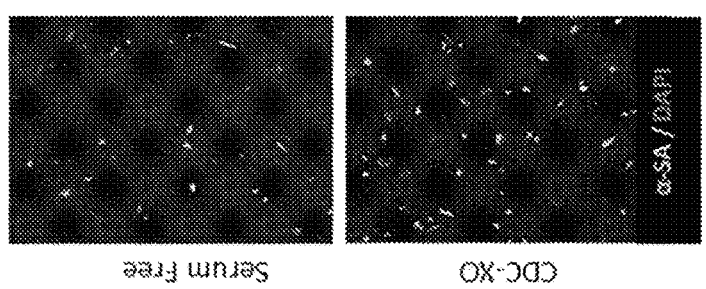
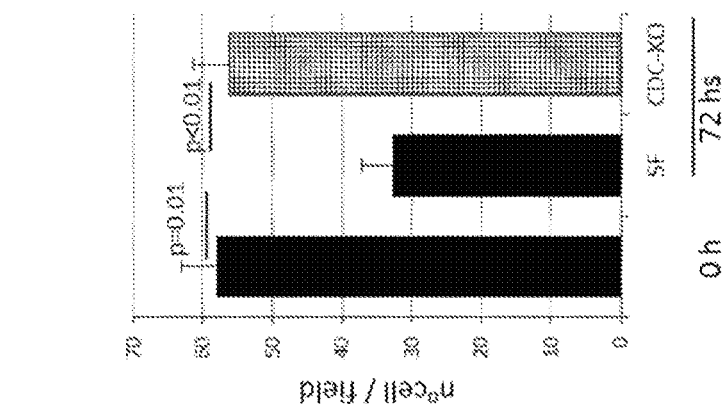

Figure 26.
Fig. 26C
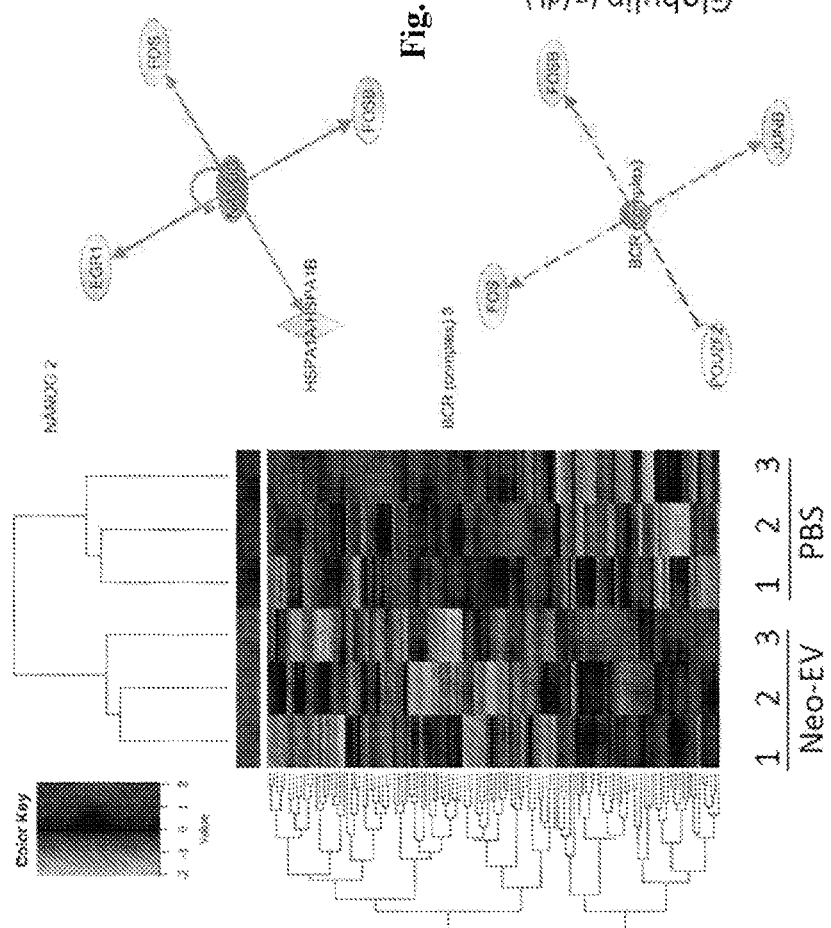
Fig. 26D
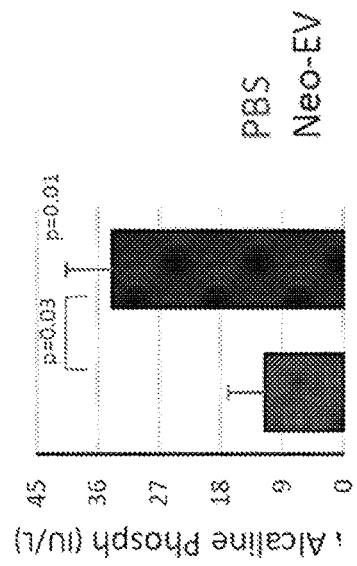
Fig. 26E
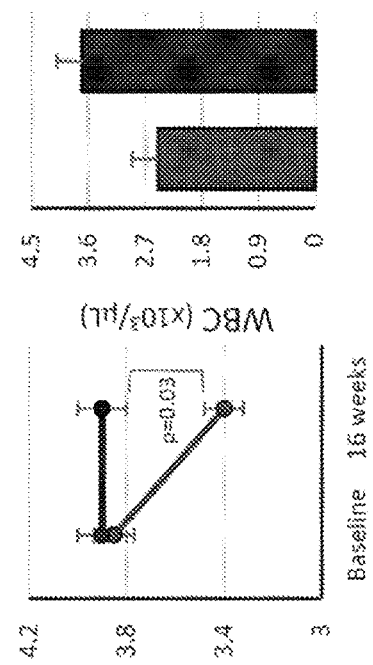

Figure 28.
Figure 28D.
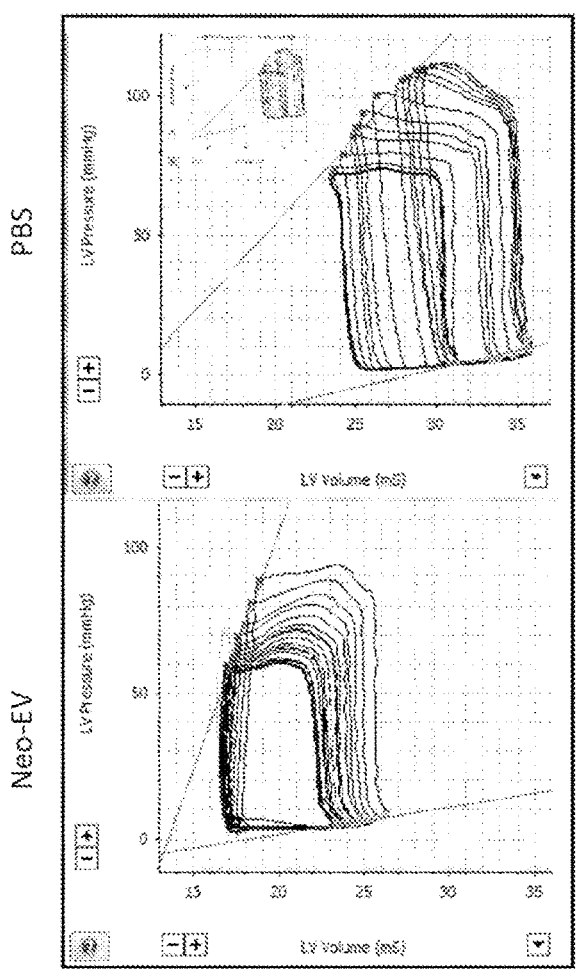
Figure 28E.
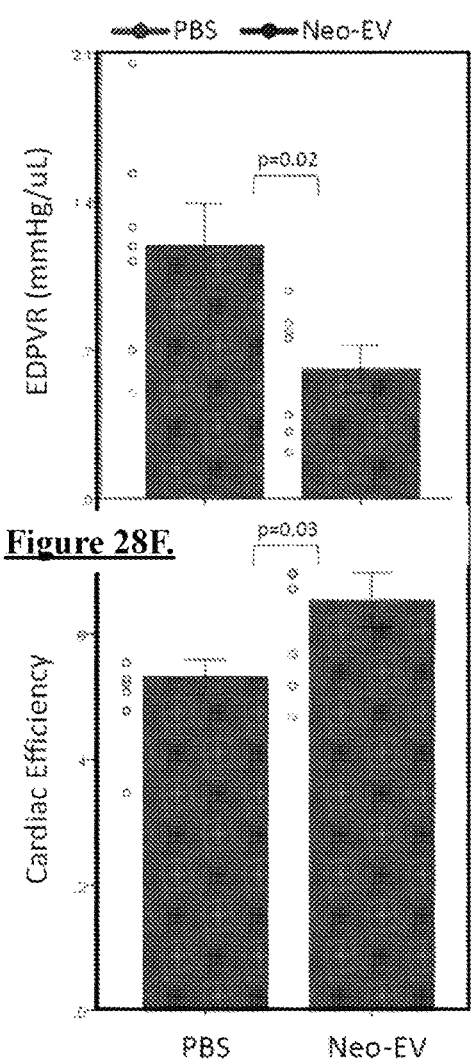
Figure 28F.

Figure 29.
Fig. 29A
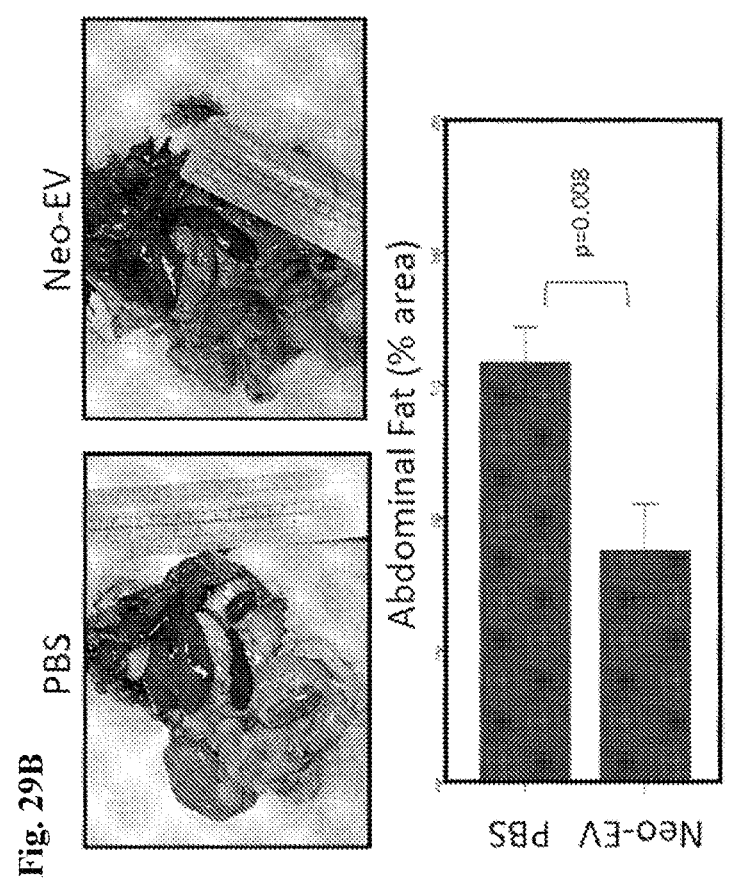
Fig. 29B
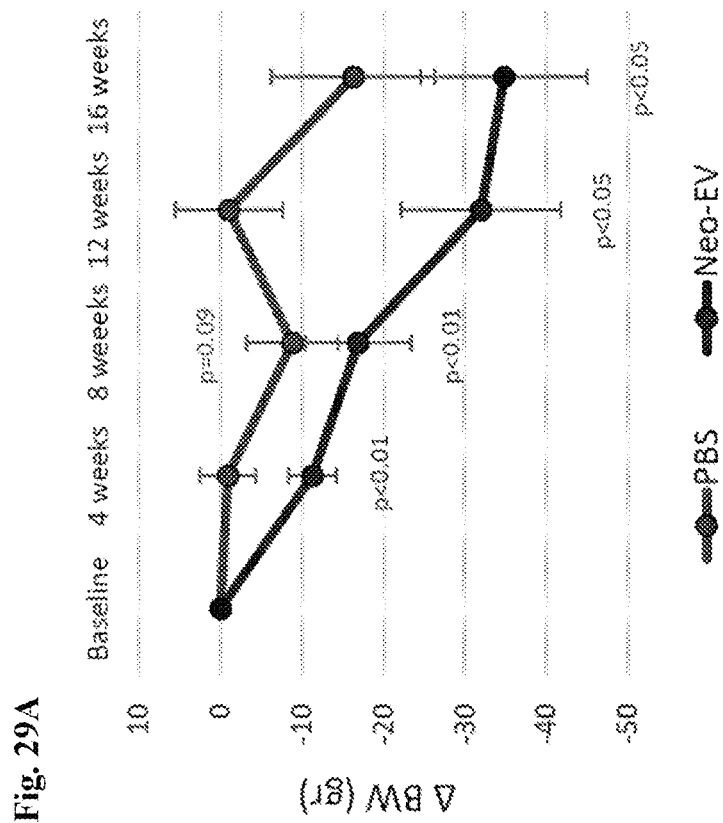

Figure 30.

CARDIOSPHERE-DERIVED CELLS AND THEIR EXTRACELLULAR VESICLES TO RETARD OR REVERSE AGING AND AGE-RELATED DISORDERS

CROSS REFERENCE TO RELATED APPLICATIONS

This application is the U.S. National Phase of International Application PCT/US2017/052350, filed Sep. 19, 2017, which claims the benefit of priority to U.S. Provisional Application No. 62/397,061, filed Sep. 20, 2016. All of the foregoing applications are fully incorporated herein by reference in their entireties for all purposes.

STATEMENT REGARDING FEDERALLY-SPONSORED RESEARCH

This invention was made with government support under HL124074 awarded by the National Institutes of Health. The government has certain rights in the invention.

FIELD OF THE INVENTION

This invention relates to the use of cells and their extracellular vesicles, specifically cardiosphere-derived cells and their secreted extracellular vesicles, such as exosomes and microvesicles, for achieving cardiac and systematic rejuvenation.

BACKGROUND

Aging is characterized by progressive decline in physiological functions and increase in mortality that is often accompanied by the onset and progression of diseases. Although the underlying molecular mechanisms of aging remain largely elusive, many studies have provided supporting evidence that telomere shortening together with oxidative stress and mitochondrial dysfunction are important factors contributing to the aging process. Cardiovascular disease increases markedly in prevalence with aging, creating a huge economic burden.

As described, cell senescence is tightly connected with the aging process, and is characterized by progressive shortening of telomeres. Critical shortening of these protective 'caps' on the ends of linear chromosomes is associated with heart dysfunction and hypertrophy, impaired cardiomyocyte proliferation, and reduced regenerative capacity. The aged heart exhibits abnormal relaxation and/or increased stiffness, along with interstitial fibrosis and cardiomyocyte hypertrophy. Among rejuvenating strategies tested to date, parabiosis and cellular reprogramming seem promising, but none has addressed age-related heart dysfunction. Thus, there is a great need in the art for methods and compositions related to treating and modulating age-related disorders, including age-related heart dysfunction.

Cardiosphere-derived cells (CDCs) are cells which can differentiate into the three major cell types present in the heart, including cardiomyocytes, endothelial cells, and smooth muscle cells. These cells work primarily indirectly, including through paracrine effects mediated by secretion of extracellular vesicles such as exosomes and microvesicles.

Described herein are methods and compositions for use of cardiosphere-derived cells (CDCs) and their extracellular vesicles, including exosomes and microvesicles, for biological rejuvenation and treatment of age-related disorders. CDCs improve age-related diastolic function and induced systemic functional improvements (notably, increased exercise tolerance) in old animals. Rejuvenating effects were likewise evident in human heart cells from older donors, co-cultured with young CDCs. CDCs and their extracellular vesicles, such as exosomes and microvesicles, open new therapeutic avenues for anti-aging effects and rejuvenation.

SUMMARY OF THE INVENTION

Described herein is a method of treating age-related effects in a subject including administering a composition to a subject, wherein administration of the composition treats age-related effects in the subject. In various embodiments, the In various embodiments, the composition includes cardiosphere-derived cells (CDCs). In various embodiments, the CDCs are from human pediatric subjects. In various embodiments, the composition includes cardiosphere-derived cell (CDC)-derived extracellular vesicles. In various embodiments, the CDC-derived extracellular vesicles are from a human pediatric subject. In various embodiments, age-related effects include one or more disorders of the bone, musculoskeletal, cardiovascular, endocrine, integumentary, nervous, lymphatic, respiratory, circulatory, digestive and urinary system. In various embodiments, the composition is capable of reducing senescence-associated beta-galactosidase (SA-β-GAL) expressing senescent cells. In various embodiments, the composition is capable of increasing expression of telomerase reverse transcriptase (TERT). In various embodiments, the composition is capable of increasing telomerase (TASE) activity. In various embodiments, the composition is capable of maintaining or extending telomere length. In various embodiments, the composition is capable of reducing serum marker levels. In various embodiments, the serum markers include one or more of: brain natriuretic peptide (BNP), creatinine, C-reactive protein (CRP), IL-1b, and IL-6. In various embodiments, administration of the composition includes intramyocardial or intraventricular injection.

Further described herein is a method of modulating age-related effects in a subject including administering a composition to a subject, wherein administration of the composition modulates age-related effects in the subject. In various embodiments, the composition includes cardiosphere-derived cells (CDCs). In various embodiments, the CDCs are from human pediatric subjects. In various embodiments, the composition includes cardiosphere-derived cell (CDC)-derived extracellular vesicles. In various embodiments, the CDC-derived extracellular vesicles are from human pediatric subjects. In various embodiments, age-related effects include one or more of: osteoporosis, Alzheimer's disease or other types of dementia, immune senescence, wrinkled skin, arthritis, and type 2 diabetes. In various embodiments, age-related effects include one or more of: cardiomyopathies, atherosclerosis, coronary artery disease, and diastolic dysfunction. In various embodiments, age-related effects include one or more of: hair loss, frailty, age-related cognitive decline, age-related sexual dysfunction, and progeria.

BRIEF DESCRIPTION OF FIGURES

FIG. 2. CDC-derived exosome-mediated protection of telomerase-telomere axis. FIG. 2A. Telomerase activity in extracts of heart explant-derived cells from old human donors after 96 hours was determined following telomeric repeat amplification protocol (TRAP) in four groups: the control group incubated with serum-free media (SF); cells co-cultured with young donor CDC alone or together with GW4869 inhibitor of exosome release (CDC and CDC-GW4869, respectively), using transwell membranes; cells co-cultured with young CDC-derived exosomes resuspended in serum-free media. FIG. 2B. Representative images of cells subjected to telomere Q-FISH analysis. Nuclei are stained with DAPI and telomeres with specific CY3-labeled probe (red). Telomere length was analyzed by measuring the integrated optical density (i.o.d.) of the Cy3-channel within the nuclear borders after subtracting the background i.o.d. Results adjusted to the nuclear area are presented as well. Rejuvenation of heart explant-derived cells from old human donors with young human donor CDC-derived exosomes. FIG. 2C. Histochemistry for senescence-associated β-galactosidase (SA-GAL) (blue). Proportion of senescent, SA-GAL+ cells after 96 hours co-incubation time period with young CDC-derived exosomes (CDC-derived exosomes) or serum-free media (SF). CDC-derived exosomes increased the self-assembly potential of the old human heart explant-derived cells. Plated at the same number on day-0, heart explant-derived cells from an old human donor were treated with young CDC-derived exosomes or serum-free (SF) media on day-1. After an additional 72 hours (day-4), cells were collected and quantified, observing higher number of cells in the CDC-derived exosomes treated group, followed by their resuspension at a density of $3 \times 10^4$ cells/ml in a serum-free media in ultra-low attachment dishes. Newly formed cardiospheres' concentration and size were measured after 72 hours. FIG. 2D. Representative images of formed cardiospheres after 3 days. Concentration of cardiospheres in both groups. Normalized differences in the concentration of the biggest cardiospheres between young CDC-derived exosomes and SF-treated groups. Data are mean±SEM. The lowest number of replicates per experiment was three.

FIG. 3A. Histochemistry for senescence-associated β-galactosidase (SA-GAL) (blue) after 72 hours. Importantly, senescent, SA-GAL+ cells were found among the non-cardiomyocyte population of cells. The proportion of SA-GAL+ cells was significantly lower in the CDC-derived exosomes treated cells compared with control group. FIG. 3B. Immunofluorescence for telomerase reverse transcriptase (TERT) (green), DAPI (blue). TERT protein levels were higher in the CDC-derived exosomes treated cells after 72 hours in both (α-SA+ and α-SA−) types of cells. FIG. 3C. Telomerase activity in extracts of a whole population of cells was determined following the telomeric repeat amplification protocol, after 72-hours. CDC-derived exosomes treated cells presented a 2 fold increase of telomerase activity. CDC-derived exosomes increase the long-term survival of old rat cardiomyocytes in culture.

E/A: early to late ventricular filling velocity ratio, determined by Doppler echocardiography of the transmitral flow.

E/E': the ratio of early mitral inflow velocity to early diastolic velocity of the mitral annulus, determined by echo-Doppler of transmitral flow and tissue Doppler of mitral annulus.

EDPVR: End-diastolic pressure-volume relationship of the LV, determined with the pressure-volume transducer placed inside the LV cavity, during vena cava gradual compression.

Tau: exponential decay of the left ventricular pressure during isovolumetric relaxation.

Min Dp/Dt: minimum rate of pressure change in the LV.

LV mass: echo-based LV mass estimation.

EDLVD: LV end-diastolic diameter, measured by echo in M-Mode

LV FS: LV fractional shortening, determined by echo.

Figure 5A:
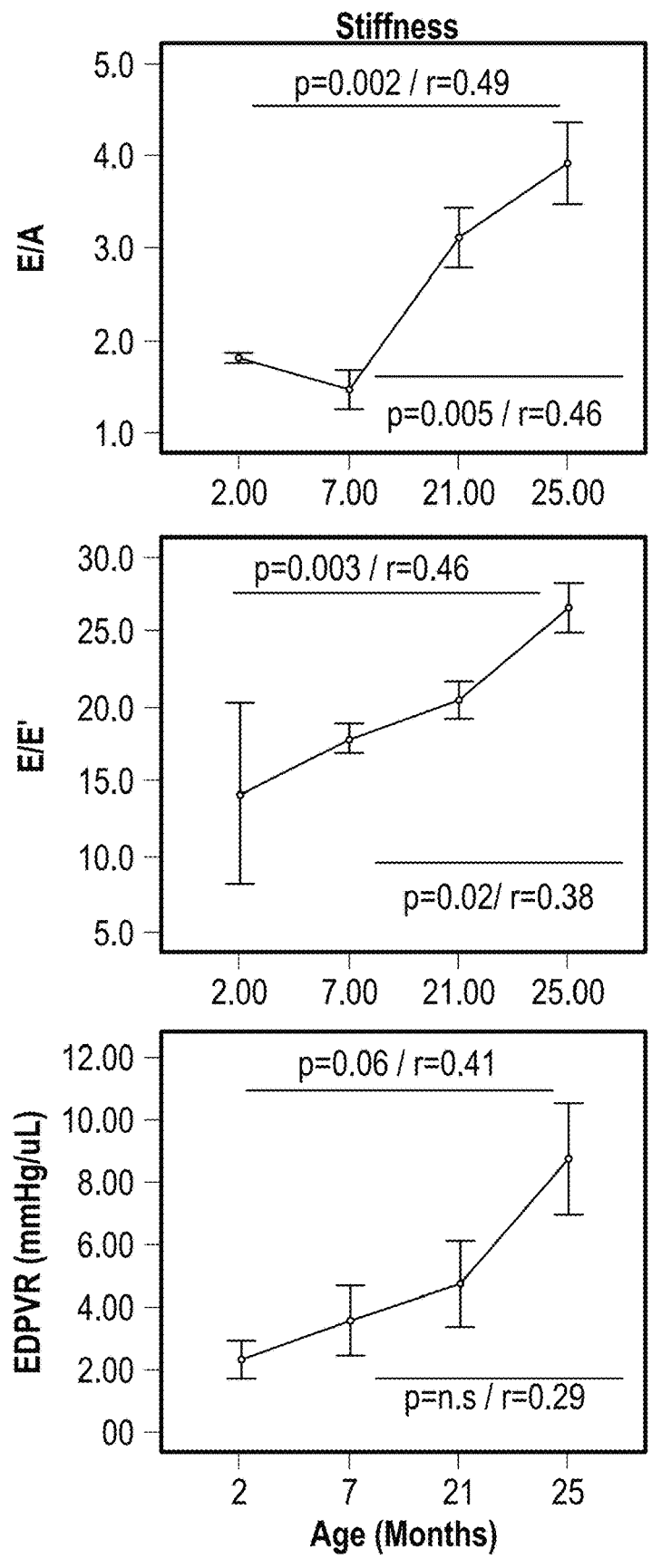
FIG. 5. Old Fisher 344 rats represent a good model of age-related diastolic dysfunction. Echocardiographic and hemodynamic parameters related with diastolic function (both left ventricular (LV) stiffness and relaxation), and LV structure are presented for rats in different age groups: 2-months (n=5), 7-months (n=5), 21-months (n=20) and 25-months old (n=5). Results indicate a gradual and steady impairment of LV diastolic function after adulthood, associated with increase of the LV mass and end-diastolic diameter. Systolic function remains unchanged after 7-months.
Figure 5B:
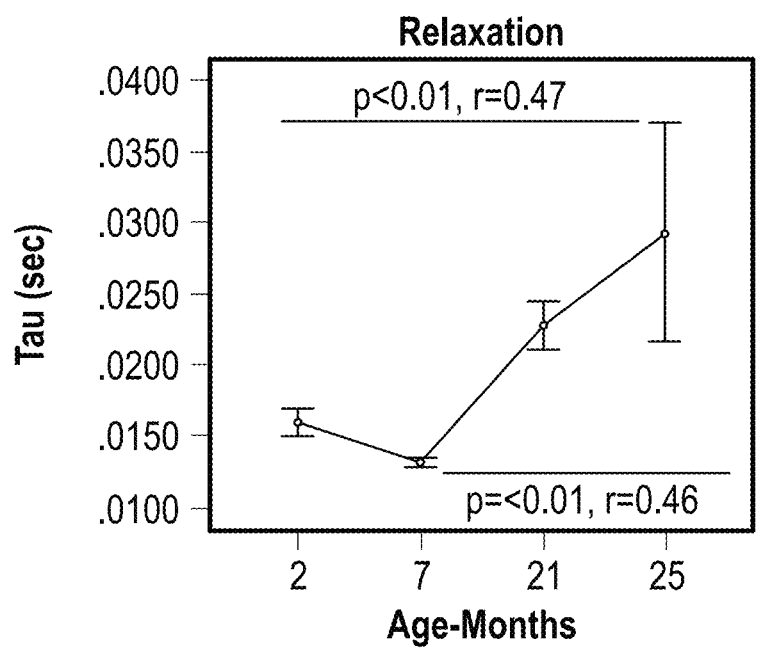
Figure 5B:
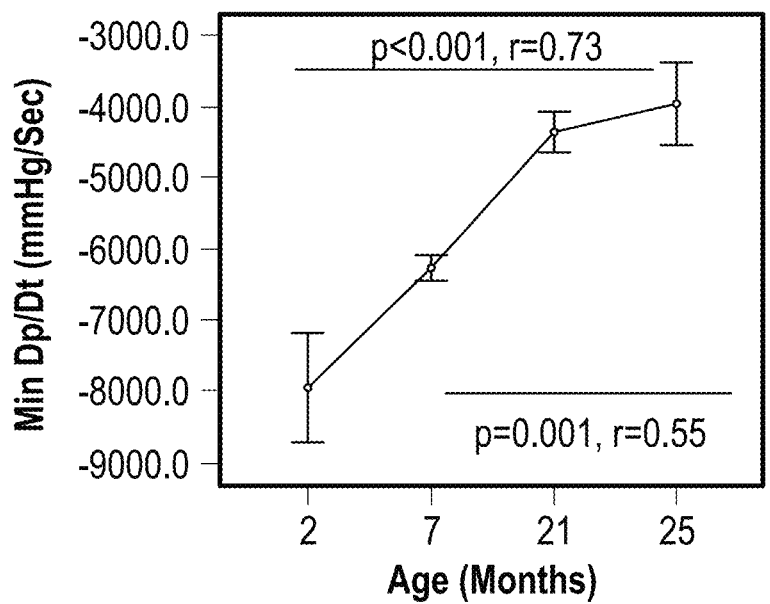
Figure 5C:
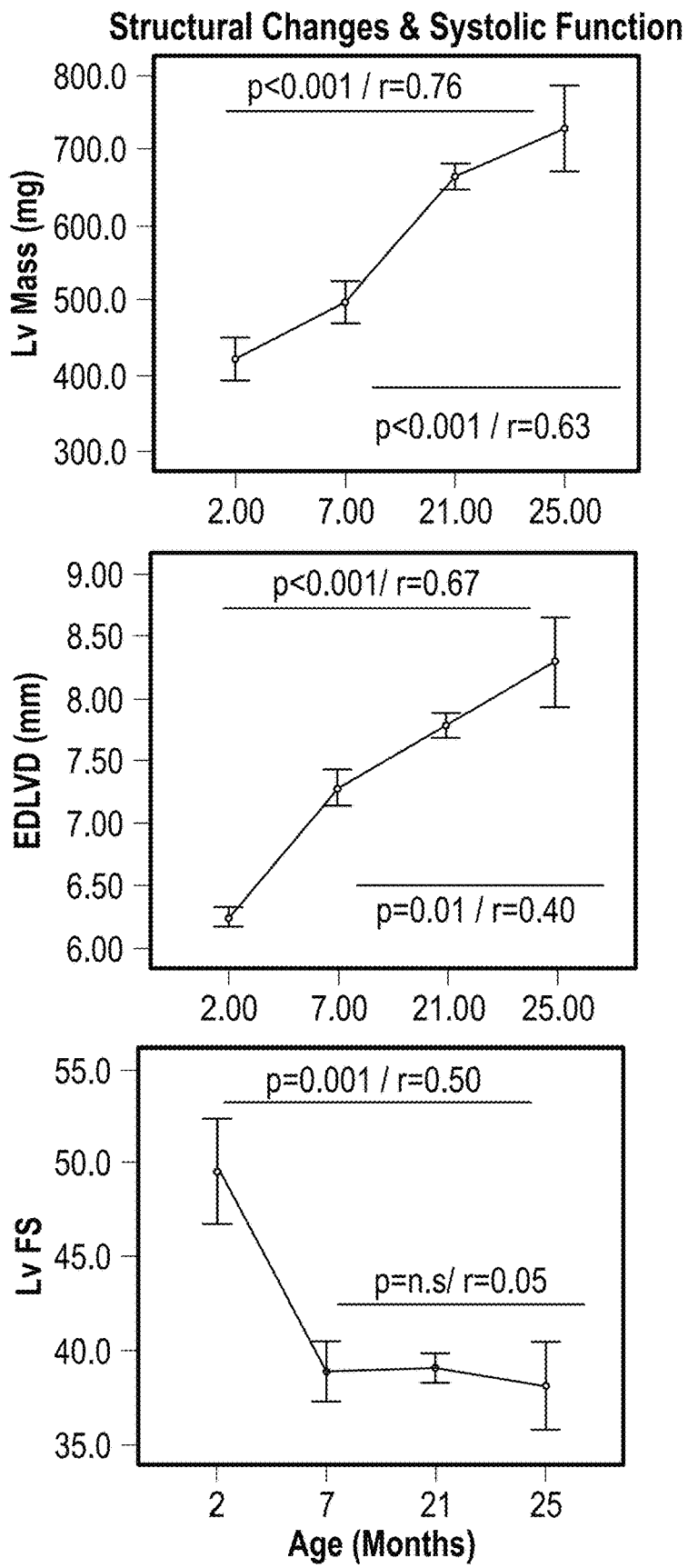
Figure 5D:
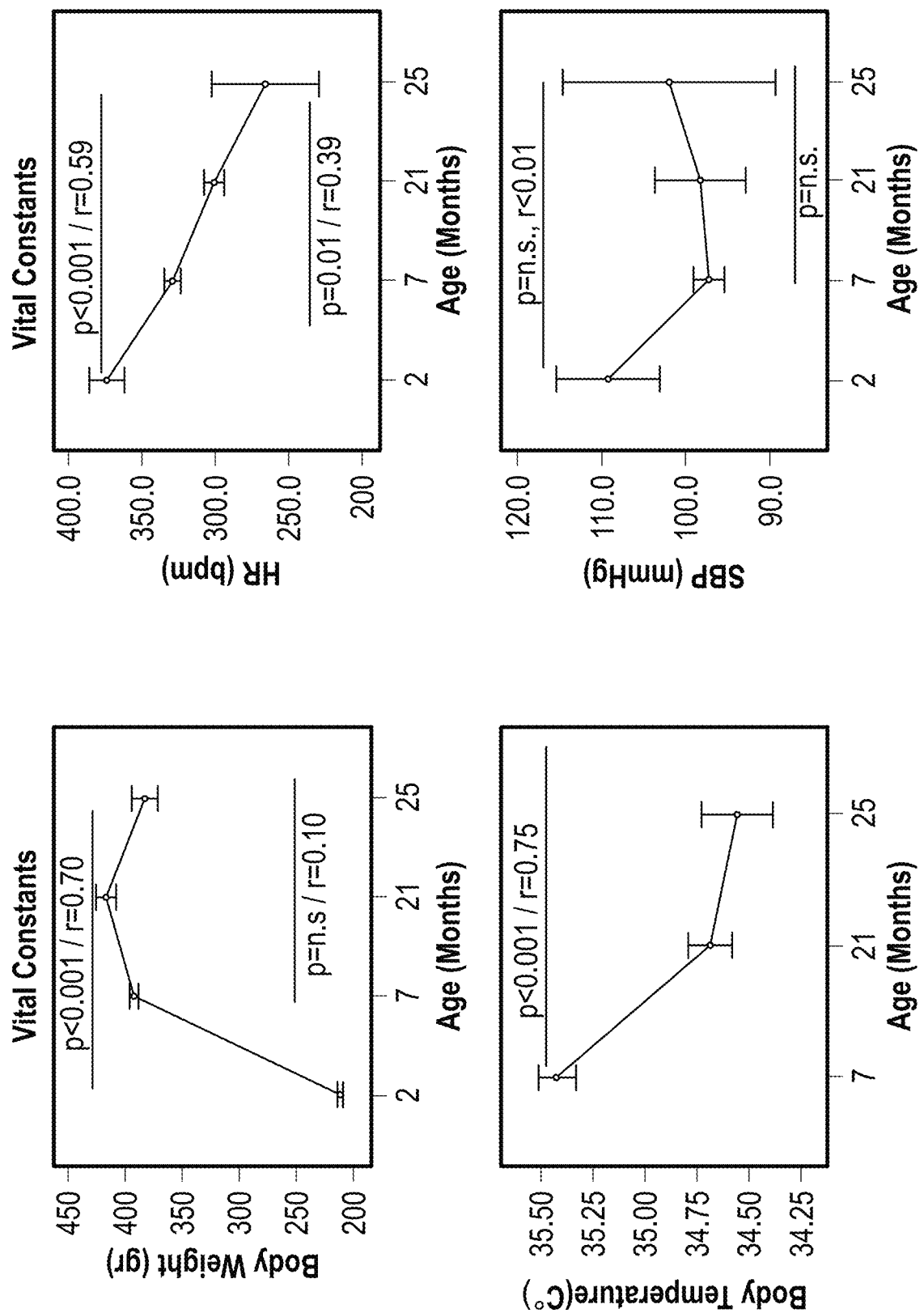
Figure 5E:
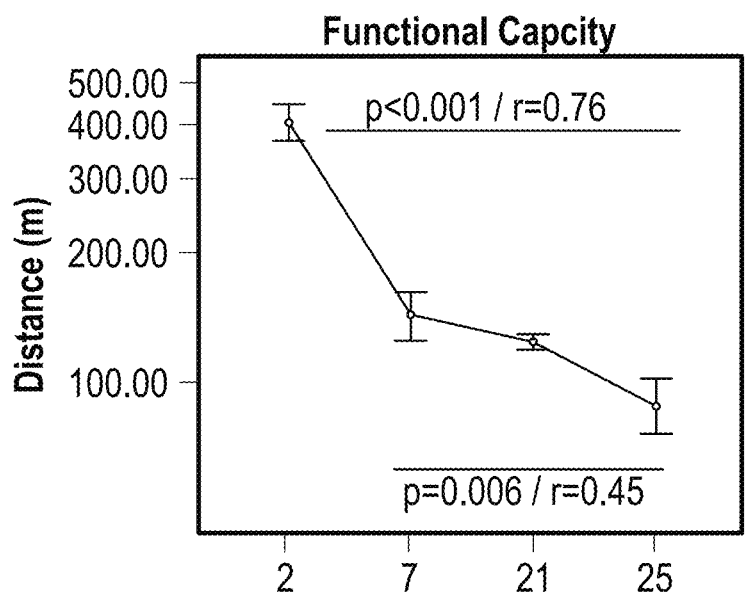
Figure 5E:
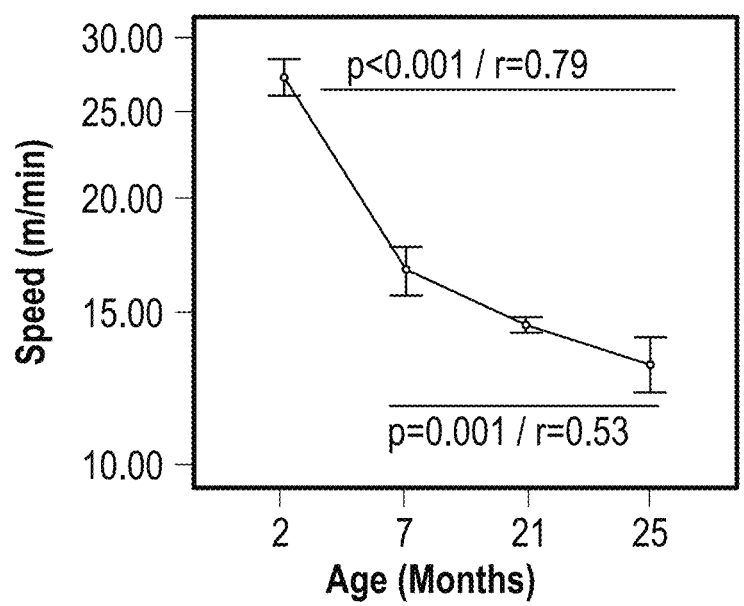

Statistical analysis: lineal regression results are reported. At the top—comparison between all age-groups. At the bottom—comparison between 7-months old with older animal groups. Old animals present significant differences in vital constants and functional capacity, including FIG. 5A stiffness, FIG. 5B relaxation, FIG. 5C structural changes and systolic function, FIG. 5D vital constants, and FIG. 5E functional capacity. Data are presented for rats in different age groups: 2-months (n=5), 7-months (n=5), 21-months (n=20) and 25-months old (n=5). Functional Capacity was evaluated with exercise treadmill test. Functional capacity of old rats is dramatically impaired. Distance and speed refer to the maximum achieved by the animals on the treadmill.

HR: heart rate during invasive hemodynamic procedure.
SBP: systolic blood pressure during invasive hemodynamic procedure.
Statistical analysis: lineal regression results are reported. At the top—comparison between all age-groups. At the bottom—comparison between 7-months old with older animal groups.

Figures 6, 6A:
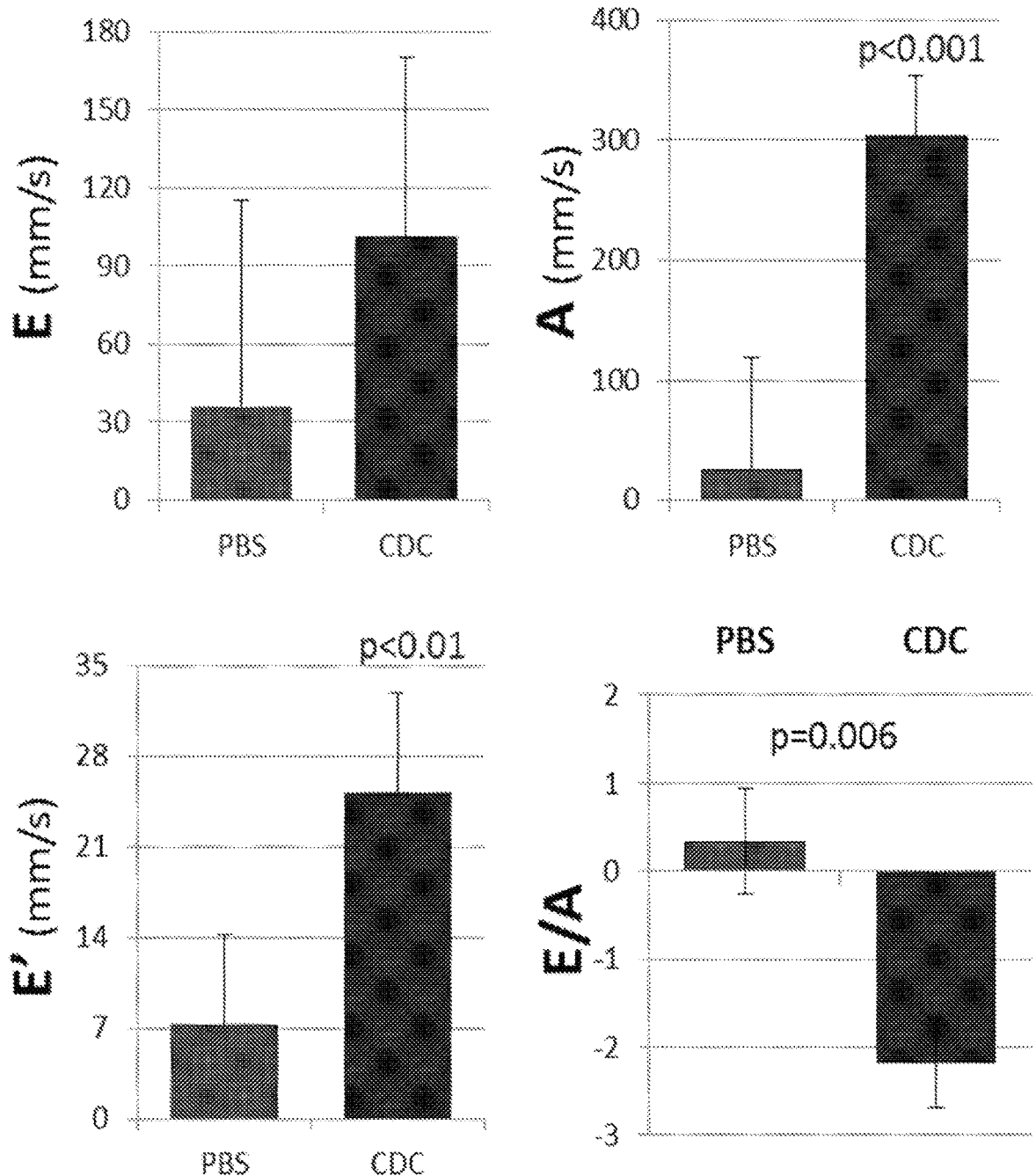
Figures 6, 6B:
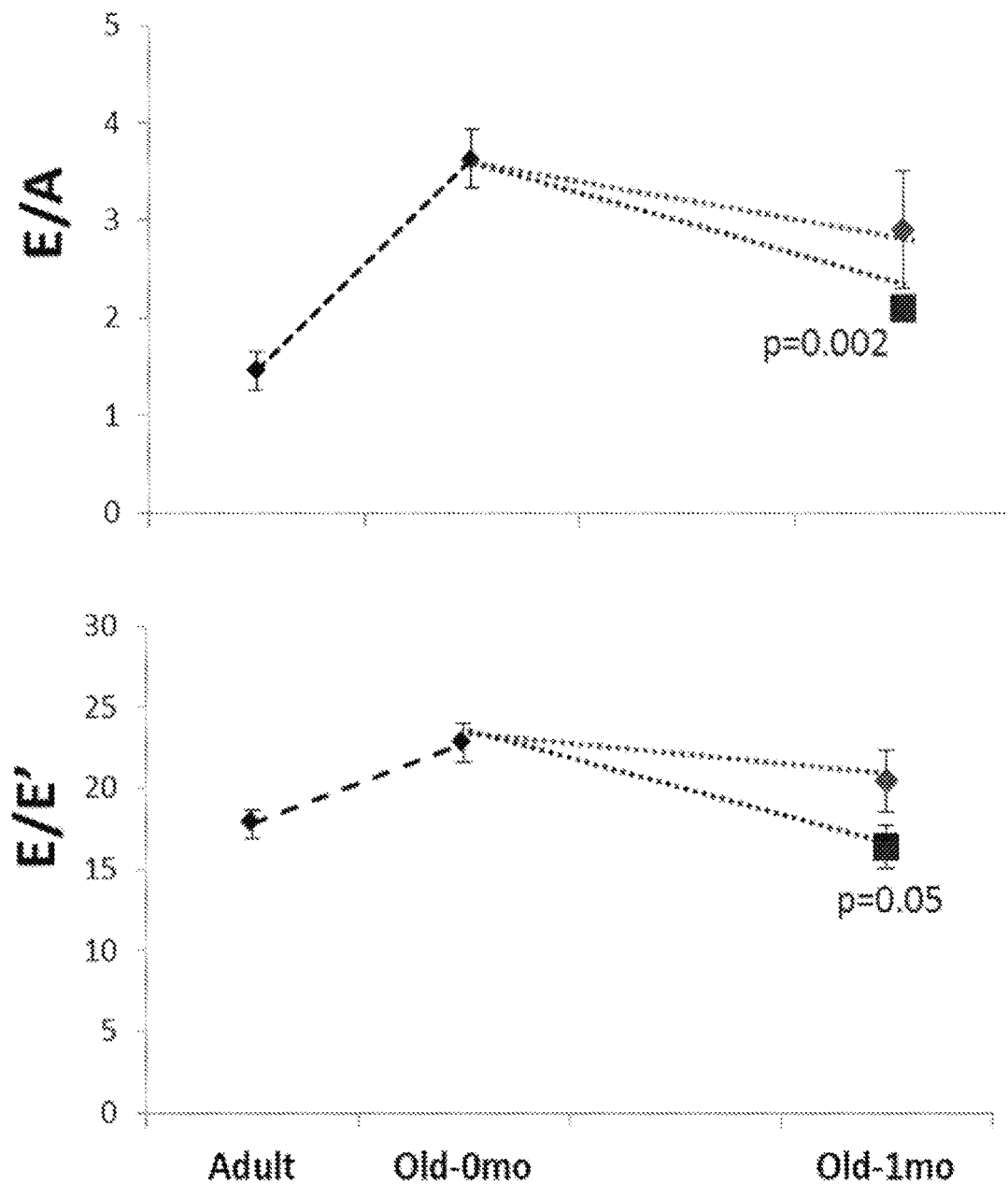
Figures 6, 6C:

FIG. 6. Young CDC treatment decreases left ventricular stiffness in old animals. Changes in stiffness-related echo-parameters over 1-month period in CDC-transplanted (blue, n=11) and control, PBS (red, n=11) groups. FIG. 6A. Bars represent the change in a parameter between study endpoint and baseline values. FIG. 6B. E/A and E/E' ratio in adult, 7-months old rats (n=5) and old, 21 and 25-months old rats (n=25) at baseline (black) and one month after treatment with CDC (n=11) or PBS (n=11). FIG. 6C. Representative images of echo-Doppler transmitral flow. Statistical analysis: significant p-values result of T-Student test between groups (black) or paired-test between baseline and endpoint (blue) are shown.

Figure 7:
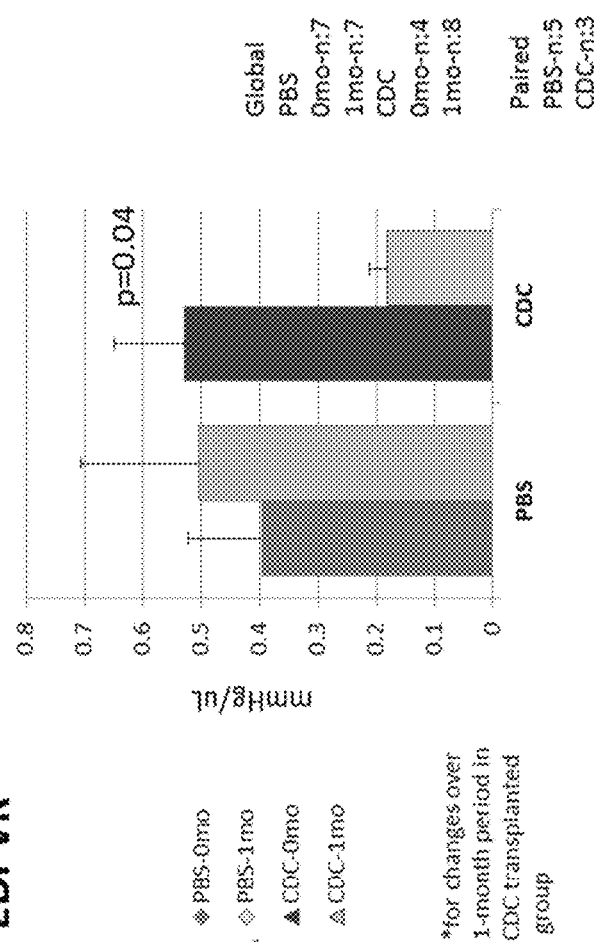
Figure 7:
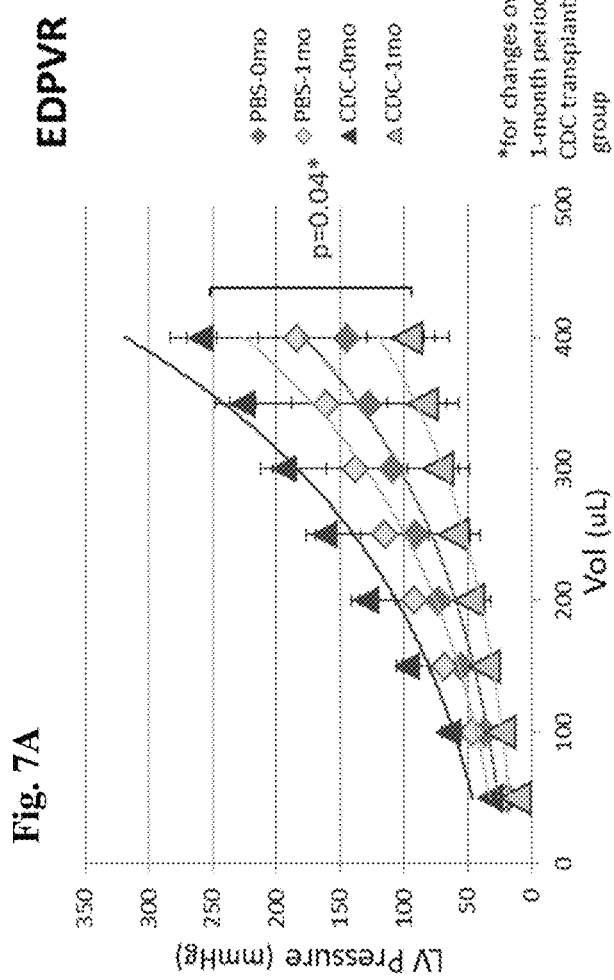
Figure 7C:
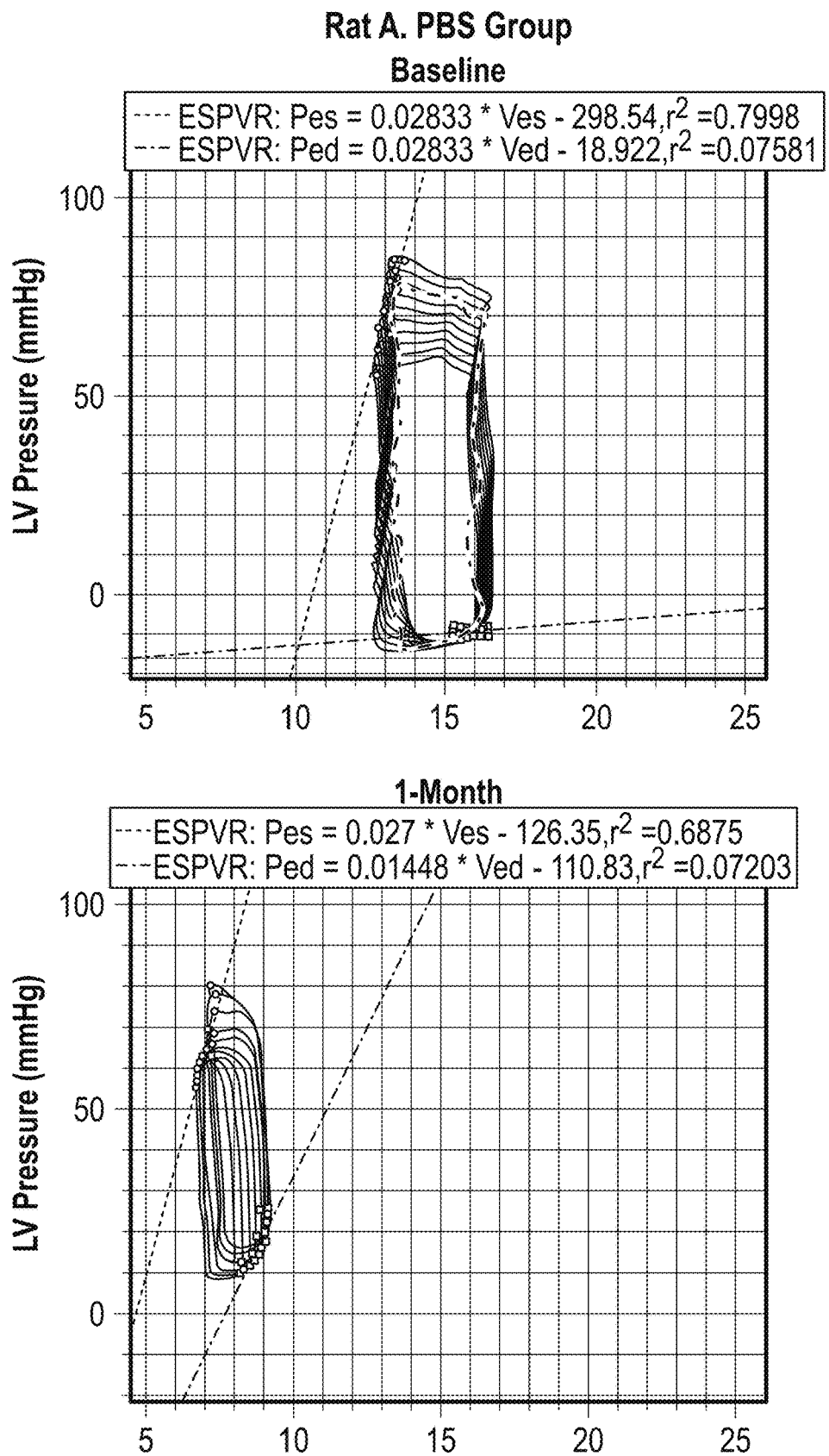
Figure 7C:
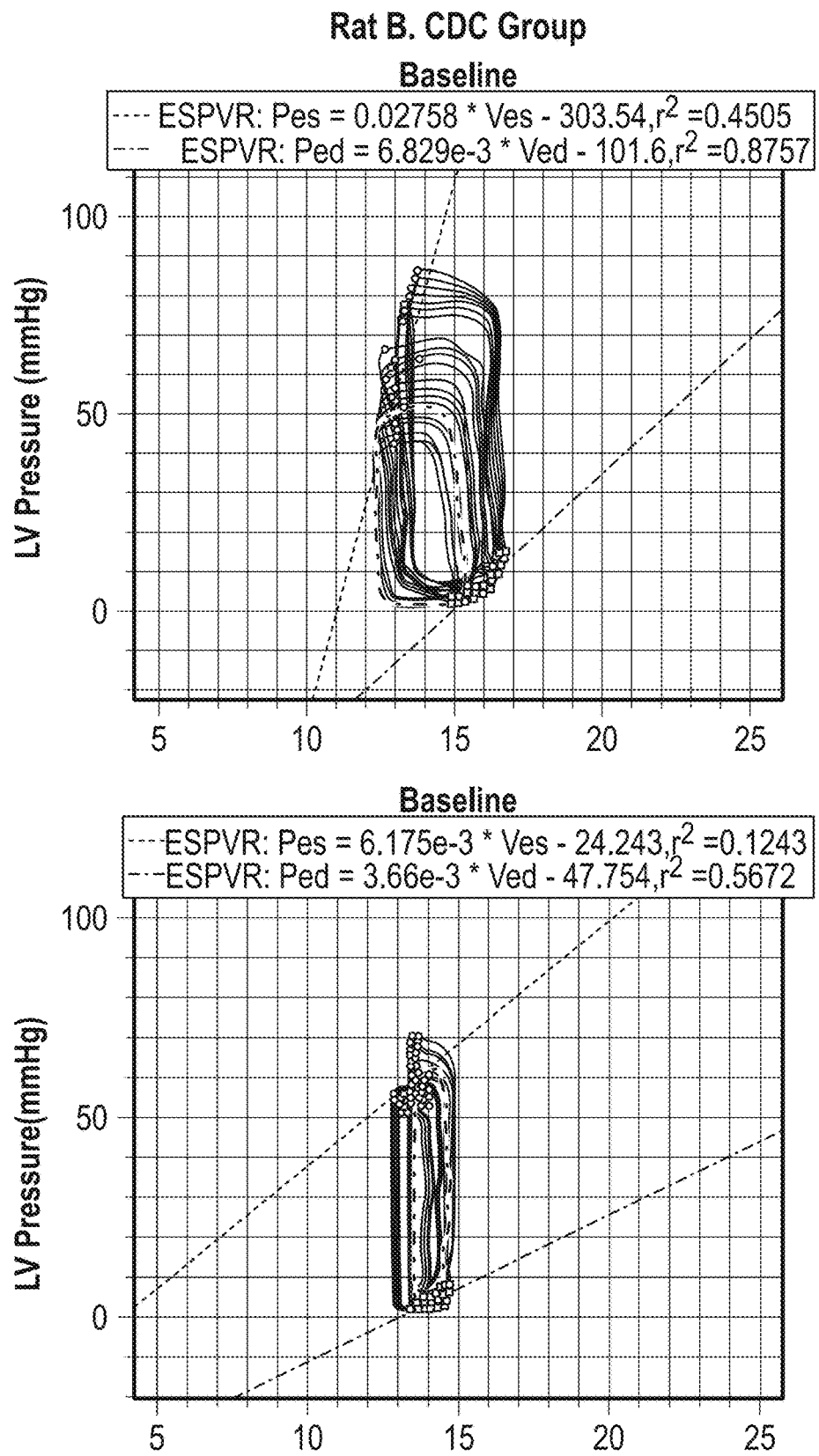

FIG. 7. Young CDC transplantation causes downward displacement of the end-diastolic pressure-volume relationship. Changes in left ventricular (LV) end-diastolic pressure-volume relationship (EDPVR) over 1-month period in CDC-transplanted (blue tones) and control, PBS (red tones) groups. EDPVR were obtained from pressure-volume (PV) loop recordings. FIG. 7A. Extrapolation of EDPVR curves at baseline (dark colors) and at endpoint (light colors) in CDC-treated (n=3) and control, PBS-injected (n=5) animals. FIG. 7B. EDPVR values at baseline (dark colors) and at endpoint (light colors) in CDC-treated (n=4 and 8 at baseline and endpoint, respectively) and control, PBS-injected (n=7 at both timepoints) animals. FIG. 7C. Representative images of PV-loops in CDC-treated and control animals. Statistical analysis: significant p-values result of T-Student test between groups (black) or paired-test between baseline and endpoint (blue) are shown.

FIG. 8. Young CDC transplantation accelerates left ventricular relaxation in old animals. Changes in left ventricular (LV) relaxation-related hemodynamic parameters over 1-month period in CDC-transplanted (blue tones, n=11) and control, PBS (red tones, n=11) groups. FIG. 8A. The constant of relaxation, Tau in adult, 7-months old rats (n=5) and old, 21 and 25-months old rats (n=25) at baseline (black) and one month after treatment with CDC or PBS. Values are recorded with the pressure transducer inside of the LV, in stable, baseline conditions. FIG. 8B. Tau values at baseline in young, 2-months old (black, n=5), adult, 7-months old (black, n=5) and old rats (dark red and blue) and at endpoint (light red and blue) in CDC-treated (n=11) and control, PBS-injected (n=11) animals. Values are obtained from pressure-volume loop recordings. FIG. 8C. Minimum Dp/Dt in adult, 7-months old rats (n=5) and old, 21 and 25-months old rats (n=25) at baseline (black) and one month after treatment with CDC or PBS. Statistical analysis: significant p-values result of T-Student test between groups (black) are shown.

FIG. 9. Young CDC transplantation increases exercise capacity in old rats with age-related functional decline. Changes in exercise capacity over 1-month period in CDC-transplanted (blue, n=11) and control, PBS (red, n=11) groups. FIG. 9A. Maximum distance on the treadmill in adult, 7-months old rats (n=5) and old, 21 and 25-months old rats (n=25) at baseline (black) and one month after treatment with CDC (n=11) or PBS (n=11) is represented. FIG. 9B. Bars represent the change in the max. walking distance on the treadmill between study endpoint and baseline values. Statistical analysis: significant p-values result of T-Student test between groups (black) or paired-test between baseline and endpoint (blue) are shown.

FIG. 10. Young CDC transplantation ameliorates, partly age-related, body weight loss. Body weight changes over 1-month period in CDC-transplanted (blue, n=11) and control, PBS (red, n=11) groups. FIG. 10A. Body weight at baseline in adult, 7-months old (n=5) and old rats, 21 and 25-months combined (Old-0 mo, n=25) or individually is represented in black. Changes over one-month period in CDC-transplanted or PBS-injected are represented in blue and red, respectively (n=11, in each group). FIG. 10B. Bars represent weight change between study endpoint and baseline values. Statistical analysis: significant p-values result of T-Student test between groups (black) or paired-test between baseline and endpoint (blue or red) are shown.

Figure 11:
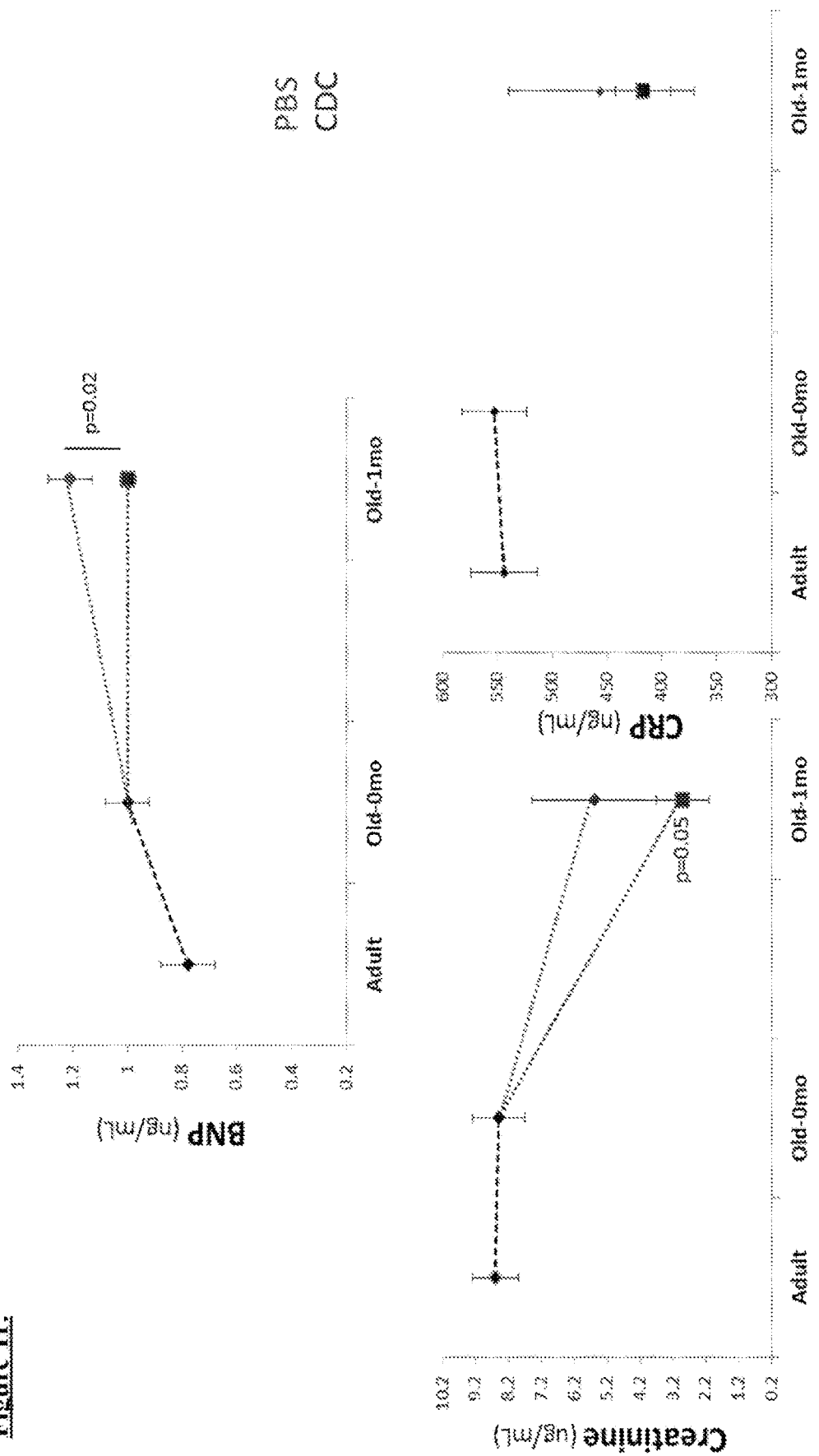

FIG. 11. Changes in serum markers. Over 1-month period in CDC-transplanted (blue, n=11) and control, PBS-injected (red, n=11) groups. Serum levels of Brain Natriuretic Peptide (BNP), Creatinine and C-reactive protein (CRP) in adult, 7-months old rats (n=5) and old, 21 and 25-months old rats (n=25) at baseline (black) and one month after treatment (only in the experimental, old animals) with CDC (n=11) or PBS (n=11) are presented. Statistical analysis: significant p-values result of T-Student test between groups (black) or paired-test between baseline and endpoint (blue) are shown.

Figure 12:
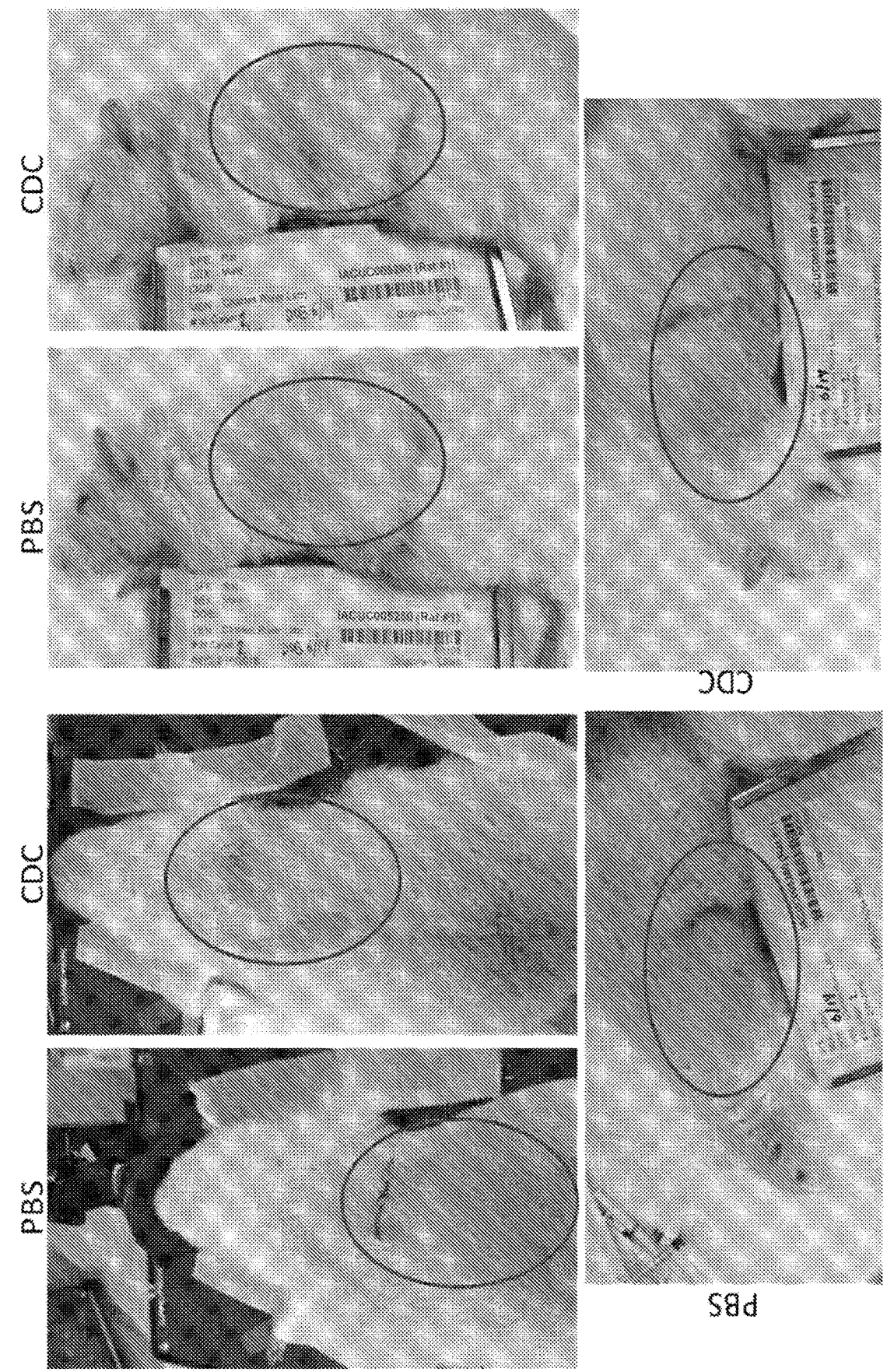

FIG. 12. Young CDC transplantation stimulates hair regrowth in old animals. Differences in hair regrowth 3-weeks after shaving in old rats transplanted with CDC or injected with placebo. Representative pictures of some of them. This evaluation was done in 12 animals, and in 10 of them visually detectable differences, with more pronounced regrowth among CDC-treated animals, were detected.

Figures 13, 13A, 13B:
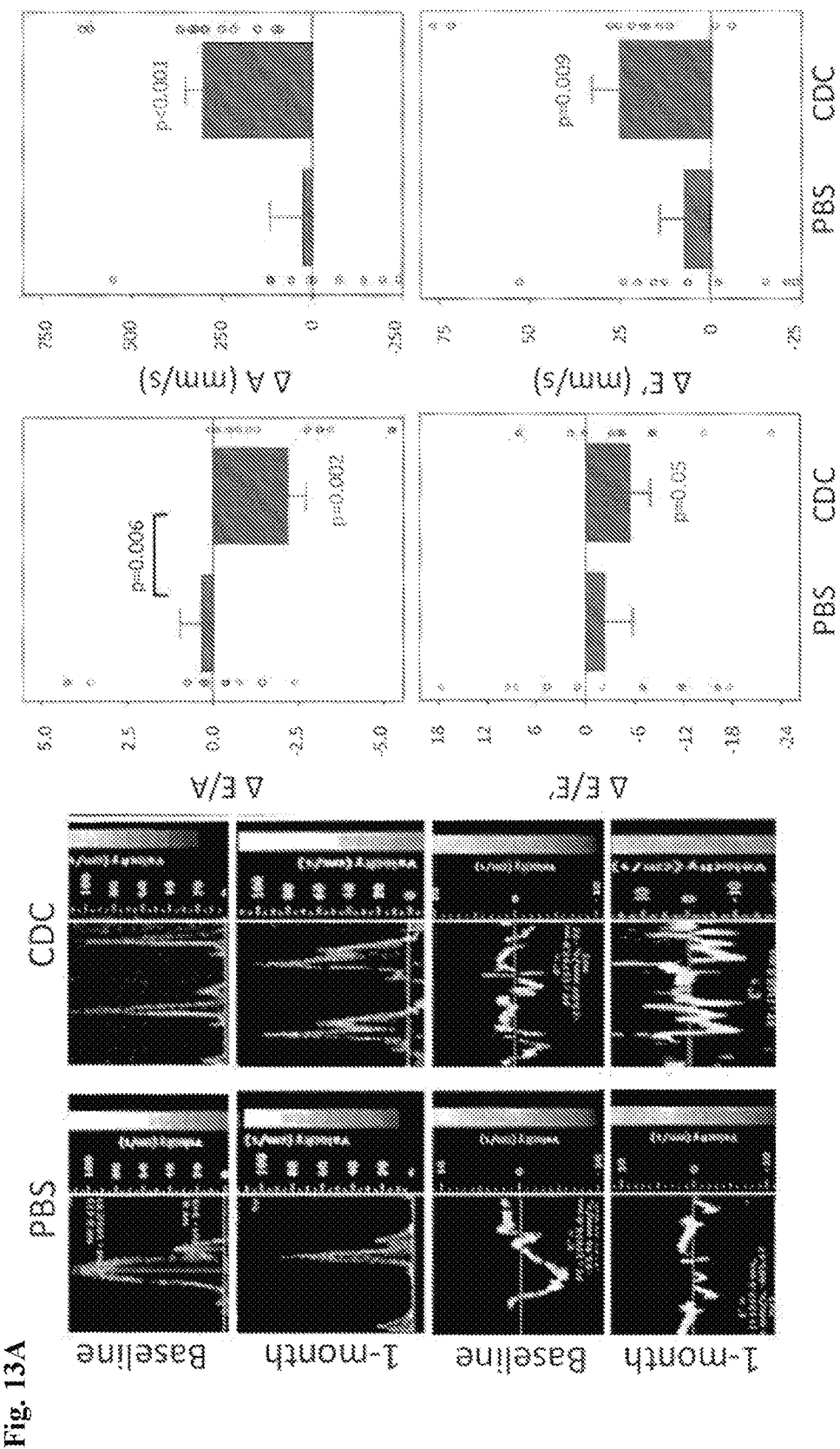

FIG. 13. Echocardiographic and haemodynamic changes in diastolic function. FIG. 13A. Representative images of echo-Doppler transmitral flow and of tissue Doppler in a rat from the phosphate-buffered saline (PBS-control) and in a rat from the cardiosphere-derived cell (CDC) transplanted groups. FIG. 13B. E/A and E/E' ratios are decreased in CDC-treated rats after 1 month. FIG. 13C. Representative images of left ventricular (LV) pressure-volume loops (PVL) in a rat from PBS-control and CDC-treated groups. FIG. 13D. LV end-diastolic pressure-volume relationship (EDPVR) slopes are decreased in old CDC-treated group after 1 month and the time constant of relaxation, Tau is significantly lower in this group vs. control PBS. Number of animals: CDC-treated (n=11) or PBS-injected (n=11). P-values: all significant values are shown. Blue values (CDC group) represent the significance of the difference between baseline and end point within the group. Black values represent the significance between the groups.

FIG. 14. Structural changes of the left ventricle and circulating levels of BNP. FIG. 14A. Representative M-mode echocardiographic images from a rat from the phosphate-buffered saline group (PBS-control), and from a rat in the cardiosphere-derived cell (CDC) transplanted group. FIG. 14B. CDC injected rats (n=11) had decreased echo-measured thickness of the interventricular septum and LV posterior wall. The control PBS rats (n=11) showed an opposite trend. FIG. 14C. Histological sections of myocardium from a rat in each group. FIG. 14D. Pooled data for cardiomyocyte cross sectional area in CDC-injected (n=6) vs. PBS-injected (n=5) rats. FIG. 14E. Representative heart sections stained with Masson's trichrome. FIG. 14F. CDC-group (n=6) exhibited a decrease of fibrosis vs. control PBS (n=5). FIG. 14G. Serum levels of BNP in young (n=5), old animals at baseline (n=14) and after 1-month of treatment with CDC (n=11) or PBS (n=11). IVS: interventricular septum; LV-AW: left ventricular anterior wall; LV-LW: left ventricular lateral wall; LV-PW: left ventricular posterior wall; RV: right ventricular free wall. P-values: all significant values are represented. Blue values (CDC group) represent the significance of the difference between baseline and end point within the group. Black values represent the significance between the groups.

FIG. 15. Expression of aging and cellular senescence-related genes. Results are expressed as fold regulation vs. old rats injected with phosphate buffered saline (old-PBS). FIG. 15A. Significantly up-regulated genes in hearts of young and/or old-CDC animals compared with old-PBS group. FIG. 15B. Significantly down-regulated genes in hearts of young and/or old-CDC animals compared with old-PBS group. FIG. 15C. Diagram showing the proportion of differently-regulated genes (only those with significant differences) in young and/or old-CDC treated rats vs. old-PBS animals (62 genes of a total of 168 analysed). Of those 62 genes, 85.5% of the CDC-related changes recapitulated the gene expression pattern observed in young rats. FIG. 15D. Genes with significant differences in both young and old-CDC rats vs. old-PBS animals. Ns: young rats (n=4), old-PBS (n=7), old-CDC (n=8).

Figures 16, 16A:
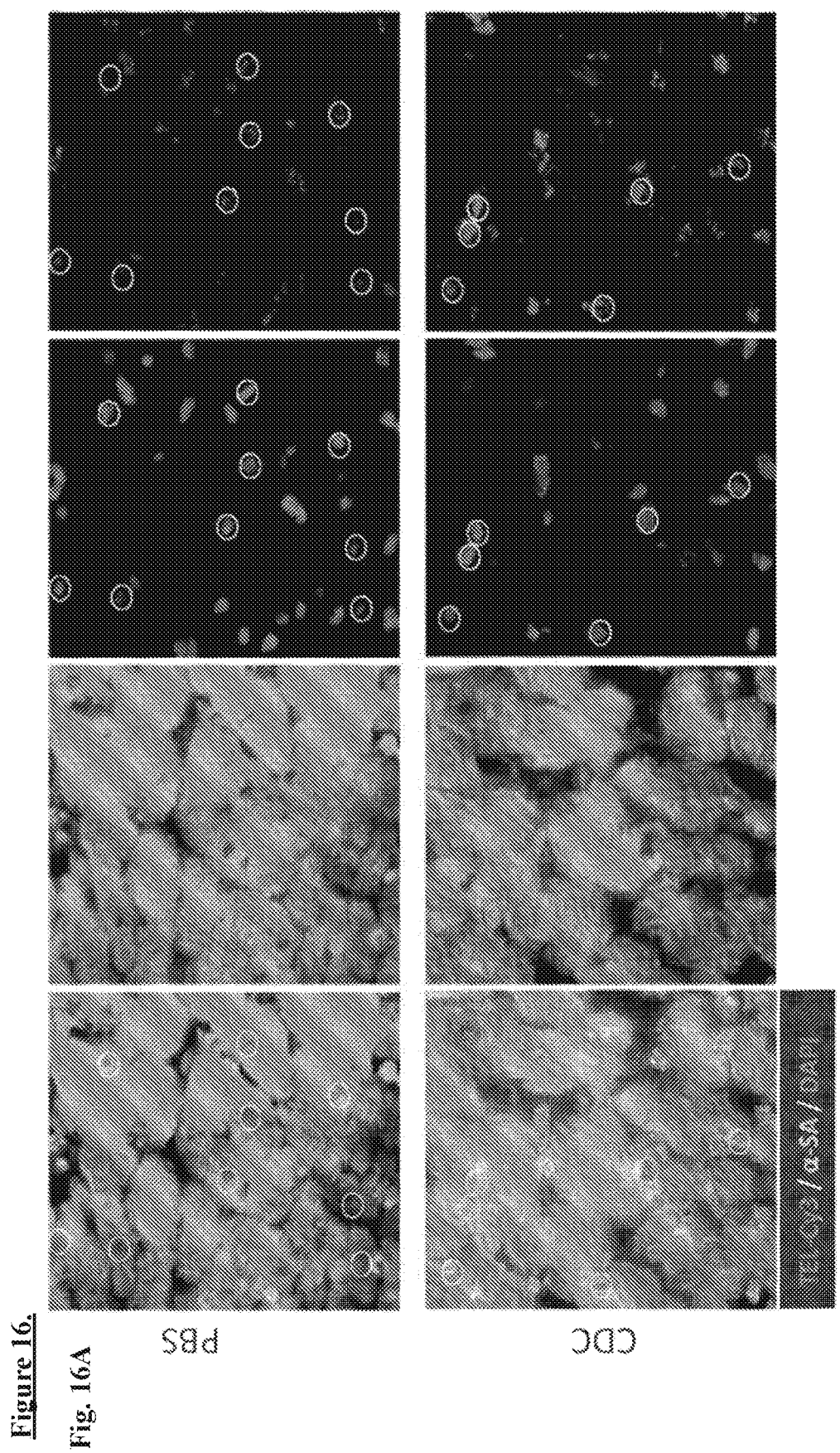
Figure 16B:
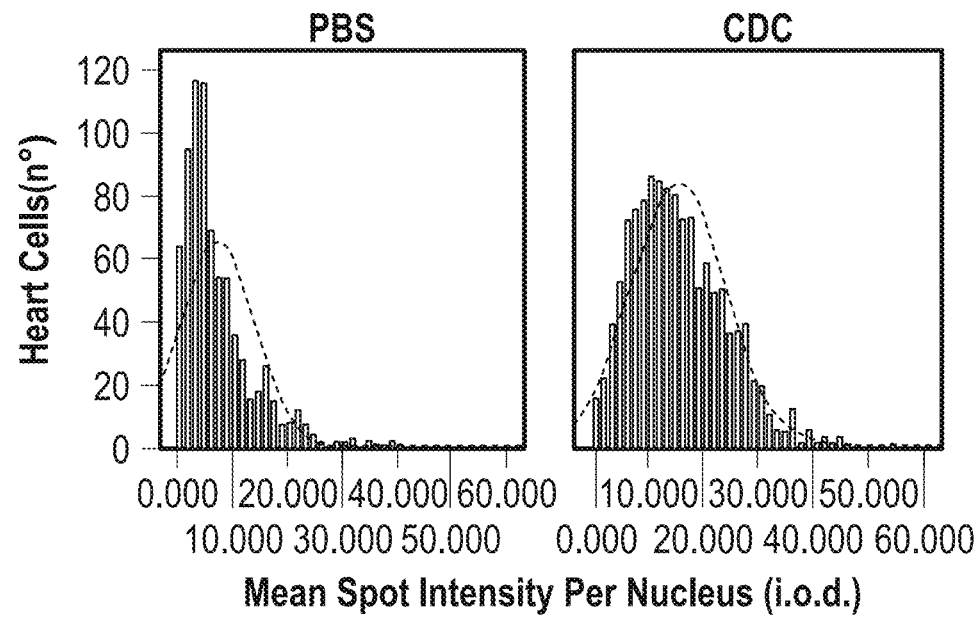
Figure 16B:
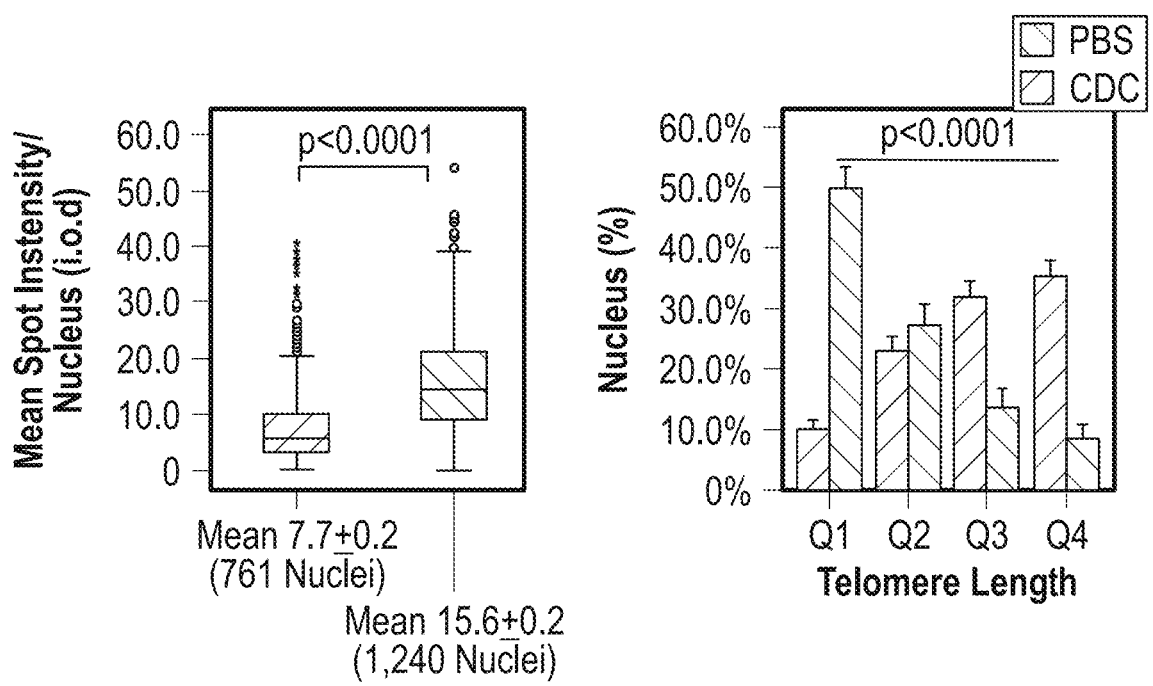
Figure 16C:
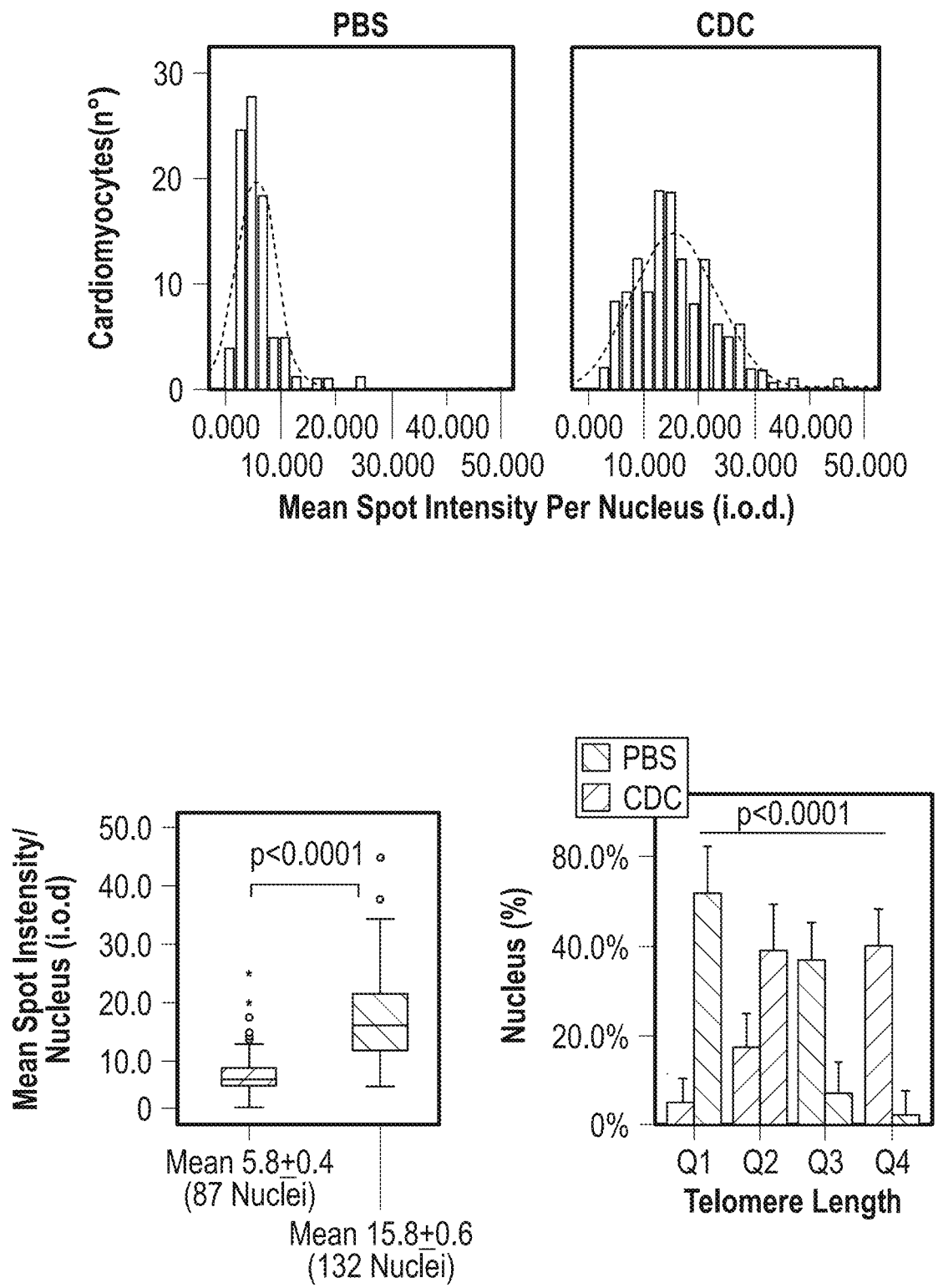

FIG. 16. Telomere length of heart cells. FIG. 16A. Representative detail of a confocal maximum projection images of telomere Q-FISH (TEL-Cy3) and alpha-sarcomeric actinin (a-SA) immunofluorescence in old animals treated with phosphate-buffered saline (PBS, n=5) and old rats transplanted with cardiosphere-derived cells (CDC, n=6). Cardiomyocyte nuclei were manually selected using the a-SA immunofluorescence image. Only unambiguously identified cardiomyocytes were considered for analysis. Dashed lines indicate cardiomyocytes with the telomere signal. FIG. 16B. Telomere length distribution (i), mean telomere length (ii), and cell distribution according to quartiles (Q1—the shortest and Q4—the longest) of telomere length (iii) in entire population of heart cells. FIG. 16C. Telomere length distribution (i), mean telomere length (ii), and cell distribution according to quartiles (Q1—the shortest and Q4—the longest) of telomere length (iii) in cardiomyocytes.

FIG. 17. Systemic anti-aging effects. FIG. 17A. Changes in maximal exercise capacity after 1 month of treatment show an increase in the cardiosphere derived cell (CDC, n=11) transplanted animals vs. a decrease in the phosphate-buffered saline (PBS, n=11) group. CDC-related improvements amount to ~20% of baseline functional capacity. FIG. 17B. Body weight loss after 1 month of treatment. Weight decreased in both groups, but was less severe in CDC (n=11) vs. control (n=11) rats. FIG. 17C. Serum markers of inflammation after 1 month of treatment. Fold changes in the CDC group vs. control rats; only cytokines with significant differences between the groups (n=7 in each group) are presented. FIG. 17D. Estimated glomerular filtration rate (eGFR) based on serum levels of creatinine (sCr), blood urea nitrogen (BUN) and weight. Although animals in the PBS group lost more weight than rats injected with CDCs, the latter experienced a greater decrease of sCr levels (P=0.04) and BUN (BUN levels increased in the control rats). These changes translate into a 25% increase of eGFR in CDC-treated animals and an 11% decrease in PBS-injected animals. FIG. 17E. Representative images of hair regrowth 3 weeks after shaving in old rats injected with CDC or PBS, showing more pronounced regrowth among CDC-treated animals. FIG. 17F. Area of impaired hair regrowth in both groups (PBS, n=6; CDC, n=7). For FIG. 17A, FIG. 17B, and FIG. 17F: all significant P-values are shown. Coloured values (blue for the CDC group and red for the PBS group) are related with the changes in a parameter between baseline and end point within the group. Black value are related with the differences between the groups at the same time point.

FIG. 18. Exosome-mediated activation of telomerase-telomere axis and decrease of cell senescence by young CDCs in old human cardiac stromal-progenitor cells (CSPCs). FIG. 18A. Telomerase activity in extracts of CSPCs from old human donors after 96 h was determined following telomeric repeat amplification protocol (TRAP) in four groups: the control group incubated with serum-free media (SF); cells co-cultured with young donor CDCs alone or together with GW4869 inhibitor of exosome release (CDC and CDC-GW, respectively), using transwell membranes; cells co-cultured with young CDC-derived exosomes (CDC-XO) resuspended in serum-free media. FIG. 18B. Representative images of cells subjected to telomere Q-FISH analysis. Nuclei are stained with DAPI and telomeres with specific CY3-labeled probe (red). Telomere length was analysed by measuring the integrated optical density (i.o.d.) of the Cy3-channel within the nuclear borders after subtracting the background i.o.d. Results adjusted to the nuclear area are presented as well. FIG. 18C. Histochemistry images for senescence-associated b-galactosidase (SA-GAL) (blue). Proportion of senescent, SAGALþ cells after 96 h co-incubation time period with young CDC-XO or SF.

Figure 19:
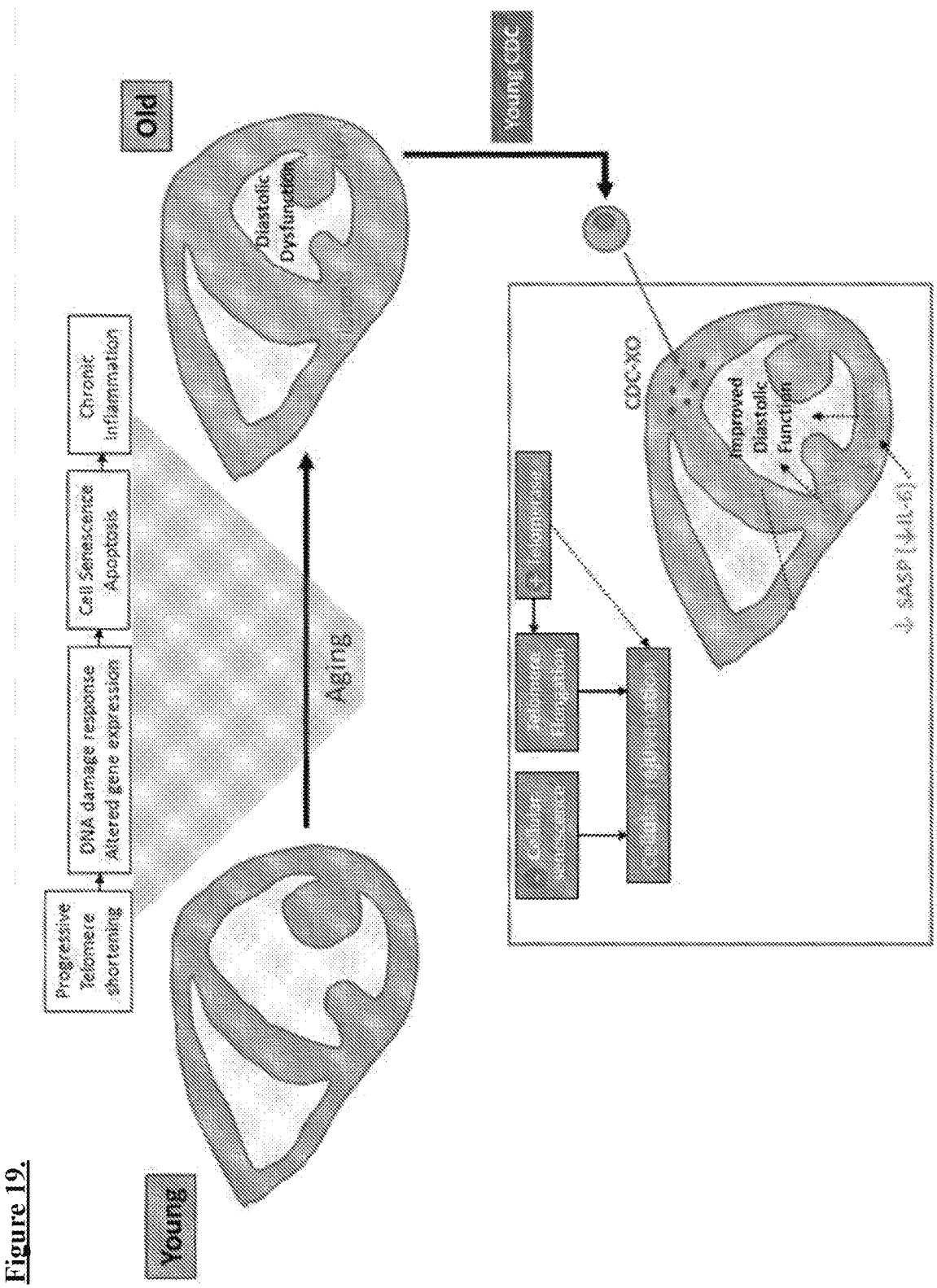

FIG. 19. Schematic depiction of heart aging and proposed mechanisms whereby young CDCs exert anti-senescent effects. The process of aging is depicted in the upper row. Transplanted CDCs secrete exosomes (CDC-XO) which lead to cellular rejuvenation. In the heart, left ventricular hypertrophy (LVH) is attenuated and fibrosis is decreased, leading to improved diastolic function. Systemically, a reduction of the senescence-associated secretory phenotype (SASP) contributes to systemic benefits.

Figures 20, 20M, 20N:
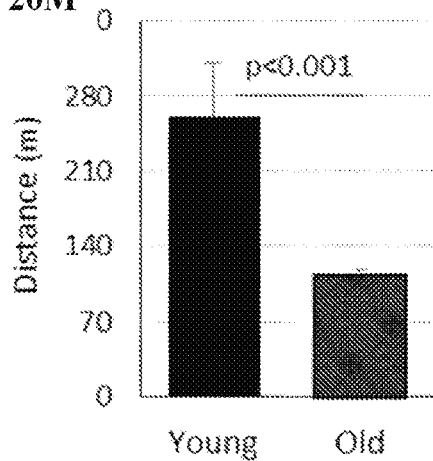

FIG. 20. Old Fisher 344 rats represent a good model of age-related diastolic dysfunction. FIG. 20A-FIG. 20G: Echocardiographic and hemodynamic parameters related with diastolic function (both left ventricular (LV) stiffness (FIG. 20A, FIG. 20B, FIG. 20C) and relaxation (FIG. 20D, FIG. 20E)), and LV structure (FIG. 20F, FIG. 20G) are presented for young (n=10) and old rats (n=25). Table n presents the results of the lineal regression analysis in the subgroup of oldest rats (n=5) in the young group, 21— (n=20) and 25-months (n=5) old rats. Results indicate a gradual and steady impairment of LV diastolic function after maturation of animals, associated with increase of the LV mass and end-diastolic diameter. Systolic function remains unchanged. (FIG. 20H, FIG. 20I, and FIG. 20N) Old animals present significant differences in vital constants (FIG. 20K, FIG. 20L) and functional capacity (FIG. 20M), though blood pressure was unchanged (FIG. 20J). Same acronyms as used for FIG. 5.

Figure 21:
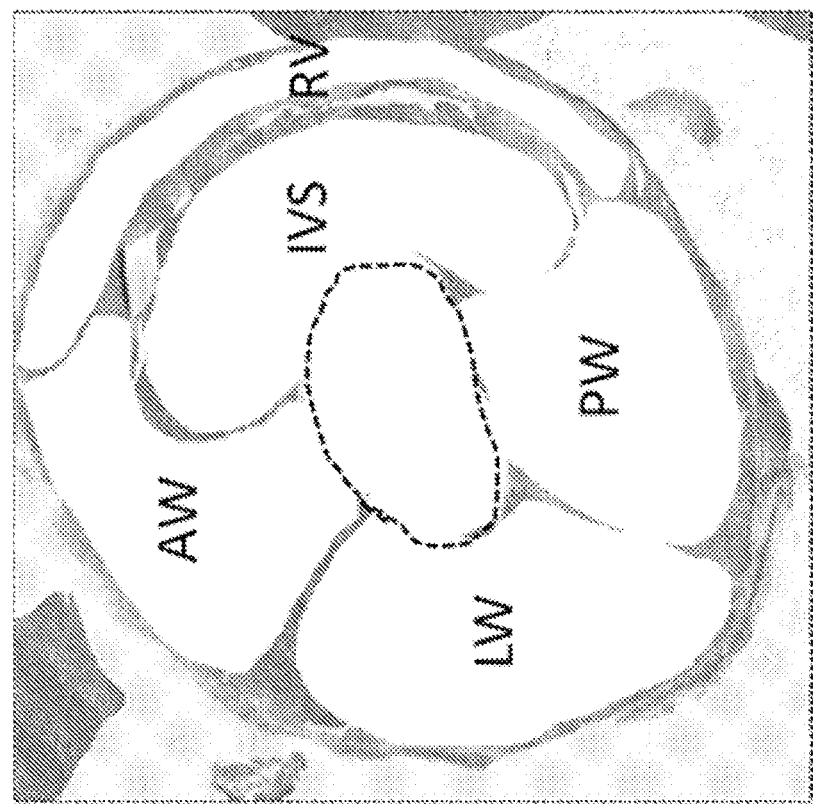
Figure 21:
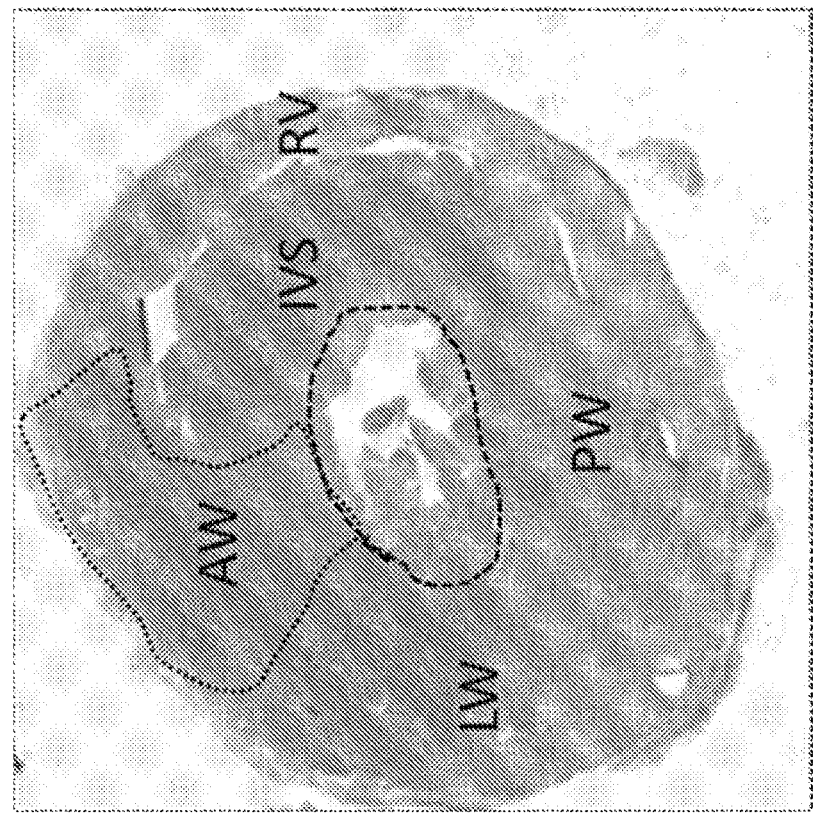

FIG. 21. Schematic representation of heart wall distribution for fibrosis analyses.

FIG. 22. Serum levels of cytokines and renal function-related markers.

FIG. 23. Hair regrowth. After 3 weeks of shaving in PBS-injected (FIG. 23A) and CDC-transplanted (FIG. 23B) rats. FIG. 23C. Schematic representation of the estimation of the impaired hair regrowth area.

Figure 24:
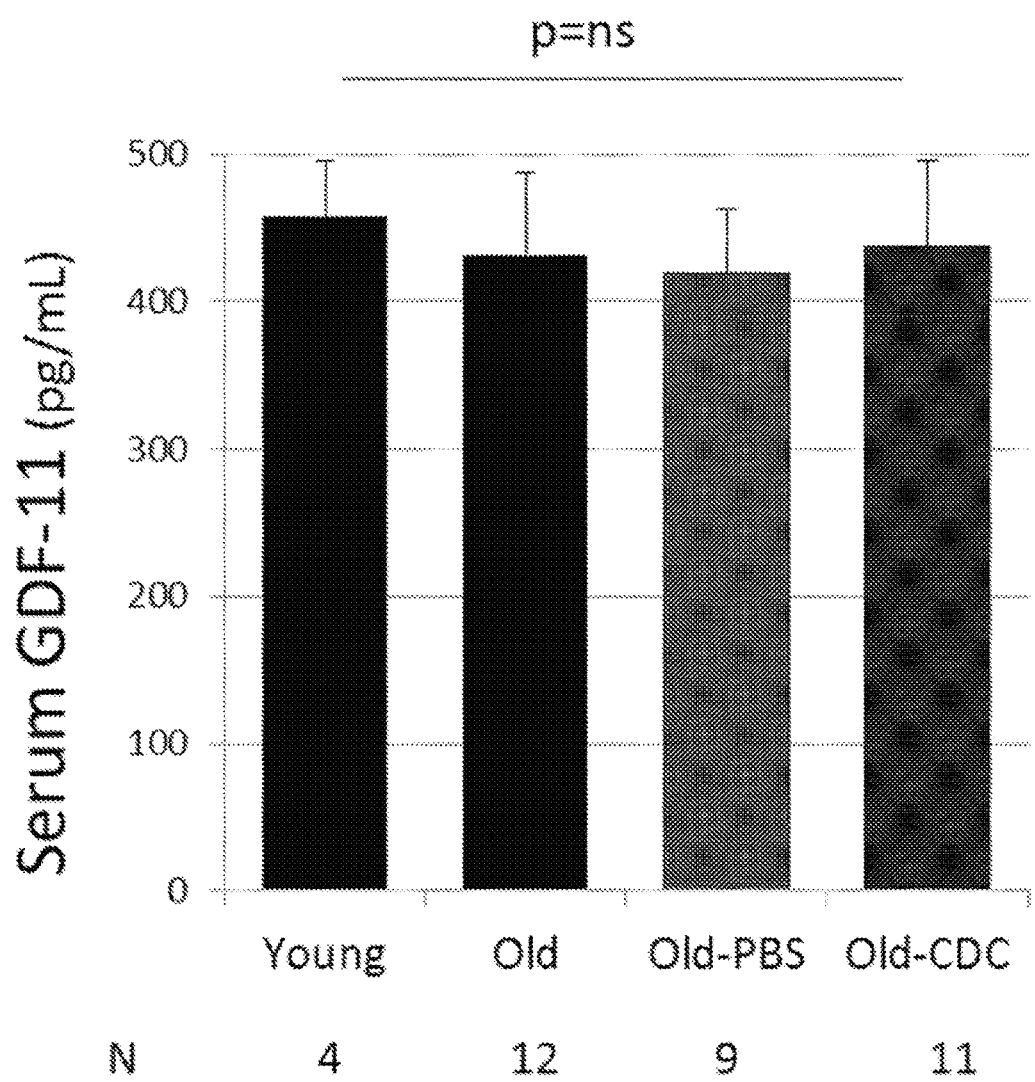

FIG. 24. Serum levels of GDF-11 in young, old rats at baseline (Old) and at study end-point (Old-PBS and Old-CDC).

FIG. 25. Anti-senescent effects of young CDC-derived exosomes (CDC-XO) on old rat cardiomyocytes in vitro. FIG. 25A. Telomerase activity in extracts of a whole population of cells was determined following the TRAP, after 72-hours. CDC-XO-primed cells presented a 2-fold increase of telomerase activity. FIG. 25B. Histochemistry for SA-GAL (blue, marked with arrows) after 72 hours. Importantly, senescent, SA-GAL+ cells were found among the non-cardiomyocyte population of cells. FIG. 25C. Representative pictures of cells stained for α-sarcomeric actinin (α-SA) after 72-hours. While in the SF group the number of cardiomyocytes decreased 50% over 72 hours, in the CDC-XO treated group it was maintained practically unchanged compared with baseline.

Figures 26, 26A, 26B:
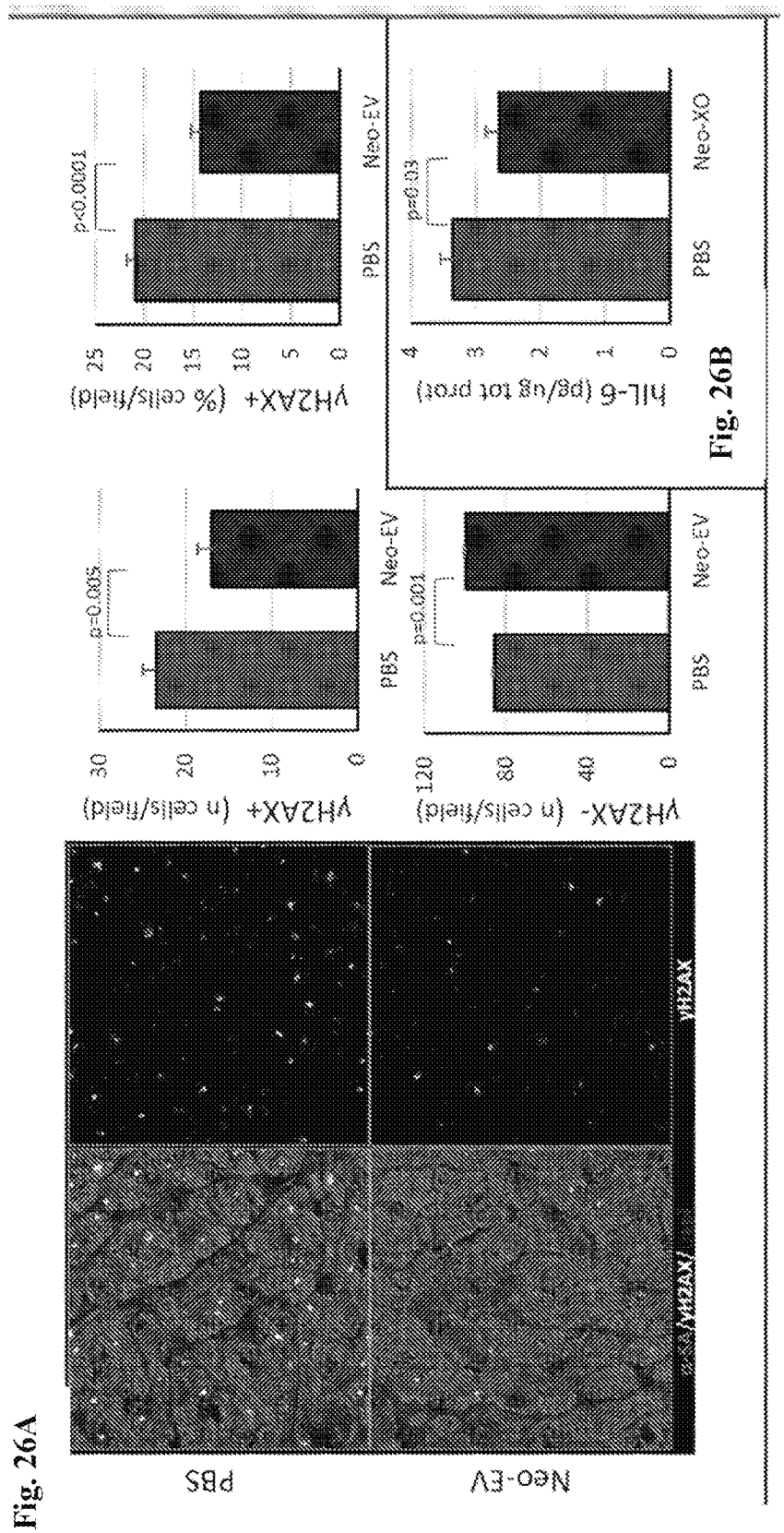

FIG. 26. Young cardiosphere-derived cell (CDC) derived exosomes (Neo-EV) rejuvenate heart tissue in old rats. FIG. 26A. Lower number of cells expressing stained for α-sarcomeric actinin (α-SA) aftero-EV vs control (PBS) group. FIG. 26B. Pro-inflammatory cytokine, IL-6 is decreased in the heart of Neo-EV vs PBS treated rats. FIG. 26C. Pluripotency marker NANOG and B-cell receptor complex (BCR) are identified as upstream regulators of transcriptional changes associated with Neo-EV vs PBS treatment. FIG. 26D. Serum levels of alkaline phosphatase, a marker of stem cells identified as upregulated in Neo-EV treated rats. FIG. 26E. Neo-EV protects from a decline in blood globulin levels observed in the PBS group, associated with a higher number of white blood cells (WBC), suggesting a better preservation of an immune function in old rats.

Figure 27:
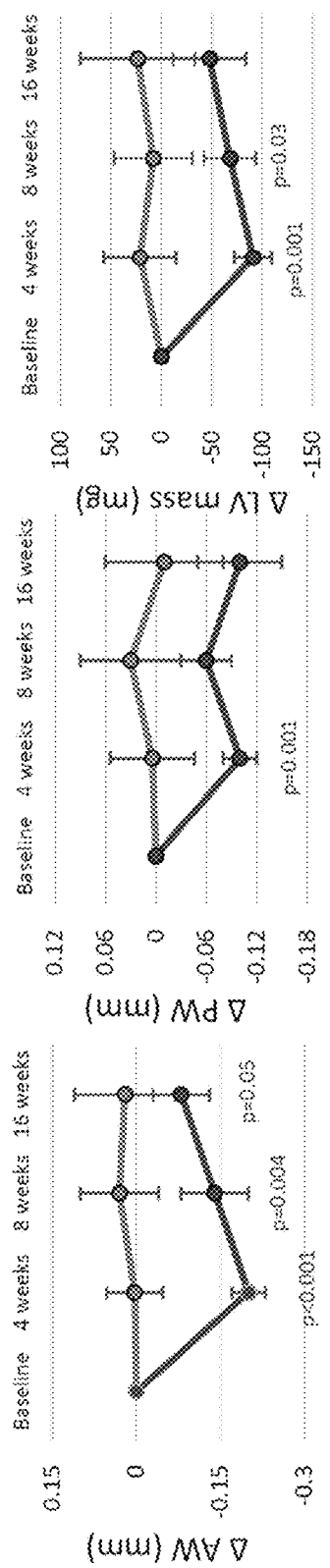
Figure 27:
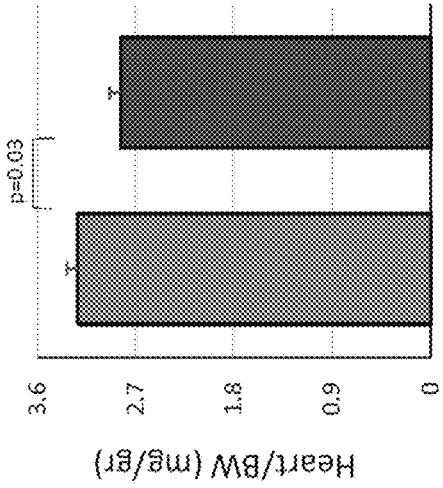
Figure 27:
Figure 27:
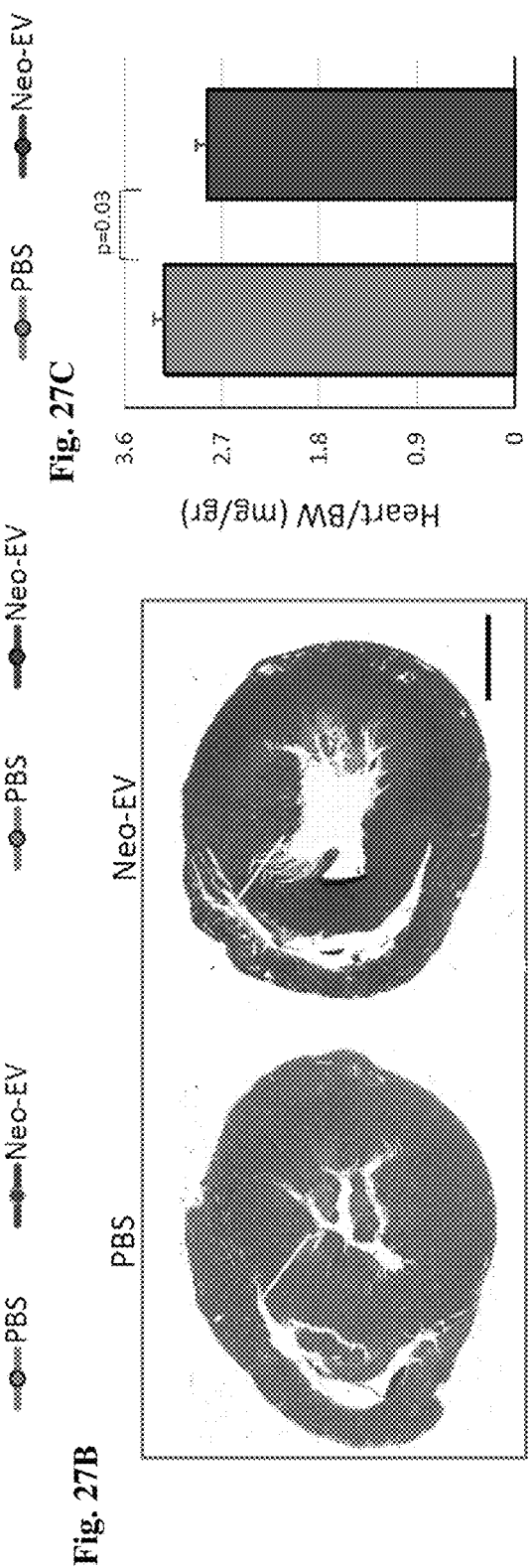
Figures 27, 27D:
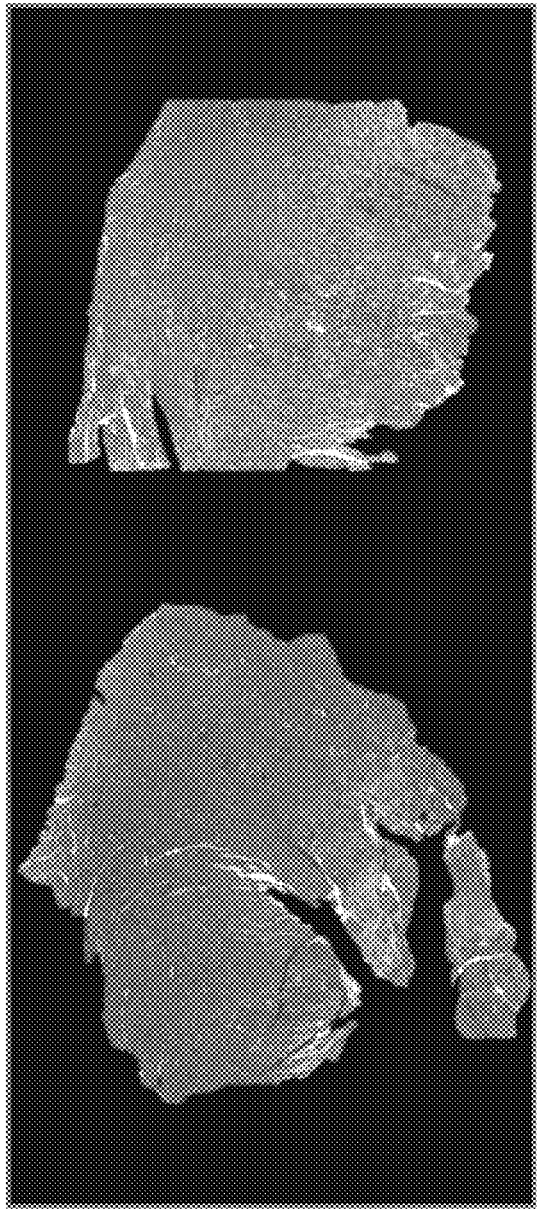
Figure 27E:
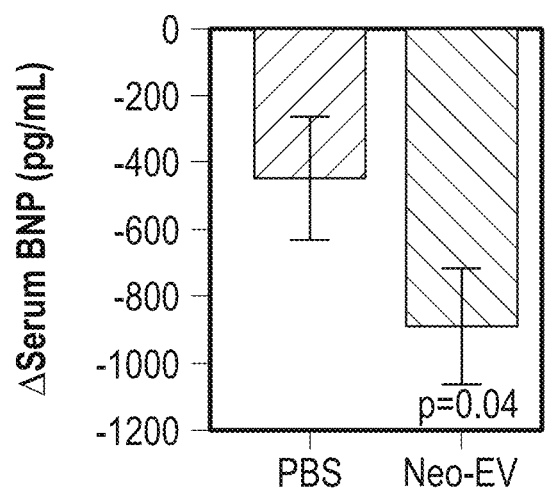

FIG. 27. Treatment with young CDC-exosomes (Neo-EV) improves heart structure and circulating levels of brain natriuretic peptide (BNP) in old rats. FIG. 27A. Echocardiographic follow-up shows a decrease of the thickness of the anterior (AW), posterior (PW) walls and of the left ventricular (LV) mass in the Neo-EV group, effect not observed in the control PBS rats. FIG. 27B. Macroscopic evaluation confirms echocardiographic results with decreased LV hypertrophy in the Neo-EV vs PBS groups. FIG. 27C. Heart/Body weight (BW) is lower in Neo-EV vs PBS rats. FIG. 27D. Neo-EV-treated rats present less myocardial fibrosis compared with the control group. FIG. 27E. Serum levels of BNP decreased significantly only in Neo-EV treated rats.

Figure 28:
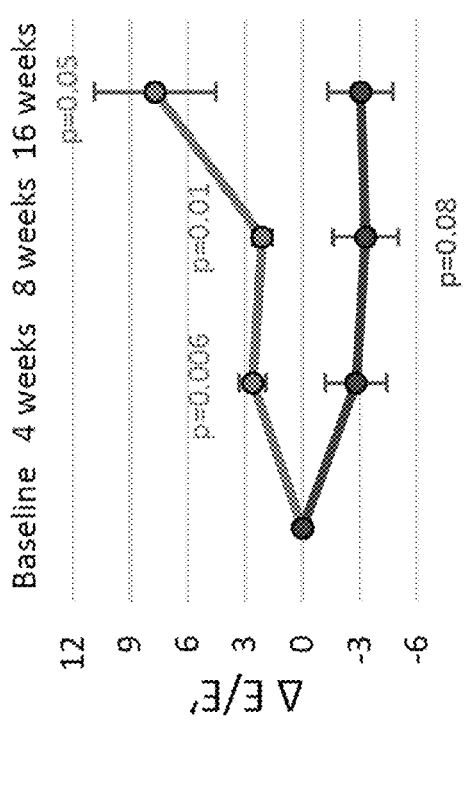
Figure 28A:
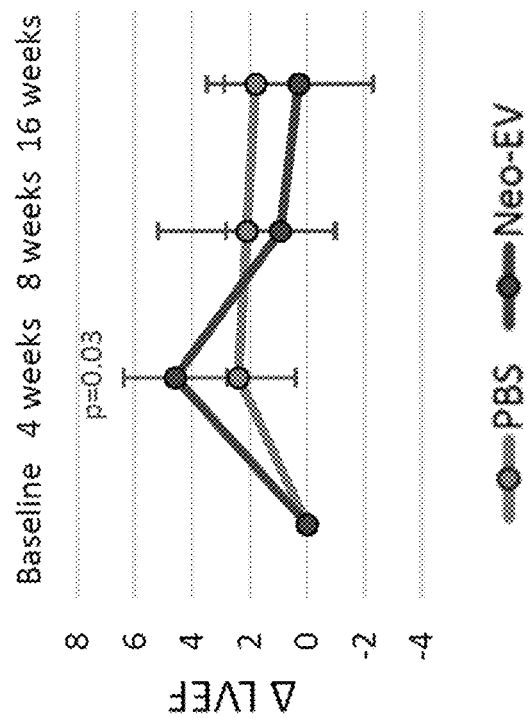
Figure 28C:
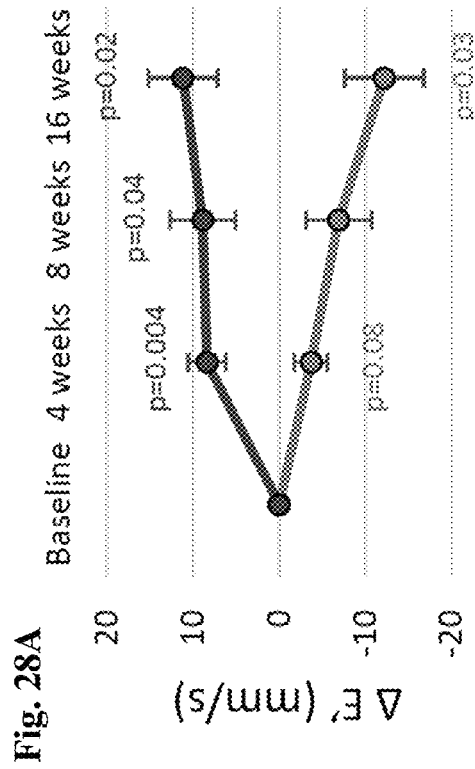
Figure 28B:
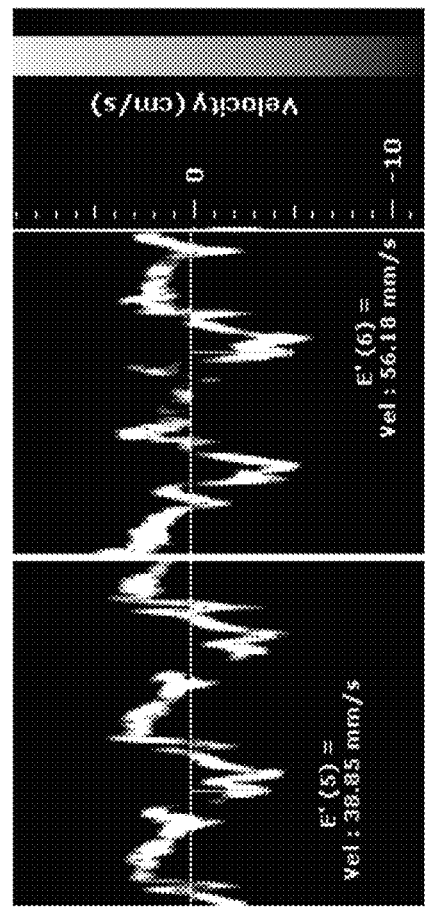

FIG. 28. Young CDC-exosomes (Neo-EV) treatment improves heart function. FIG. 28A. Tissue Doppler Es (Neo-EV) treatment improves heart function of the anterior (AW), posterior (PW) walls and of the left ventricular (LV) mass in the control group. FIG. 28B. Representative images of tissue Doppler in a rat from the Neo-EV treated group. FIG. 28C. Although within normal range in both groups, left ventricular ejection fraction (LVEF) increased after first month of treatment in Neo-EV-injected rats. FIG. 28D. Representative images of left ventricular (LV) pressure-volume loops (PVL) in a rat from PBS-control and Neo-EV-treated groups at study end-point. FIG. 28E. LV end-diastolic pressure-volume relationship (EDPVR) slopes are decreased in old Neo-EV-treated group after four months vs control PBS. FIG. 28F. Cardiac efficiency is higher after four months in Neo-EV vs PBS treated rats.

Figure 29:
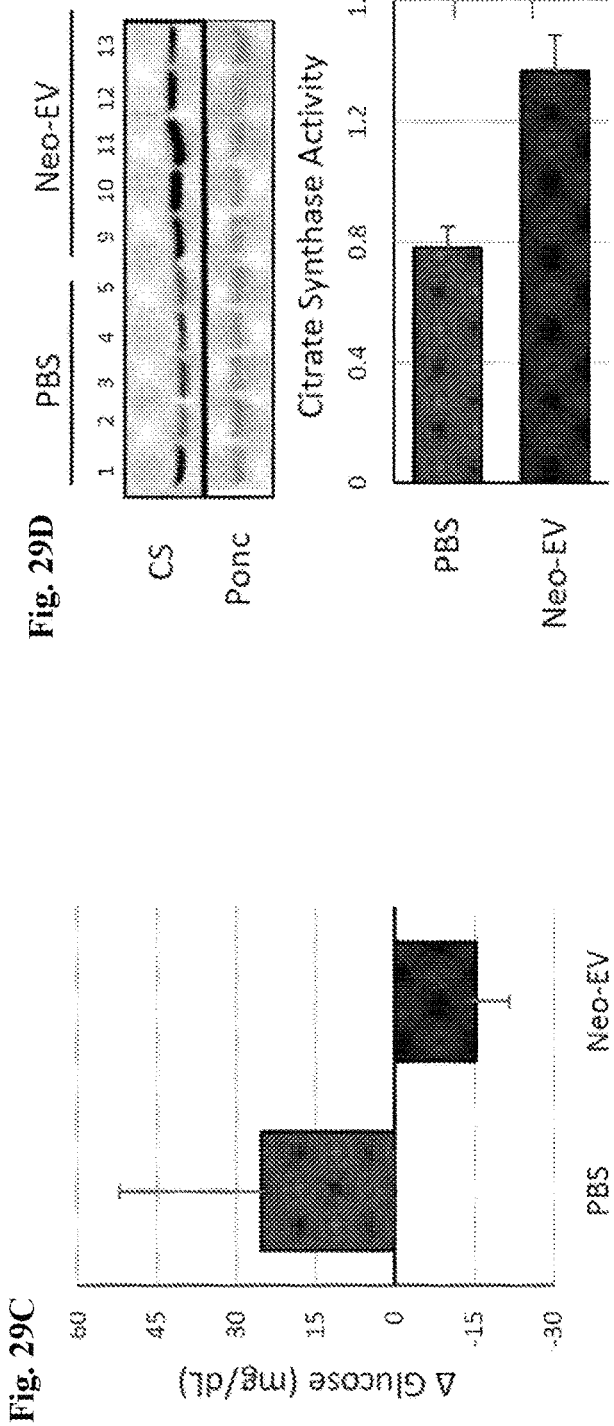
Figure 30A:
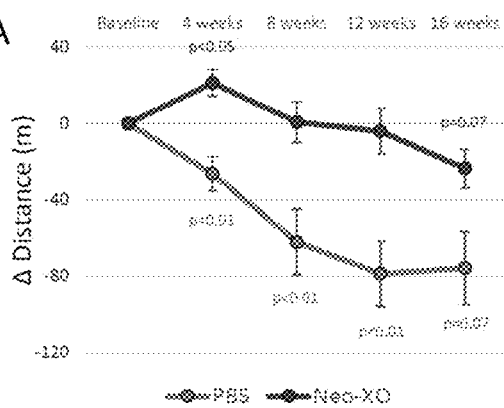
Figure 30B:
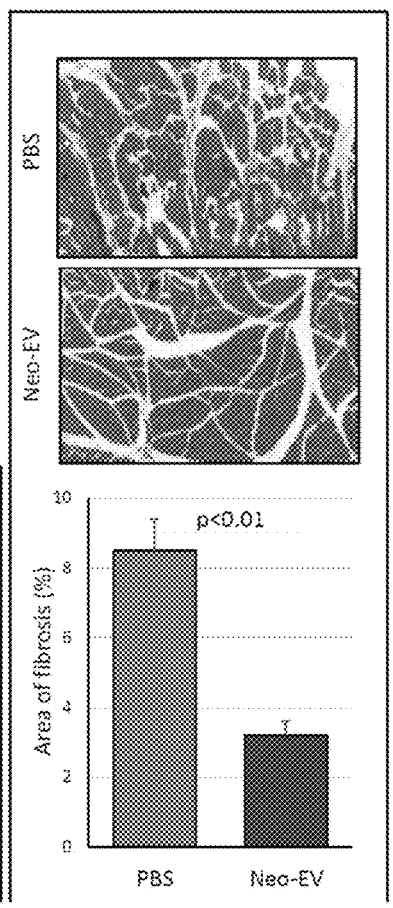
Figure 30C:
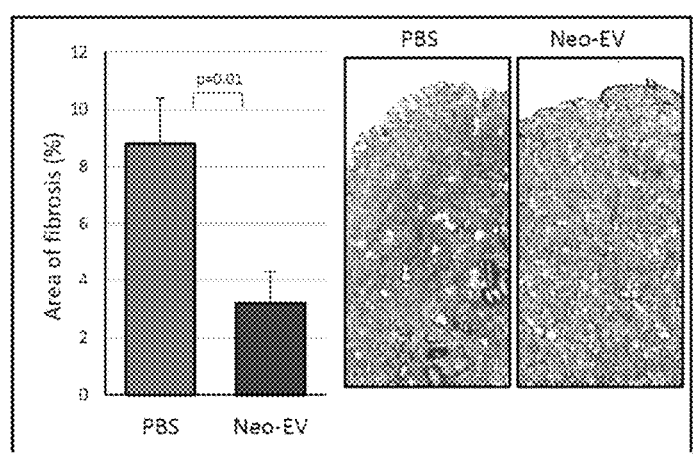
Figure 30D:
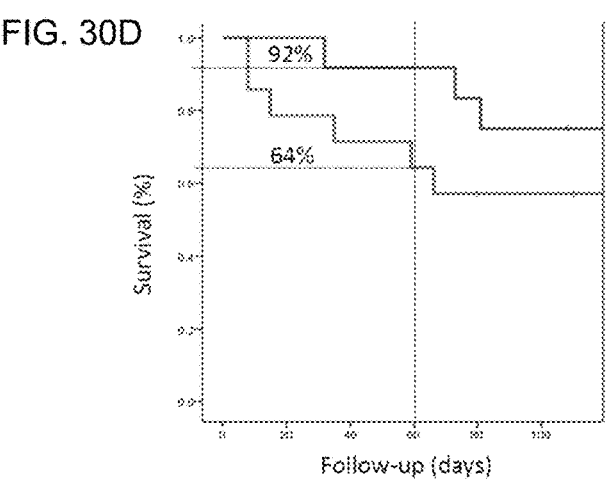
Figure 30E:
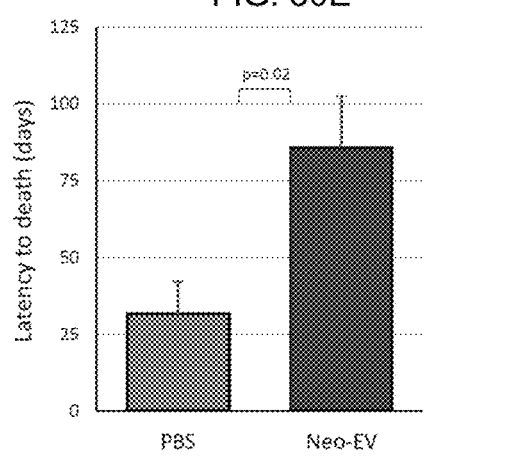

FIG. 29. Treatment with young CDC-exosomes (Neo-EV) improves the metabolic profile of old rats. FIG. 29A. Neo-EV rats presented a steady decline in body weight (BW), the effect was much less pronounced in control rats. FIG. 29B. Proportion of abdominal fat was lower in Neo-EV vs PBS-treated rats after four months. FIG. 29C. Non-fasting glucose levels tend to decrease in Neo-EV, while to increase in PBS rats. FIG. 29D. Activity of skeletal muscle citrate synthase, associated with mitochondrial biogenesis, was higher in Neo-EV vs control animals, probably indicating improved insulin sensitivity. FIG. 29E. Glucose tolerance test shows that Neo-EVs improve glucose metabolism in old rats after 48-hours of administration. FIG. 29F. Trend to lower insulin resistance and improved glucose-induced insulin secretion were associated with Neo-EV-induced improvement of glucose tolerance.

FIG. 30. Young CDC-derived exosomes (Neo-EV) preserve functional capacity and elongate survival of old rats. FIG. 30A. Exercise capacity declined progressively in the control rats while was improved after the first month and preserved after then in Neo-EV-treated animals. FIG. 30B. Skeletal muscle fibrosis decreased 2.6-fold in Neo-EV vs PBS groups. FIG. 30C. Lung fibrosis decreased 2.7-fold in Neo-EV vs PBS groups. FIG. 30D. Kaplan-Meier survival curves show 64 and 92% survival in PBS and Neo-EV rats after two-months of follow-up. FIG. 30E. The latency to death was delayed 2.7-fold in Neo-EV rats.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention.

Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Cardiovascular disease increases markedly in prevalence with aging, creating a huge economic burden. Cell senescence underlies the aging process, and is characterized by progressive shortening of telomeres. Critical shortening of these protective 'caps' on the ends of linear chromosomes is associated with heart dysfunction and hypertrophy, impaired cardiomyocyte proliferation, and reduced regenerative capacity. The aged heart exhibits abnormal relaxation and/or increased stiffness, along with interstitial fibrosis and cardiomyocyte hypertrophy. Among rejuvenating strategies tested to date, parabiosis and cellular reprogramming seem promising, but none has addressed age-related heart dysfunction.

Cardiosphere-derived cells (CDCs) are cells which can differentiate major cell types present in the heart These cells work primarily indirectly, including through secretion of extracellular vesicles such as exosome in a paracrine manner. US 2012/0315252, which is fully incorporated by reference herein, describes CDCs, their derivation from cardiospheres, and their therapeutic utility for increasing the function of a damaged or diseased heart of a mammal. WO 2005/012510, which is fully incorporated by reference herein, in turn describes cardiospheres, their derivation from human or animal cardiac tissue biopsy samples, and their therapeutic utility in cell transplantation and functional repair of the myocardium. See Makkar et al., (2012). "Intracoronary cardiosphere-derived cells for heart regeneration after myocardial infarction (CADUCEUS): a prospective, randomized phase 1 trial." *Lancet* 379, 895-904 (2012), which is fully incorporated by reference herein.

CDCs are also being tested clinically; data available to date indicate that they are safe, and may lead to improvements in post-ischaemic cardiac structure and function indicative of therapeutic regeneration. Of interest is understanding whether aged hearts benefit from therapy with CDCs. Towards these ends, the Inventors evaluated the effects of CDCs on age-related heart dysfunction and examined the broader rejuvenating potential of CDCs in a well-established rat model of senescence. Further, of interest is understanding whether extracellular vesicles, including exosomes and microvesicles, and their rich milieu of biological factors are capable of mediating age-related effects Cardiosphere-Derived Cells (CDCs)

CDCs are a population of cells generated by manipulating cardiospheres, cultured cells that can be obtained from heart samples, subsequently cultured as explants and suspension cultured cardiospheres. For example, CDCs can be generated by plating cardiospheres on a solid surface which is coated with a substance which encourages adherence of cells to a solid surface of a culture vessel, e.g., fibronectin, and expanding same as an adherent monolayer culture. CDCs can be repeatedly passaged, e.g., passaged two times or more.

Extracellular Vesicles

Extracellular vesicles include lipid bilayer structures generated by cells, and include exosomes, microvesicles, membrane particles, membrane vesicles, exosome-like vesicles, ectosomes, ectosome-like vesicles, or exovesicles. Exosomes are vesicles formed via a specific intracellular pathway involving multivesicular bodies or endosomal-related regions of the plasma membrane of a cell. Exosomes can range in size from approximately 20-150 nm in diameter. In some cases, they have a characteristic buoyant density of approximately 1.1-1.2 g/mL, and a characteristic lipid composition. Their lipid membrane is typically rich in cholesterol and contains sphingomyelin, ceramide, lipid rafts and exposed phosphatidylserine. Exosomes express certain marker proteins, such as integrins and cell adhesion molecules, but generally lack markers of lysosomes, mitochondria, or caveolae. In some embodiments, the exosomes contain cell-derived components, such as but not limited to, proteins, DNA and RNA (e.g., microRNA and noncoding RNA). In some embodiments, exosomes can be obtained from cells obtained from a source that is allogeneic, autologous, xenogeneic, or syngeneic with respect to the recipient of the exosomes.

Certain types of RNA, e.g., microRNA (miRNA), are known to be carried by exosomes. miRNAs function as post-transcriptional regulators, often through binding to complementary sequences on target messenger RNA transcripts (mRNAs), thereby resulting in translational repression, target mRNA degradation and/or gene silencing. For example, miR146a exhibits over a 250-fold increased expression in CDCs, and miR210 is upregulated approximately 30-fold, as compared to the exosomes isolated from normal human dermal fibroblasts.

Methods for preparing exosomes can include the steps of: culturing cardiospheres or CDCs in conditioned media, isolating the cells from the conditioned media, purifying the exosome by, e.g., sequential centrifugation, and optionally, clarifying the exosomes on a density gradient, e.g., sucrose density gradient. In some instances, the isolated and purified exosomes are essentially free of non-exosome components, such as components of cardiospheres or CDCs. Exosomes can be resuspended in a buffer such as a sterile PBS buffer containing 0.01-1% human serum albumin. The exosomes may be frozen and stored for future use.

Extracellular vesicles originating from newt A1 cell line (Newt-EVs) are obtained after filtering A1 cell line CM containing EVs through a 10 KDa pore size filter following a similar process as for CDC-EV production. Newt-EVs are a non-cellular, filter sterilized product obtained from newt A1 cells cultured under defined, serum-free conditions. The final product, composed of secreted EVs and concentrated CM, is formulated in PlasmaLyte A and stored frozen. The frozen final product is ready to use for direct subconjunctival injection after thawing.

Exosomes can be prepared using a commercial kit such as, but not limited to the ExoSpin™ Exosome Purification Kit, Invitrogen® Total Exosome Purification Kit, PureExo® Exosome Isolation Kit, and ExoCap™ Exosome Isolation kit. Methods for isolating exosome from stem cells are found in, e.g., Tan et al., Journal of Extracellular Vesicles, 2:22614 (2013); Ono et al., Sci Signal, 7(332):ra63 (2014) and methods for isolating exosome from cardiosphere-derived cells are found in, e.g., Ibrahim et al., Stem Cell Reports, 2:606-619 (2014), each of which is incorporated by reference herein. Collected exosomes can be concentrated and/or purified using methods known in the art. Specific methodologies include ultracentrifugation, density gradient, HPLC, adherence to substrate based on affinity, or filtration based on size exclusion.

For example, differential ultracentrifugation has become a leading technique wherein secreted exosomes are isolated from the supernatants of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm. Differences in flotation velocity further allows for separation of differentially sized exosomes. In general, exosome sizes will possess a diameter ranging from 30-200 nm, including sizes of 40-100 nm. Further purification may rely on specific properties of the particular exosomes of interest. This includes, e.g., use of immunoadsorption with a protein of interest to select specific vesicles with exoplasmic or outward orientations.

Among current methods, e.g., differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/mL) or application of a discrete sugar cushion in preparation.

Importantly, ultrafiltration can be used to purify exosomes without compromising their biological activity. Membranes with different pore sizes—such as 100 kDa molecular weight cut-off (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. HPLC can also be used to purify exosomes to homogeneouslysized particles and preserve their biological activity as the preparation is maintained at a physiological pH and salt concentration.

Other chemical methods have exploited differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media.

Beyond these techniques relying on general biochemical and biophysical features, focused techniques may be applied to isolate specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

Described herein are compositions and methods related to use of cardiosphere-derived cells and their secreted extracellular vesicles, such as exosomes, microvesicles, or both for anti-aging and rejuvenation. This includes discoveries for effects on heart structure, function, gene expression, and systemic parameters. For animal studies, intra-cardiac injections of neonatal rat CDCs was compared to in old and young rats including evaluation of blood, echocardiographic, haemodynamic and treadmill stress tests. For in vitro studies, human heart progenitors from older donors, or cardiomyocytes from aged rats were exposed to human CDCs or cardiosphere derived cell (CDC) derived exosomes (CDC-XO) from pediatric donors. Transcriptomic analysis revealed that CDCs, but not PBS, recapitulated a youthful pattern of gene expression in the hearts of old. Telomeres in heart cells were longer in CDC-transplanted animals. Cardiosphere-derived cells attenuated hypertrophy by echo, histology confirmed decreases in cardiomyocyte area and myocardial fibrosis. Cardiosphere-derived cell injection improved end-diastolic pressure-volume relationship compared with baseline, and lowered serum brain natriuretic peptide. In CDC-transplanted old rats, exercise capacity increased, body weight decreased and hair regrowth after shaving was more robust. Serum biomarkers of inflammation (IL-10, IL-1b, and IL-6) improved in the CDC group. Young CDCs secrete exosomes which increase telomerase activity, elongate telomere length, and reduce the number of senescent human heart cells in culture.

Described herein are methods and compositions providing significant benefits in preventing, retarding progression or reversing of age-related effects via CDCs and CDC-derived extracellular vesicles, such as CDC-derived exosomes, microvesicles, or both. Certain supporting techniques are described in, for example, U.S. application Ser. Nos. 11/666,685, 12/622,143, 12/622,106, 14/421,355, PCT App. No. PCT/US2013/054732, PCT/US2015/053853, PCT/US2015/054301 and PCT/US2016/035561, which are fully incorporated by reference herein.

Described herein is a method of treating one or more age-related effects including, administering a composition to a subject, wherein administration of the composition treats the subject. In various embodiments, the composition includes cardiosphere-derived cells (CDCs). In various embodiments, the composition includes extracellular vesicles. In various embodiments, the composition includes cardiosphere-derived cell (CDC) derived extracellular vesicles, such as CDC-derived exosomes, microvesicles, or both.

Further described herein is method of modulating one or more age-related effects in a subject, including administering a composition to a subject, wherein administration of the composition modulates the one or more age-related effects in the subject. In various embodiments, the composition includes cardiosphere-derived cells (CDCs). In various embodiments, the composition includes extracellular vesicles. In various embodiments, the composition includes cardiosphere-derived cell (CDC) derived extracellular vesicles, such as CDC-derived exosomes, microvesicles, or both.

Also described herein is a method of improving cardiac performance in a subject. In various embodiments, the method includes administering a composition to a subject, thereby improving cardiac performance in the subject. In various embodiments, the cardiac performance is an age related effect. In various embodiments, the composition includes cardiosphere-derived cells (CDCs). In various embodiments, the composition includes extracellular vesicles. In various embodiments, the composition includes cardiosphere-derived cell (CDC) derived extracellular vesicles, such as CDC-derived exosomes, microvesicles, or both.

Also described herein is a method of reversing senescence in a subject. In various embodiments, the method includes administering a composition to a subject, thereby improving cardiac performance in the subject. In various embodiments, the cardiac performance is an age related effect. In various embodiments, the composition includes cardiosphere-derived cells (CDCs). In various embodiments, the composition includes extracellular vesicles. In various embodiments, the composition includes cardiosphere-derived cell (CDC) derived extracellular vesicles, such as CDC-derived exosomes, microvesicles, or both.

Further described herein is a method of biological rejuvenation including, administering a composition to a subject, thereby promoting biological rejuvenation in the subject. In various embodiments, the composition is obtained from a donor younger than the subject. In various embodiments, the composition includes cardiosphere-derived cells (CDCs). In various embodiments, the composition includes extracellular vesicles. In various embodiments, the composition includes cardiosphere-derived cell (CDC) derived extracellular vesicles, such as CDC-derived exosomes, microvesicles, or both.

In various embodiments, the donor is 10-20, 20-30, 30-40, 40-50, 50-60, 60-70, 70-80, 80 or more years younger than the subject. For example, donor CDCs, CDC-derived extracellular vesicles including exosome, microvesicles, etc. can be obtained from a pediatric subject less than 2 years old and administered to an older subject 55 years or greater to promote biological rejuvenation, such as one or more of reversing senenscence, decreasing senescence-associated secretory phenotype (SASP), improved telomere enzymatic activity, preserved or enhanced telomere length, improved metabolic activity and improved glomerular function.

In various embodiments, biological rejuvenation includes reversing senescence. In various embodiments, biological rejuvenation includes a decrease in senescence-associated secretory phenotype (SASP). In various embodiments, SASP includes elevated expression of one or more of TNF-a, IL-1b, MCP-1, Rantes, M-CSF, alkaline phosphatase, brain natriuretic peptide (BNP), creatinine and/or C-reactive protein (CRP) and a decrease in SASP may include reduced expression of any one of the aforementioned serum markers. In other embodiments, biological rejuvenation includes elevated expression of anti-inflammatory cytokines, such as IL-10. In other embodiments, biological rejuvenation includes a reduction of the number of senescent cells over-expressing and/or accumulating senescence-associated beta-galactosidase (SA-β-GAL), or levels of expression of SA-β-GAL by cells. In other embodiments, biological rejuvenation includes cells expressing enhanced levels of telomerase reverse transcriptase (TERT), increased telomerase (TASE) activity, and/or preserved or enhanced telomere length. In other embodiments, biological rejuvenation includes modulating expression of one or more genes described in FIG. 15D. In various embodiments, biological rejuvenation includes enhanced or preserved blood globulin levels and/or white blood cells. In various embodiments, biological rejuvenation includes maintenance or reduction in body weight. In various embodiments, biological rejuvenation includes preserved or enhanced citrate synthase activity, insulin sensitivity, and/or glucose tolerance. In various embodiments, biological rejuvenation includes a decrease in serum creatinine and blood urea nitrogen. In various embodiments, biological rejuvenation includes improvements in exercise capacity, such as walking distance, hair regrowth, and renal function.

Described herein is a method of treating a subject including administering cardiosphere-derived cells (CDCs) to a subject in need thereof, by thereby treating the subject. Further described herein is a method of treating a subject including administering cardiosphere-derived cell (CDC)-derived extracellular vesicles, such as CDC-derived exosomes, microvesicles, or both, to a subject in need thereof, thereby treating the subject. In various embodiments, the subject in need thereof is afflicted with one or more of osteoporosis, Alzheimer's disease or other types of dementia, immune senescence, wrinkled skin, arthritis and myopathies, atherosclerosis with/without clinically expressed peripheral vascular disease and/or coronary artery disease, diastolic dysfunction with/without heart failure, type 2 diabetes, hair loss, osteoporosis, frailty, age-related cognitive decline, age-related sexual dysfunction, progeria.

In other embodiments of the aforementioned methods, age-related effects include disorders of the bone. In other embodiments, age-related effects include disorders of the musculoskeletal system. In other embodiments, age-related effects include disorders of the cardiovascular system. In other embodiments, age-related effects include disorders of the endocrine system. In other embodiments, age-related effects include disorders of the integumentary system. In other embodiments, age-related effects include disorders of the nervous system. In other embodiments, age-related effects include disorders of the lymphatic system. In other embodiments, age-related effects include disorders of the respiratory system. In other embodiments, age-related effects include disorders of the circulatory system. In other embodiments, age-related effects include disorders of the digestive system. In other embodiments, age-related effects include disorders of the urinary system. Examples of the above include osteoporosis, Alzheimer's disease or other types of dementia, immune senescence, wrinkled skin, arthritis and myopathies, atherosclerosis with/without clinically expressed peripheral vascular disease and/or coronary artery disease, diastolic dysfunction with/without heart failure, type 2 diabetes, among others. Other examples include hair loss, osteoporosis, frailty, age-related cognitive decline, age-related sexual dysfunction, progeria. In various embodiments, the subject is in need of treatment, modulating of an age-related effect, reversing senescence or biological rejuvenation. In various embodiments, the subject is afflicted with one of the aforementioned diseases and/or disorders. In various embodiments, the subject is diagnosed with one of the aforementioned diseases and/or disorders. In other embodiments, age-related effects include disorders of one or more of the aforementioned systems.

In various embodiments, age-related effects include all diseases, conditions and disorders brought on by a reduction in the number of cells in one or more tissues or organs in the human body. In various embodiments, age-related effects include all diseases and disorders brought on by the over-proliferation of cells in the human body. In other embodiments, age-related effects include a reduction in proliferation in cells in one or more tissue or organs in the human body. In other embodiments, age-related effects include a reduction in survival of cells in one or more tissue or organs in the human body. In other embodiments, age-related effects include an increase in apoptosis of cells in one or more tissue or organs in the human body.

In other embodiments, age-related effects include senescent cells overexpressing and/or accumulating senescence-associated beta-galactosidase (SA-β-GAL), or levels of expression of SA-β-GAL by cells. In other embodiments, age-related effects include cells expressing reduced levels of telomerase reverse transcriptase (TERT). In other embodiments, age-related effects include reduced telomerase (TASE) activity. In other embodiments, age-related effects are characterized by telomere length, such as reduced telomere length. In other embodiments, age-related effects include elevated serum marker levels. In various embodiments, serum markers include brain natriuretic peptide (BNP), creatinine a and/or C-reactive protein (CRP). In various embodiments, serum markers include TNF-a, IL-1b, MCP-1, Rantes, M-CSF and alkaline phosphatase. In other embodiments, age-related effects include decreased expression of anti-inflammatory cytokines, such as IL-10. In various embodiments, age related effects include diminished blood globulin levels and/or white blood cells. In various embodiments, age related effects include gain in body weight. In various embodiments, age related effects diminished citrate synthase activity, insulin sensitivity, and/or glucose tolerance. In various embodiments, age related effects include increase in serum creatinine and blood urea nitrogen. In other embodiments of the aforementioned methods, the method treats and/or modulates one, two, three, four, five, six, seven, eight, nine ten or more age-related effects.

In various embodiments, the composition is capable of reducing cellular expression or accumulation of senescence-associated beta-galactosidase (SA-β-GAL), increasing expression of telomerase reverse transcriptase (TERT), and/or increasing telomerase (TASE) activity. In other embodiments, the composition is capable of reducing senescence-associated beta-galactosidase (SA-β-GAL) expressing senescent cells. In other embodiments, the composition is capable of maintaining or extending telomere length. In other embodiments, the composition is capable of reducing serum marker levels. In various embodiments, serum markers include brain natriuretic peptide (BNP), creatinine a and/or C-reactive protein (CRP). In various embodiments, serum markers include TNF-a, IL-1b, MCP-1, Rantes, M-CSF and alkaline phosphatase. In various embodiments, age related effects include diminished blood globulin levels and/or white blood cells. In various embodiments, age related effects include gain in body weight. In various embodiments, age related effects diminished citrate synthase activity, insulin sensitivity, and/or glucose tolerance. In various embodiments, age related effects include increase in serum creatinine and blood urea nitrogen.

In various embodiments, the composition is capable of improving heart diastolic function, including improvements in stiffness and relaxation. In various embodiments, the composition is capable of attenuating hypertrophy, decreasing cardiomyocyte area and myocardial fibrosis. In various embodiments, the composition is capable of improving diastolic dysfunction, and/or end-diastolic pressure-volume relationship compared with baseline. In various embodiments, the composition is capable of improving weight loss (i.e., reducing body weight). In various embodiments, the composition is capable of improving exercise capacity. Improvements in exercise capacity include, for example, an increase in walking distance.

In various embodiments, the subject is more than 55, 60, 65, 70, 75, 80, 85 or more years of age.

In various embodiments, the CDCs are derived from human subjects less than 50-40, 40-30, 30-20, or 20 or fewer years of age. In various embodiments, the CDCs are derived from human pediatric subjects. In various embodiments, the human pediatric subject is less than 18, 17, 16, 15, 14, 13, 12, 11, 10, 9, 8, 7, 6, 5, 4, 3, 2, 1 or fewer years of age. In various embodiments, the extracellular vesicles are exosomes, microvesicles, membrane particles, membrane vesicles, exosome-like vesicles, ectosomes, ectosome-like vesicles, or exovesicles. In various embodiments, the exosomes are CDC-derived exosomes. In various embodiments, the CDC-derived exosomes, microvesicles, or both, s are obtained from CDCs derived from human subjects less than 50-40, 40-30, 30-20, or 20 or fewer years of age. In various embodiments, the CDC-derived exosomes, microvesicles, or both, are obtained from CDCs derived from human pediatric subjects. In various embodiments, the human pediatric subject is less than 18, 17, 16, 15, 14, 13, 12, 11, 10, 9, 8, 7, 6, 5, 4, 3, 2, 1 or fewer years of age. In various embodiments, the CDCs are autologous. In various embodiments, the CDCs are allogenic.

In other embodiments, administration of CDCs includes administration of a therapeutically effective mount of the CDCs. A therapeutically effective mount of the CDCs includes $1\times10^4$ to $1\times10^5$, $1\times10^5$ to $1\times10^6$, and $1\times10^6$ to $1\times10^7$ number of CDCs. For example, it has been demonstrated that 3 mL/$3\times10^5$ human cardiac-derived cells (CDCs), is capable of providing therapeutic benefit. In various embodiments, administration of the extracellular vesicles includes administration of a therapeutically effective amount of the extracellular vesicles. In various embodiments, a therapeutically effective amount include an amount capable of altering gene expression in damaged or dysfunctional tissue, improves viability of the damaged tissue, and/or enhances regeneration or production of new tissue in the individual. In various embodiments, the quantities of extracellular vesicles, including exosomes, microvesicles, or both, that are administered to achieved these effects range from $1\times10^6$ to $1\times10^7$, $1\times10^7$ to $1\times10^8$, $1\times10^8$ to $1\times10^9$, $1\times10^9$ to $1\times10^{10}$, $1\times10^{10}$ to $1\times10^{11}$, $1\times10^{11}$ to $1\times10^{12}$, $1\times10^{12}$ or more. In other embodiments, the numbers of exosomes, microvesicles, or both is relative to the number of cells used in a clinically relevant dose for a cell-therapy method. As mentioned, it has been demonstrated that 3 mL/$3\times10^5$ human cardiac-derived cells (CDCs), is capable of providing therapeutic benefit in intracoronary administration, and therefore, a quantity of extracellular vesicles, including exosomes, microvesicles, or both, as derived from that number of cells in a clinically relevant dose for a cell-therapy method. In various embodiments, administration can be in repeated doses. For example, defining an effective dose range, dosing regimen and route of administration, may be guided by studies using fluorescently labeled exosomes, microvesicles, or both, and measuring target tissue retention, which can be >10×, >50×, or >100× background, as measured 5, 10, 15, 30, or 30 or more min as a screening criterion. In certain embodiments, >100× background measured at 30 mins is a baseline measurement for a low and high dose that is then assessed for safety and bioactivity (e.g., using MM endpoints: scar size, global and regional function). In various embodiments, single doses are compared to two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition.

In other embodiments, administering a composition includes about 1 to about 100 mg exosome protein in a single dose. In various embodiments, the repeated or sequentially-applied doses are provided for treatment of an acute disease and/or condition. In various embodiments, the repeated or sequentially-applied doses are provided for treatment of a chronic disease and/or condition. In other embodiments, administering a composition includes percutaneous injection. In other embodiments, administering a composition includes injection into heart muscle. In other embodiments, administering a composition includes myocardial infusion. In other embodiments, administering a composition includes use of a intracoronary catheter. In other embodiments, administration a composition includes intra-arterial or intravenous delivery. Additional delivery sites include any one or more compartments of the heart, such as myocardium, associated arterial, venous, and/or ventricular locations. For example, CDCs can be injected via left thoracotomy for access to left ventricular cavity for intra-coronary delivery or intramyocardially, divided among four injection sites (anterior, lateral, posterior walls and apex).

In certain embodiments, administration can include delivery to a tissue or organ site that is the same as the site of diseased and/or dysfunctional tissue. In certain embodiments, administration can include delivery to a tissue or organ site that is different from the site or diseased and/or dysfunctional tissue. In other embodiments, extracellular vesicle, including exosomes, microvesicles, or both, therapy is provided in combination with standard therapy for a disease and/or condition. This may include co-administration of the extracellular vesicle, including exosomes, microvesicles, or both, with a therapeutic agent.

Example 1

CDC Culture

Cells from the right ventricular aspect of the interventricular septum can be obtained from healthy hearts of living or deceased tissue donors.

In brief, a sample such as a heart biopsy is minced into small fragments and briefly digested with collagenase. Explants were then cultured on 20 mg/ml fibronectin-coated dishes. Stromal-like flat cells and phase-bright round cells grow out spontaneously from tissue fragments and reach confluence by 2-3 weeks. These cells are harvested using 0.25% trypsin and cultured in suspension on 20 mg/ml poly d-lysine to form self-aggregating cardiospheres. cardiosphere-derived cells (CDCs) are obtained by seeding cardiospheres onto fibronectin-coated dishes and passaged. All cultures are maintained at 5% CO2 at 37° C., using IMDM basic medium supplemented with 20% FBS, 1% penicillin/streptomycin, and 0.1 ml 2-mercaptoethanol.

Example 2

Media Conditioning and Exosome Purification

Figure 1:
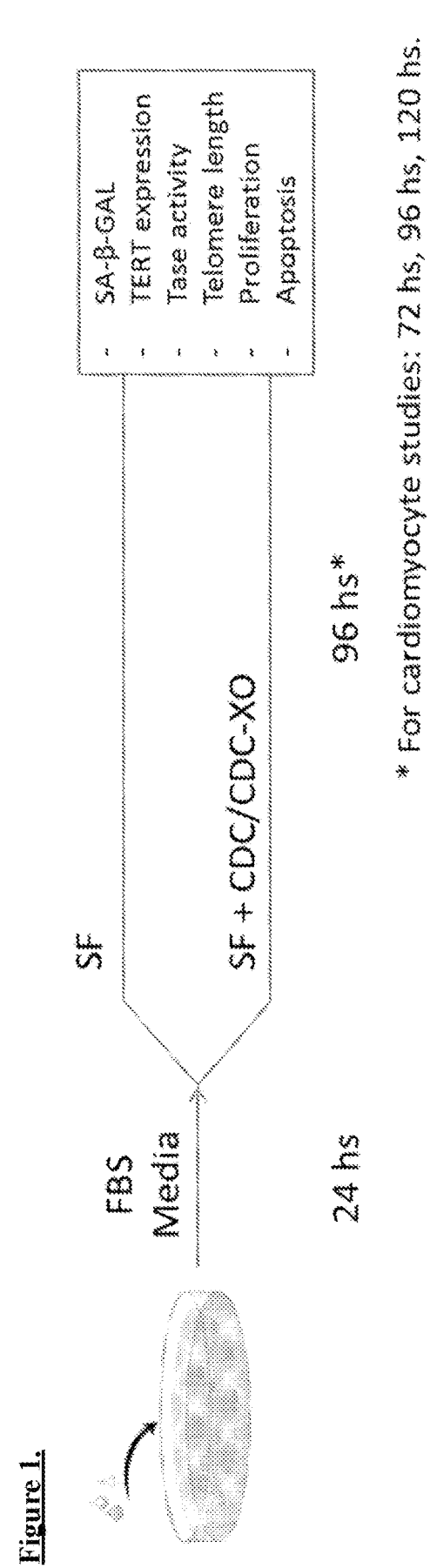
FIG. 1. Experimental Design.

CDCs are conditioned in serum-free media for 15 days at 100% confluence. Aspirated media is then centrifuged at 3,000×g for 15 min to remove cellular debris. Exosomes were then isolated using Exoquick Exosome Precipitation Solution. Experimental design shown in FIG. 1.

Exosome pellets are resuspended in the appropriate media and used for assays. Expression of the conserved exosome marker CD63 is verified using ELISA. RNA content of exosome pellets can also be quantified using a Nanodrop spectrophotometer. For generation of miR-146a-deficient exosomes, CDC are transfected in suspension with miRIDIAN miR-146a hairpin inhibitor or a miRIDIAN hairpin control and seeded on to fibronectin-coated flasks. Exosomes are isolated from serum-free conditioned media (48 hr conditioning).

Example 3

CDC Exosome-Mediated Protection of Telomerase-Telomere Axis

As shown in FIG. 2A, telomerase activity in extracts of heart explant-derived cells from old human donors after 96 hours was determined following telomeric repeat amplification protocol (TRAP) in four groups: the control group incubated with serum-free media (SF); cells co-cultured with young donor CDC alone or together with GW4869 inhibitor of exosome release (CDC and CDC-GW4869, respectively), using transwell membranes; cells co-cultured with young CDC-derived exosomes resuspended in serum-free media. As shown in FIG. 2B, representative images of cells subjected to telomere Q-FISH analysis. Nuclei are stained with DAPI and telomeres with specific CY3-labeled probe (red). Telomere length was analyzed by measuring the integrated optical density (i.o.d.) of the Cy3-channel within the nuclear borders after subtracting the background i.o.d. Results adjusted to the nuclear area are presented as well. Rejuvenation of heart explant-derived cells from old human donors with young human donor CDC-derived exosomes. As shown in FIG. 2C, histochemistry for senescence-associated β-galactosidase (SA-GAL) (blue). Proportion of senescent, SA-GAL+ cells after 96 hours co-incubation time period with young CDC-derived exosomes or serum-free media (SF). CDC-derived exosomes increased the self-assembly potential of the old human heart explant-derived cells. Plated at the same number on day-0, heart explant-derived cells from an old human donor were treated with young CDC-derived exosomes or serum-free (SF) media on day-1. After an additional 72 hours (day-4), cells were collected and quantified, wherein higher number of cells were observed in the CDC-derived exosomes treated group, followed by their resuspension at a density of $3 \times 10^4$ cells/ml in a serum-free media in ultra-low attachment dishes. Newly formed cardiospheres' concentration and size were measured after 72 hours. As shown in FIG. 2D, representative images of formed cardiospheres after 3 days. Concentration of cardiospheres in both groups. Normalized differences in the concentration of the biggest cardiospheres between young CDC-derived exosomes and SF-treated groups. Data are mean±SEM. The lowest number of replicates per experiment was three.

Example 4

CDC-Derived Exosomes-Induced Cell Rejuvenation in Old Rat Cardiomyocyte Culture

Figures 3, 3D:
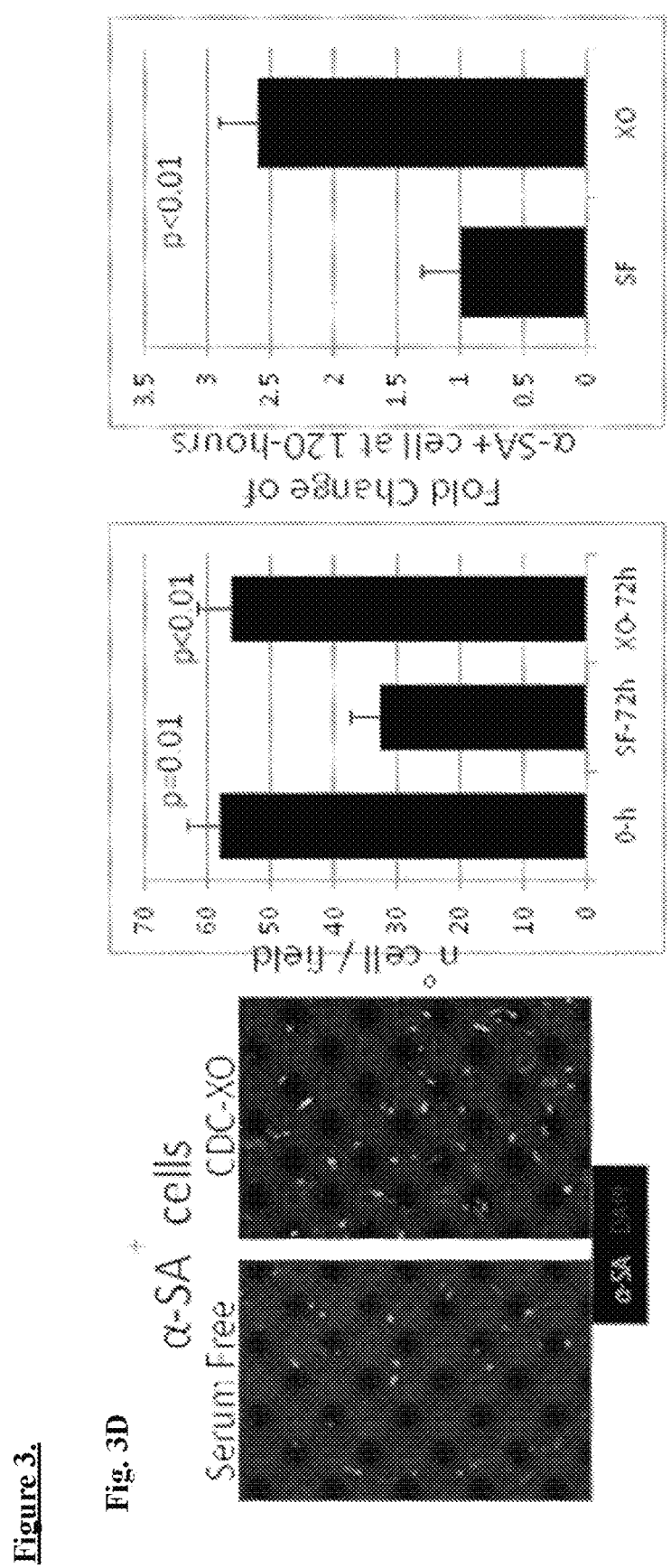
FIG. 3. CDC-derived exosomes-induced cell rejuvenation in old rat cardiomyocyte culture. Two-year old rat cardiomyocytes were isolated by Langendorf procedure and cultured according to a specific protocol with CDC-derived exosomes, resuspended in serum-free (SF) media (treated group) or SF media alone (control group). After 72 hours of culture, other, non-cardiomyocyte-like cells, negative for α-sarcomeric actinin (α-SA) staining, were present in the culture. Those cells were mostly positive for von-Willebrand factor or vimentin. All of them are grouped here under α-sarcomeric actinin-cells.
FIG. 3D. After isolation, rat cardiomyocytes were plated at the same number and density. After 24 hours the media was removed along with all detached cells and replaced by serum-free (SF) media alone (control group) or with resuspended CDC-derived exosomes (treated group). The number of attached (alive) cells with cardiomyocyte shape was calculated after 72 hours. Representative pictures of detached (presumably dead) cells in both groups are also presented. After 120 hours, cells were fixed and stained for α-sarcomeric actinin (α-SA). The number of cardiomyocites after 72 hours in SF and CDC-derived exosomes treated groups. While in the SF group the number of cardiomyocytes decreased 50% over 72 hours, in the CDC-derived exosomes treated group it was maintained practically unchanged. The number of cardiomyocytes was 2.5 fold higher in the CDC-derived exosomes treated group after 120 hours of incubation. Data are mean±SEM. The lowest number of replicates per experiment was three.

Two-year old rat cardiomyocytes were isolated by Langendorf procedure and cultured according to a specific protocol with CDC-derived exosomes, resuspended in serum-free (SF) media (treated group) or SF media alone (control group). After 72 hours of culture, other, non-cardiomyocyte-like cells, negative for α-sarcomeric actinin (α-SA) staining, were present in the culture. Those cells were mostly positive for von-Willebrand factor or vimentin. All of them are grouped here under α-sarcomeric actinin-cells. As shown in FIG. 3A, Histochemistry for senescence-associated β-galactosidase (SA-GAL) (blue) after 72 hours. Importantly, senescent, SA-GAL+ cells were found among the non-cardiomyocyte population of cells. The proportion of SA-GAL+ cells was significantly lower in the CDC-derived exosomes treated cells compared with control group. As shown in FIG. 3B, Immunofluorescence for telomerase reverse transcriptase (TERT) (green), DAPI (blue). TERT protein levels were higher in the CDC-derived exosomes treated cells after 72 hours in both (α-SA+ and α-SA−) types of cells. As shown in FIG. 3C, Telomerase activity in extracts of a whole population of cells was determined following the telomeric repeat amplification protocol, after 72-hours. CDC-derived exosomes treated cells presented a 2 fold increase of telomerase activity. CDC-derived exosomes increase the long-term survival of old rat cardiomyocytes in culture. As shown in FIG. 3D, after isolation, rat cardiomyocytes were plated at the same number and density. After 24 hours the media was removed along with all detached cells and replaced by serum-free (SF) media alone (control group) or with resuspended CDC-derived exosomes (treated group). The number of attached (alive) cells with cardiomyocyte shape was calculated after 72 hours. Representative pictures of detached (presumably dead) cells in both groups are also presented. After 120 hours, cells were fixed and stained for α-sarcomeric actinin (α-SA). The number of cardiomyocites after 72 hours in SF and CDC-derived exosomes treated groups. While in the SF group the number of cardiomyocytes decreased 50% over 72 hours, in the CDC-derived exosomes treated group it was maintained practically unchanged. The number of cardiomyocytes was 2.5 fold higher in the CDC-derived exosomes treated group after 120 hours of incubation. Data are mean±SEM. The lowest number of replicates per experiment was three.

Example 5

Study Protocol

Figure 4:
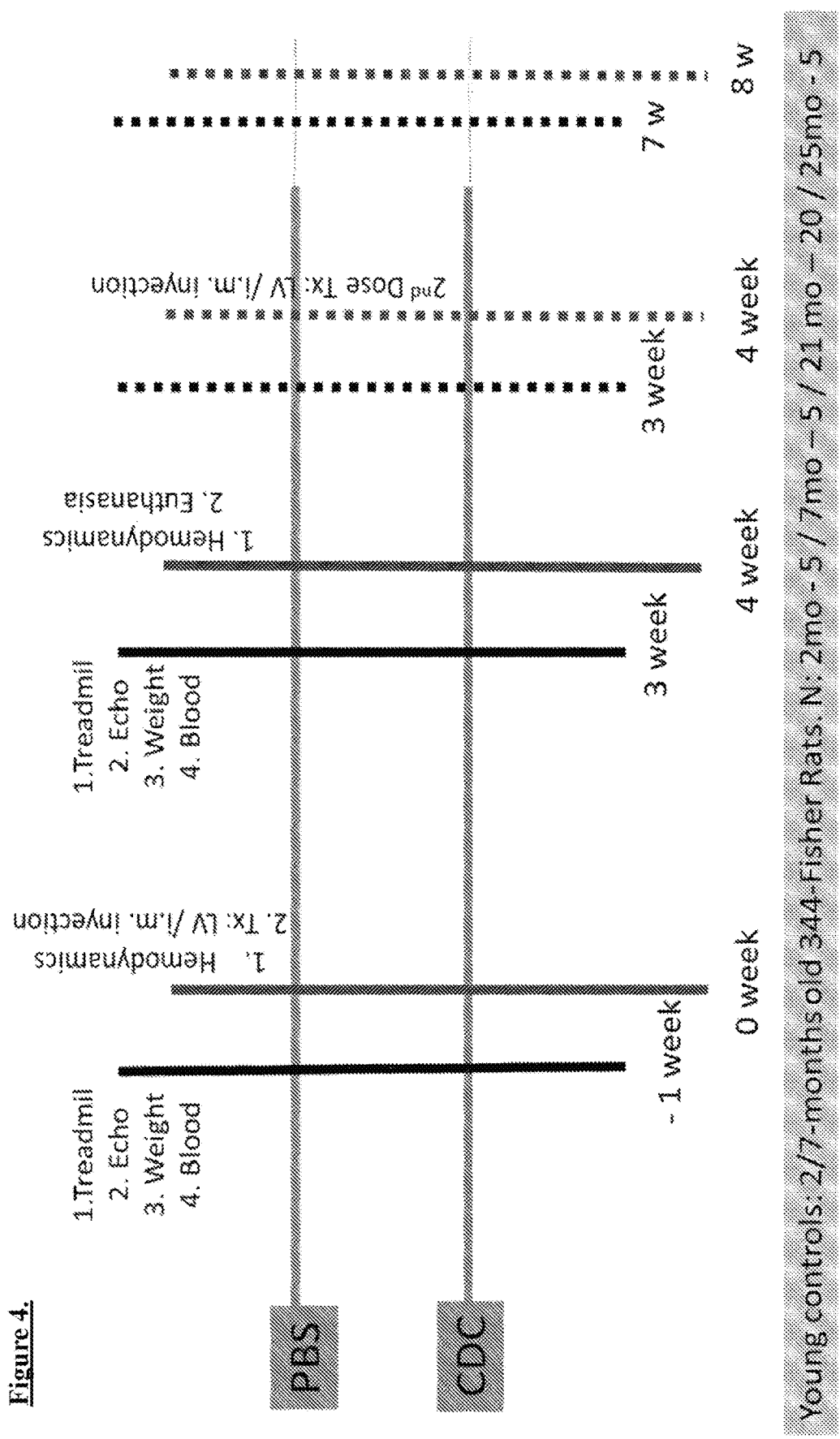
FIG. 4. Study protocol. Experimental group: Twenty five old Fisher 344 rats of 21-months (n=20) and 25-months (n=5). Control group: Five young (2-months old) Fisher 344 rats and five adult (7-months old). Experimental group's animals were allocated in two groups, ensuring similar distribution of the analyzed variables (there were no statistically significant differences between both groups at baseline). 2. Treatment In the actively treated group, neonatal rat cardiosphere-derived cells (CDC), resuspended in phosphate-buffer saline (PBS) were transplanted directly into the hearts of the animals by mean of intramyocardial (7 rats) or left intraventricular injections with aortic clamping (5 rats). As comparator, 8 and 5 rats received PBS alone, by mean of intramyocardial or intraventricular injections, respectively. 3. Procedures One week before surgery, all rats undergone echo evaluation, treadmill exercise testing. They were weighted and blood samples were collected. Open chest surgery was performed a week later. Invasive hemodynamic measurements were obtained, using Millar pressure catheter through transapical approach. Measurements were recorded in baseline conditions and with vena cava compression. Right after the hemodynamic procedure, experimental group of animals received the corresponding dose of CDC or PBS alone. All the procedures were repeated one month later in the experimental group.

Experimental group: Twenty five old Fisher 344 rats of 21-months (n=20) and 25-months (n=5). Control group: Five young (2-months old) Fisher 344 rats and five adult (7-months old). Experimental group's animals were allocated in two groups, ensuring similar distribution of the analyzed variables (there were no statistically significant differences between both groups at baseline). 2. Treatment In the actively treated group, neonatal rat cardiosphere-derived cells (CDC), resuspended in phosphate-buffer saline (PBS) were transplanted directly into the hearts of the animals by mean of intramyocardial (7 rats) or left intra-ventricular injections with aortic clamping (5 rats). As comparator, 8 and 5 rats received PBS alone, by mean of intramyocardial or intraventricular injections, respectively. 3. Procedures One week before surgery, all rats undergone echo evaluation, treadmill exercise testing. They were weighted and blood samples were collected. Open chest surgery was performed a week later. Invasive hemodynamic measurements were obtained, using Millar pressure catheter through transapical approach. Measurements were recorded in baseline conditions and with vena cava compression. Right after the hemodynamic procedure, experimental group of animals received the corresponding dose of CDC or PBS alone. All the procedures were repeated one month later in the experimental group. Study design is shown in FIG. 4.

Example 6

Old Fisher 344 Rats Represent a Good Model of Age-Related Diastolic Dysfunction

Echocardiographic and hemodynamic parameters related with diastolic function (both left ventricular (LV) stiffness and relaxation), and LV structure are presented for rats in different age groups: 2-months (n=5), 7-months (n=5), 21-months (n=20) and 25-months old (n=5). Results indicate a gradual and steady impairment of LV diastolic function after adulthood, associated with increase of the LV mass and end-diastolic diameter. Systolic function remains unchanged after 7-months. Results are shown in FIG. 5.

Example 7

Young CDC Treatment Decreases Left Ventricular Stiffness in Old Animals

Changes in stiffness-related echo-parameters over 1-month period in CDC-transplanted (blue, n=11) and control, PBS (red, n=11) groups. As shown in FIG. 6A, bars represent the change in a parameter between study endpoint and baseline values. As shown in FIG. 6B, E/A and E/E' ratio in adult, 7-months old rats (n=5) and old, 21 and 25-months old rats (n=25) at baseline (black) and one month after treatment with CDC (n=11) or PBS (n=11) As shown in FIG. 6C, representative images of echo-Doppler transmitral flow. Statistical analysis: significant p-values result of T-Student test between groups (black) or paired-test between baseline and endpoint (blue) are shown.

Example 8

Young CDC Transplantation Causes Downward Displacement of the End-Diastolic Pressure-Volume Relationship Changes in left ventricular (LV) end-diastolic pressure-volume relationship (EDPVR) over 1-month period in CDC-transplanted (blue tones) and control, PBS (red tones) groups was measured. EDPVR were obtained from pressure-volume (PV) loop recordings. As shown in FIG. 7A, extrapolation of EDPVR curves at baseline (dark colors) and at endpoint (light colors) in CDC-treated (n=3) and control, PBS-injected (n=5) animals. As shown in FIG. 7B, EDPVR values at baseline (dark colors) and at endpoint (light colors) in CDC-treated (n=4 and 8 at baseline and endpoint, respectively) and control, PBS-injected (n=7 at both timepoints) animals. As shown in FIG. 7C, representative images of PV-loops in CDC-treated and control animals. Statistical analysis: significant p-values result of T-Student test between groups (black) or paired-test between baseline and endpoint (blue) are shown.

Example 9

Young CDC Transplantation Accelerates Left Ventricular Relaxation in Old Animals Changes in left ventricular (LV) relaxation-related hemodynamic parameters over 1-month period in CDC-transplanted (blue tones, n=11) and control, PBS (red tones, n=11) groups. As shown in FIG. 8A. The constant of relaxation, Tau in adult, 7-months old rats (n=5) and old, 21 and 25-months old rats (n=25) at baseline (black) and one month after treatment with CDC or PBS. Values are recorded with the pressure transducer inside of the LV, in stable, baseline conditions. As shown in FIG. 8B, Tau values at baseline in young, 2-months old (black, n=5), adult, 7-months old (black, n=5) and old rats (dark red and blue) and at endpoint (light red and blue) in CDC-treated (n=11) and control, PBS-injected (n=11) animals. Values are obtained from pressure-volume loop recordings. As shown in FIG. 8C, minimum Dp/Dt in adult, 7-months old rats (n=5) and old, 21 and 25-months old rats (n=25) at baseline (black) and one month after treatment with CDC or PBS. Statistical analysis: significant p-values result of T-Student test between groups (black) are shown.

Example 10

Young CDC Transplantation Increases Exercise Capacity in Old Rats with Age-Related Functional Decline Changes in exercise capacity over 1-month period in CDC-transplanted (blue, n=11) and control, PBS (red, n=11) groups. As shown in FIG. 9A, maximum distance on the treadmill in adult, 7-months old rats (n=5) and old, 21 and 25-months old rats (n=25) at baseline (black) and one month after treatment with CDC (n=11) or PBS (n=11) is represented. As shown in FIG. 9B, bars represent the change in the max. Walking distance on the treadmill between study endpoint and baseline values. Statistical analysis: significant p-values result of T-Student test between groups (black) or paired-test between baseline and endpoint (blue) are shown.

Example 11

Young CDC Transplantation Ameliorates, Partly Age-Related, Body Weight Loss

Body weight changes over 1-month period in CDC-transplanted (blue, n=11) and control, PBS (red, n=11) groups. As shown in FIG. 10A, body weight at baseline in adult, 7-months old (n=5) and old rats, 21 and 25-months combined (Old-0 mo, n=25) or individually is represented in black. Changes over one-month period in CDC-transplanted or PBS-injected are represented in blue and red, respectively (n=11, in each group). As shown in FIG. 10B, bars represent weight change between study endpoint and baseline values. Statistical analysis: significant p-values result of T-Student test between groups (black) or paired-test between baseline and endpoint (blue or red) are shown.

Example 12

Changes in Serum Markers

Over 1-month period in CDC-transplanted (blue, n=11) and control, PBS-injected (red, n=11) groups. Serum levels of Brain Natriuretic Peptide (BNP), Creatinine and C-reactive protein (CRP) in adult, 7-months old rats (n=5) and old, 21 and 25-months old rats (n=25) at baseline (black) and one month after treatment (only in the experimental, old animals) with CDC (n=11) or PBS (n=11) are presented. Statistical analysis: significant p-values result of T-Student test between groups (black) or paired-test between baseline and endpoint (blue) are shown in FIG. 11.

Example 13

Young CDC Transplantation Stimulates Hair Regrowth in Old Animals

As shown in FIG. 11, differences in hair regrowth 3-weeks after shaving in old rats transplanted with CDC or injected with placebo. Representative pictures of some of them. This evaluation was done in 12 animals, and in 10 of them visually detectable differences, with more pronounced regrowth among CDC-treated animals, were detected.

Example 14

Animals and In Vivo Study Protocol

Old Fisher 344 rats (21.8±1.6 month old) were obtained from the National Institute of Aging. Younger Fishe 344 rats (4.1±1.5 month old) were purchased from Envigo, Indianapolis, Ind., USA. All F344 lines available in the USA are from the same origin (Columbia University), so share the same genetic background. All animals were studied in accordance with the local guidelines of the Animal Care and Use Committee as published by the National Institute of Health (NIH Publication No. 86-23, revised 1996).

Younger animals were used for the characterization of structural and functional changes related to aging. After initial phenotyping with echocardiography and exercise testing, old animals were divided into two groups that were matched prospectively for comparable baseline properties:

Twelve rats were treated with CDCs, and 11 rats received phosphate-buffered saline (PBS, i.e. vehicle control). Prior to administration of CDCs or PBS, rats underwent invasive haemodynamic evaluation of left ventricular (LV) pressure and volume and aortic pressure. Old animals were evaluated at baseline and 1 month later by echocardiography, invasive haemodynamics, and exercise treadmill testing for structural and functional changes.

Blood samples were collected at the same time points. After 1 month, animals were euthanized and hearts were harvested for further testing. Isolation, expansion, and injection of cardiosphere-derived cells Hearts were excised from 31 Sprague-Dawley neonatal rats to produce CDCs, as described. Rats in the CDC group received $1 \times 10^6$ passage 2 CDCs resuspended in 100 mL of PBS into the LV cavity with simultaneous aortic clamping (5 rats) or intramyocardially, divided among four injection sites (anterior, lateral, posterior walls and apex (7 rats). The same delivery strategies were used in the control group: intracavitary (LV, 5 rats) and intramyocardial (6 rats). No major differences were observed in the end points, and CDCs' cardiac engraftment is similar with the two delivery strategies, so pooled results are presented.

Example 15

Treatment

More specifically for in vivo studies, after initial evaluation with echocardiography and exercise testing, old animals were divided into two groups that were matched prospectively for comparable baseline properties: (1) 12 rats treated with CDCs, (2) 11 rats receiving phosphate buffered saline (PBS, i.e. vehicle control). Allogeneic rat CDCs (1×10⁶ resuspended in 100 μL PBS) or 100 μL PBS alone were injected via a left thoracotomy under general anesthesia (Isoflurane 4-5% for induction followed by 2%). Cells or PBS control were injected into the LV cavity during aortic cross-clamp, over a period of 20 seconds to achieve intracoronary delivery or intramyocardially, divided among four injection sites (anterior, lateral, posterior walls and apex). CDCs were grown from a freshly-explanted Sprague-Dawley neonatal rat heart as described. Briefly, hearts were minced, subjected to enzymatic digestion and then plated on adherent (fibronectin-coated) culture dishes. These explants spontaneously yield monolayer adherent cells (explant-derived cells) which were harvested and plated in suspension culture (105 cells/mL on poly-D-lysine-coated dishes) to enable the self-assembly of three-dimensional cardiospheres. Subsequent replating of these cardiospheres on adherent culture dishes yielded CDCs. CDCs at passage 2 were used for all experiments.

Example 16

Cardiac Echocardiography

Echocardiography was performed at baseline, before treatment, and 1 mo later after treatment to assess systolic and diastolic functions (Vevo 770, Visual Sonics, Toronto, Ontario, Canada), under controlled general anesthesia (Isoflurane 4% for induction followed by 2%) and spontaneous respiration. Two-dimensional long axis and short axis (at the papillary muscle level) LV images were obtained. M-mode tracings were recorded through the anterior and posterior LV walls at the papillary muscle level to measure LV dimension, and LV anterior and posterior wall thickness at end diastole. Pulse-wave Doppler spectra (E and A waves) of mitral inflow were recorded from the apical 4-chamber view, with the sample volume placed near the tips of the mitral leaflets and adjusted to the position at which velocity was maximal and the flow pattern laminar. E/A ratio was used to assess diastolic function as described. Systolic function was assessed by LV ejection fraction (LVEF) and fractional area change (FAC) calculated from the short axis view. Tissue Doppler imaging was used to obtain the velocity of the early diastolic E' wave at the septal mitral annulus.

Example 17

Exercise Test

Rats were acclimated to the treadmill by walking at a speed of 5 m/min during 5 minutes before each test, on a 3-lane Columbus Instruments treadmill. The protocol for the maximal exercise capacity test consisted in warming at 5 m/min for 5 minutes followed by 3 m/min increases in speed every 3 minutes until the rat reached exhaustion. Rats were considered exhausted when they failed to stay off of a shock grids. The grade of the treadmill was set at 15° during whole duration of the test.

Example 18

Blood Pressure and Hemodynamic Measurements

Hemodynamic measurements were performed at baseline, before treatment, and 1 mo after treatment. Under general anesthesia (Isoflurane 4-5% for induction followed by 2%), rats were intubated and maintained under controlled respiration. Left thoracotomy was performed and the heart apex was exposed. 2F conductance catheter (SPR-838, Millar, Houston, Tex., USA) was then introduced into the LV cavity using transapical approach. Blood pressure was recorded after initial stabilization with the tip of the catheter placed in the ascending aorta. After the catheter was pooled back and once inside of the LV cavity end systolic and end diastolic pressures and volumes were recorded. Data for determination of LV end-diastolic and end-systolic pressure-volume relationships (EDPVR and ESPVR, respectively) were obtained by temporary inferior vena cava occlusion. The time constant of isovolumetric LV pressure fall (Tau) was calculated as described. All data were collected and analyzed using pressure-volume analysis software (LabChart, ADInstruments, Colorado Springs, Colo., USA).

Example 19

Collagen Content Quantification

To measure fibrosis, 5 μm heart sections from middle and basal parts of the ventricles were used for histology. Masson's trichrome staining (HT15 Trichrome Stain [Masson] Kit; Sigma-Aldrich, St. Louis, Mo.) was used to detect collagen deposition. Regional segments were cut as illustrated (FIG. 21) to increase the efficiency of the analysis. The collagen content was calculated as a percentage of the area of each segment using Image J software.

Example 20

Immunostaining

For cardiomyocyte cross sectional area, slides were immunostained with wheat-germ agglutinin (Alexa Fluor 647 conjugated, Thermo-Fisher) and α-sarcomeric actin (α-SA) (Abcam 72592). Cross-sectional area was measured only in regions where cardiomyocytes met the following 3 criteria: cellular cross-section present; visible nuclei located in the center of the cell; and intact cell borders. The appropriate fluorescently-conjugated secondary antibodies (Invitrogen) were applied and all slides were counterstained for DAPI (Molecular Probes). Five to 10 images per slide were imaged at ×20 magnification using a confocal laser microscope and analyzed using Image-J software.

Example 21

Telomere Length Assay

To measure telomere length, the multiple hearts from each treatment group were fixed in 4% paraformaldehyde and then frozen in OCT media (Tissue-Tek) for cryosectioning. 5 μm sections were cut via cryotome by the Cedars-Sinai Pathology Core and mounted onto glass slides. The cardiac tissue was permeabilized and telomeres were stained using Fluorescent In Situ Hybridization (Telomere PNA FISH Kit/Cy3; DAKO). Rabbit primary antibodies raised against rat sarcomeric α-actinin (1:100; Abcam) and goat anti-rabbit FITC-conjugated secondary antibodies (1:400; Abcam) were used to identify cardiomyocytes. DAPI was used as a nuclear stain. 100× images (20-40 images per animal) were taken using the BIOREV Keyance BZ-9000 fluorescent microscope, under identical imaging settings between slides. Telomere length was analyzed using ImageJ (NIH), by measuring the integrated optical density of the Cy3-channel within the nuclear borders, running perpendicular to the image plane after subtracting the background and adjusting to the nuclei area.

Example 22

Tissue and Blood Collection

Blood samples (1 mL) were collected at baseline and 1 mo later via external jugular vein puncture. Serum was separated, aliquoted and frozen at −80° C. At endpoint, after hemodynamic measurements, hearts were arrested in diastole (intra-ventricular injection of KCl) and excised. For histology, heart slices were embedded in OCT compound (Sakura Finetek, Torrance, Calif., USA) and frozen at −80° C. For protein and RNA quantification, tissue samples were maintained in RNA and protein stabilization reagent (Allprotect, Qiagen, Venlo, Netherlands) and frozen at −80° C.

Example 23

Serum Markers

Inflammatory cytokines were quantified in the serum using a commercially available rat adipokine array kit (R&D System, Inc. Minneapolis, Minn., USA). Sera from 9 young rats, 8 old rats at baseline and 7 and 7 rats 1 month after injection of PBS or CDCs, respectively, were used. All values were normalized to the old group for the comparison between young and old rats and to the old-PBS for the comparison between old-CDC and old-PBS groups. Serum levels of BNP, creatinine, BUN and GDF-11 were analyzed by independent commercially available rat ELISA kits (MyBioSource, Inc. San Diego, Calif., USA). The number of animals in each group and the time points when the samples were analyzed are specified on each figure.

Example 24

RNA Isolation and Semi-Quantitative Reverse Transcriptase Polymerase Chain Reaction Expression RNA was isolated from heart samples with RNA easy kit (Qiagen, Venlo, Netherlands). To compare the gene expression levels among different groups SYBR Green technology (Applied Biosystems) was applied. cDNA was synthesized from mRNA using a RT2 First Strand Synthesis Kit (QIAGEN) according to the manufacturer's protocol. The resulting cDNA was standardized across samples and loaded into the predesigned Rat Aging and Rat Cellular Senescence RT2 Profiler PCR Arrays (QIAGEN) plates. Gene expression was then amplified over the course of 40 cycles and analyzed by ΔΔ Ct.

Example 25

Effect on Hair Regrowth

Chest ventral and lateral walls were shaved before surgery. After 3 weeks, hair regrowth was analyzed by measuring the area of impaired regrowth areas (areas of low hair density) and expressed as a percentage of the total shaved area using Image J software (FIG. 23).

Example 26

Human Heart Cell Isolation and Culturing

More specifically for in vitro studies, when minced human heart tissue is grown in primary culture, it spontaneously gives rise to monolayers of cardiac stromal cells and progenitor cells (CSPCs). Cells are isolated from hearts of living or deceased tissue donors, with tissued minced into small fragments, digested with collagenase, and cultured on fibronectin-coated dishes. CSPCs grow spontaneously from the tissue fragments and reach confluence by 2-3 weeks, at which time they are harvested using 0.25% trypsin (GIBCO), purified from tissue and cell debris and re-plated as needed. CSPCs are further processed to yield CDCs. Cultures were maintained in 5% $CO_2$ at 37° C., using IMDM basic medium (GIBCO) supplemented with 20% FBS (Hyclone), 1% penicillin/streptomycin, and 0.1 ml 2-mercaptoethanol. All protocols were approved by the institutional review board for human subjects research.

Example 27

Isolation and Characterization CDC-Derived Exosomes

Extracellular vesicles, such as cardiosphere derived exosomes (CDC-XO) and also microvesicles, were harvested from young CDCs at passage 4, from serum-free media conditioned by CDCs for 15 days at 90% confluence. Media was then subjected to two successive centrifugation steps to remove cellular debris: 2,000×g for 20 min and 10000×g for 30 min. The resulting supernatant was precipitated by polyethylene glycol (ExoQuick$^{TC}$), which yields high quantities of purified exosomes, after overnight incubation at 4° C. Exosomes were then isolated by centrifugation at 2000 g for 30 min, resuspended and quantified for particle concentration and size and protein concentration. Total protein concentration-adjusted doses of CDC-XO resuspended in serum-free media were used.

Example 28

Rat Cardiac Cell Isolation

Cardiomyocytes were isolated from old rats (24 months, 300-450 g) by enzymatic dissociation of the ventricles. On the first day, the FBS-supplemented media was replaced by serum-free media with or without resuspended young CDC-XO.

Example 29

Telomerase Activity Assay

Telomerase activity was evaluated in old CSPCs and old rat cardiomyocyte culture cells after 96 and 72 hours, respectively, in three different conditions: 1. After co-incubation with young CDCs using transwell permeable supports (Costar$^R$); 2. After priming with young CDC-XO resuspended in serum-free-media; 3. Control group, cells cultured directly in serum-free-media. The TeloTAGGG Telomerase PCR ELISA$^{PLUS}$ kit (Sigma-Aldrich) was used, with modifications.

Example 30

Telomere Length Assessment

Telomerase length was assessed via Cy3-labeled Fluorescent In Situ Hybridization (FISH). Cells receiving either CDC-XO or serum-free control were enzymatically harvested (TrypLE Select, Gibco) and digestion halted with CDC media plus 20% FBS. Telomere length was analyzed by measuring the integrated optical density of the Cy3-channel within the nuclear borders (ImageJ, NIH).

Example 31

Detection of Senescent Cells

Senescent cells were detected by the presence of senescence-associated β-galactosidase activity (SA-β-GAL; Abcam). When cell density was high and cells borders weren't clearly identifiable, SA-β-GAL positive areas were quantified with Image J; when the density was lower and the cells were non-confluent, the positive cell number/optical field was reported.

Example 32

Statistical Analysis

The main end-points of the study reflected functional improvement of the heart: E/A and Tau. Based on the Inventors' previous results (~10±5% of differences in the functional tests between experimental groups), a sample size of 10 animals per group (assuming a 5% significance level and an 80% power level) was estimated, using a statistical software program (GB-Stat Version 10.0, Dynamic Microsystems Inc). Assuming a 20% age-related mortality in these old rats and 10% post-procedure (post-thoracotomy) mortality, observed in the Inventors' lab, the Inventors acquired 28 animals for the Inventors' experimental groups. Five rats died before starting the study, the remaining 23 were allocated to receive CDCs (n=12) or PBS (n=11). One rat from the CDC group died right after the surgical procedure (same day), so was not considered for the final analysis. All changes/differences in functional tests at end-point or paired analysis were performed on 11 rats in each group. For the histological evaluations, the Inventors based the Inventors' estimation on previous results with CDCs on fibrosis. The anticipated standard deviation was 2.4% and the anticipated magnitude of the difference was 4.5%. Thus, the estimated sample size was of ~5-6 per group, for an assessment by student's T test with an alpha value of 0.05 and beta value of at least 0.8. As the Inventors initially had one more rat in the CDC group, 6 and 5 rats' samples were picked randomly from CDC and PBS groups, respectively, to analyze fibrosis, cross sectional area and telomere length. For studies using isolated RNA (gene expression) or protein (inflammatory markers), with no previous information on possible expected differences, the Inventors decided to use higher number than for histological studies but limited by the expensive costs of these tests, the Inventors picked ~7 samples per group. The only analysis where a lower than an initially estimated sample size was used were: PV-loops (only those records with an appropriate quality were considered) and serum creatinine/BUN tests (because of a limited serum volume in some animals).

Gene expression was analyzed online, using QIAGEN data analysis center (http://www.qiagen.com/us/shop/genes-and-pathways/data-analysis-center-overview-page/rt2-profiler-per-arrays-data-analysis-center). To minimize the potential noise introduced by measurements below detection threshold, mRNAs with Ct value>35 in all groups were considered as undetected. Specifically, the expression levels of mRNAs were evaluated by a comparative Ct method using median of expressed housekeeping mRNAs for normalization. The data were only used if the output passed the quality control test with respect to array genomic DNA contamination, reproducibility and reverse transcriptase efficiency. Fold-change calculations or gene expression ratios were calculated using the classic, well-established, and widely adopted ΔΔCT method. The p-values were calculated using a Student's t-test (two-tail distribution and equal variances between the two samples) on the replicate 2ΔCT values for each gene in each group (old-CDC and Young) compared to the control group (old-PBS). The p-values less than 0.05 were indicated as significant. Each sample was used in duplicate or triplicate for validation purposes.

All results are presented as mean±standard deviation (±SEM in figures) or percentages, for continuous and categorical variables, respectively. Significance of differences was assessed by Student t-test or with one-way Analysis Of Variance (ANOVA) in case of multiple groups if the distribution of the variable was normal; otherwise, the Mann-Whitney or Kruskal-Wallis tests were used. Paired t-test was used to determine significance between baseline and end point in the same group of animals. Age-related changes in three age groups were estimated by linear regression analysis. Based on the Inventors' previous results (10±5% of differences in the functional tests between experimental groups), a sample size of 10 animals per group (assuming a 5% significance level and an 80% power level) was estimated, using a statistical software program (GB-Stat Version 10.0, Dynamic Microsystems Inc). Gene expression was analysed online, using QIAGEN data analysis centre [qiagen.com/us/shop/genes-and-pathways/data-analysis-center-overview-page/rt2-profiler-per-arrays-data-analysis-center (August 2017)].

All probability values reported are two-sided, with P<0.05 considered significant. IBM SPSS Statistics was used for all analyses. For in vitro studies, the lowest number of replicates per experiment was 3.

Example 33

Results

The Inventors first characterized the animal model in terms of age-related structural and functional changes (FIG. 20). Aging was associated with progressive diastolic dysfunction (FIG. 21A-FIG. 20E and FIG. 20N) with preserved systolic function (FIG. 20H, FIG. 20I, and FIG. 20N), and steady increases of LV mass and LV diameter (FIG. 20F, FIG. 20G, and FIG. 20N). Blood pressure did not differ significantly among age groups (FIG. 20J and FIG. 20N), but exercise capacity decreased with aging (FIG. 20M and FIG. 20N).

Functional improvement of the heart: cardiosphere-derived cells decrease stiffness and improve relaxation of the left ventricle FIG. 13A shows representative images of transmitral blood flow and tissue Doppler in PBS- and CDC-injected rats. After 1 month, old rats that had been transplanted with CDCs (but not those that had received only PBS) showed a decrease of E/A (from 4.2±1.8 at baseline to 2.1±0.4, P<0.01) and E/E' ratios (from 22.6±5.2 at baseline to 16.3±4.3, P=0.05), back towards values seen in young rats (FIG. 13B). Serial invasive haemodynamic measurements confirmed the echocardiographic findings. FIG. 13C shows examples of pressure-volume loops before and 1 month after injection of PBS or CDCs in old animals. Such data were used to derive the slope of the LV end-diastolic pressure-volume relationship (EDPVR). Cardiosphere-derived cell treatment (but not PBS) decreased EDPVR after 1 month (FIG. 13D, upper panel), indicating improved stiffness. The time constant of relaxation Tau (FIG. 13D, lower panel) was abbreviated in CDC-transplanted rats 1 month post injection (22.2±3.5 ms vs. 26.9±6.0 ms in PBS, P<0.05, respectively). Minimum dP/dT values showed a similar trend as Tau, but did not reach statistical significance. No significant differences or evolving changes were observed in LV systolic function, which was normal in both groups at baseline (fractional shortening of 38% and ejection fraction of 66%, with no differences in the slope of the end-systolic pressure-volume relationship between groups).

TABLE 1

Results of all functional studies in both groups, CDC-transplanted (n = 11) and PBS-injected (n = 11) rats.

| Variable | | PBS | CDC | p-value PBS vs CDC |
|---|---|---|---|---|
| Echocardiography | | | | |
| ED-LVD (mm) | Baseline | 7.8 ± 0.5 | 7.6 ± 0.7 | 0.71 |
| | 1-month | 7.8 ± 0.3 | 7.8 ± 0.4 | 0.43 |
| | p-value Baseline vs 1-mo | 0.898 | 0.413 | |
| ES-LVD (mm) | Baseline | 4.8 ± 0.5 | 4.6 ± 0.6 | 0.78 |
| | 1-month | 4.9 ± 0.4 | 4.9 ± 0.6 | 0.56 |
| | p-value Baseline vs 1-mo | 0.81 | 0.112 | |
| IVS (mm) | Baseline | 1.4 ± 0.08 | 1.5 ± 0.1 | 0.41 |
| | 1-month | 1.4 ± 0.2 | 1.3 ± 0.07 | 0.20 |
| | p-value Baseline vs 1-mo | 0.637 | 0.001 | |
| PW (mm) | Baseline | 1.5 ± 0.1 | 1.6 ± 0.1 | 0.21 |
| | 1-month | 1.6 ± 0.2 | 1.4 ± 0.1 | 0.16 |
| | p-value Baseline vs 1-mo | 0.630 | 0.002 | |
| LV Mass (mg) | Baseline | 651.1 ± 23.2 | 700.6 ± 35.1 | |
| | 1-month | 657 ± 36.1 | 633.3 ± 19.8 | 0.91 |
| | p-value Baseline vs 1-mo | 0.908 | 0.08 | |
| E' (mm/s) | Baseline | 44.2 ± 12.2 | 42.9 ± 7.2 | 0.75 |
| | 1-month | 52.4 ± 17.4 | 68.5 ± 20.4 | 0.05 |
| | p-value Baseline vs 1-mo | 0.33 | 0.009 | |
| A (mm/s) | Baseline | 385.5 ± 194.3 | 269.4 ± 103.5 | 0.07 |
| | 1-month | 453.0 ± 237.7 | 570.9 ± 121.6 | 0.14 |
| | p-value Baseline vs 1-mo | 0.78 | <0.001 | |
| E/A | Baseline | 3.0 ± 1.5 | 4.2 ± 1.8 | 0.08 |
| | 1-month | 2.9 ± 1.9 | 2.1 ± 0.4 | 0.19 |
| | p-value Baseline vs 1-mo | 0.61 | 0.002 | |
| E/E' | Baseline | 22.9 ± 7.3 | 22.6 ± 5.2 | 0.89 |
| | 1-month | 20.5 ± 6.5 | 16.3 ± 4.3 | 0.08 |
| | p-value Baseline vs 1-mo | 0.53 | 0.05 | |
| LV-EF (%) | Baseline | 65.7 ± 4.1 | 67.3 ± 6.2 | 0.46 |
| | 1-month | 64.2 ± 5.3 | 67.0 ± 10.0 | 0.42 |
| | p-value Baseline vs 1-mo | 0.33 | 0.89 | |
| LV-FS (%) | Baseline | 37.5 ± 3.1 | 38.9 ± 5.0 | 0.39 |
| | 1-month | 36.5 ± 4.2 | 39.3 ± 8.1 | 0.32 |
| | p-value Baseline vs 1-mo | 0.39 | 0.61 | |
| Hemodynamic | | | | |
| Tau (ms) | Baseline | 24.6 ± 5.9 | 23.4 ± 4.1 | 0.57 |
| | 1-month | 26.9 ± 6.0 | 22.2 ± 3.5 | 0.04 |
| | p-value Baseline vs 1-mo | 0.28 | 0.68 | |
| Min Dp/Dt | Baseline | −4,475.8 ± 1125.9 | −4,169.6 ± 951.9 | 0.13 |
| | 1-month | −3,945.8 ± 1328.4 | −4,664.4 ± 1503.2 | 0.25 |
| | p-value Baseline vs 1-mo | 0.96 | 0.59 | |
| Max Dp/Dt | Baseline | 4,518.8 ± 1332.7 | 4,961.8 ± 888.7 | 0.28 |
| | 1-month | 4,583.5 ± 1290.7 | 5,067.1 ± 1188.9 | 0.38 |
| | p-value Baseline vs 1-mo | 0.91 | 0.83 | |

TABLE 1-continued

Results of all functional studies in both groups, CDC-transplanted (n = 11) and PBS-injected (n = 11) rats.

| Variable | | PBS | CDC | p-value PBS vs CDC |
|---|---|---|---|---|
| EDPVR (mmHg/10uL) | Baseline | 3.9 ± 3.3 | 5.2 ± 1.7 | 0.31 |
| | 1-month | 4.6 ± 5.5 | 2.1 ± 1.1 | 0.12 |
| | p-value Baseline vs 1-mo | 0.77 | 0.01 | |
| Treadmill | | | | |
| Max Distance | Baseline | 123.6 ± 23.7 | 107.8 ± 25.5 | 0.50 |
| | 1-month | 116.4 ± 19.8 | 128.6 ± 12.4 | 0.01 |
| | p-value Baseline vs 1-mo | 0.51 | 0.04 | |
| Max Speed | Baseline | 14.7 ± 1.5 | 14.1 ± 1.6 | 0.47 |
| | 1-month | 14.1 ± 1.3 | 15.7 ± 1.5 | 0.02 |
| | p-value Baseline vs 1-mo | 0.44 | 0.04 | |

ED-LVD: end-diastolic left ventricular diameter;
ES-LVD: end-systolic left ventricular diameter;
IVS: interventricular septum;
PW: posterior wall;
LV: left ventricule;
EF: ejection fraction;
FS: fractional shortening;
EDPVR: end-diastolic pressure-volume relationship.
Significant p-values are highlighted in red and borderline values - in blue. Values are mean ± SD.

Structural changes of the heart: cardiosphere-derived cells regress left ventricular hypertrophy and are associated with less fibrosis FIG. 14A shows typical LV M-Mode images before and 1 month after injection of PBS or CDCs. After intervention in old rats, wall thickness decreased in the CDC group (P<0.01 for interventricular septum and LV posterior wall) with borderline reduction of LV mass (FIG. 14B), but PBS injection had no evident effect. The echocardiographic changes were supported by the histological finding of smaller cross-sectional cardiomyocyte area after CDC vs. PBS injection (P<0.0001, FIGS. 14C and 14D). Similar reductions in cardiomyocyte hypertrophy with CDCs have been observed in post-ischaemic heart failure. Additionally, cardiac fibrosis, assayed by Masson's trichrome staining (FIGS. 14E and F14F), was reduced in rats transplanted with CDCs compared with control. FIG. 14F shows that overall fractional fibrotic area dropped from 7.3% vs. 4.4% (P<0.05), an effect which reflected reductions of scar throughout the heart. Finally, serum levels of brain natriuretic peptide (BNP), which is known to rise in human aging, increased with age in the Inventors' study, but further increases post-injection were blunted by treatment with CDCs (FIG. 14G).

Example 34

Cardiosphere-Derived Cells Induce Biological Rejuvenation of the Heart

The Inventors analyzed the expression of 168 genes implicated in tissue aging and cellular senescence pathways in whole-heart extracts from young rats, and from old rats treated with CDCs or PBS (FIG. 15). Comparing the transcriptomes of CDC- and PBS-injected rats, significant differences were detected in 37% of the genes (FIGS. 15A and 15B). Most of the CDC-related changes (85.5%) directionally recapitulated the gene expression patterns of young animals (FIG. 15C). Among the genes affected, those implicated in cell cycle control (e.g., E2f1 and Rbl1) and immune response (e.g., Fcer1g and Lrf7) figured most prominently (FIG. 15D).

The Inventors found that cardiac telomeres were longer at study end-point in CDC-injected animals (P<0.0001 vs. PBS controls; FIG. 16A and B16). About half of cells in the PBS group had extremely short telomeres (within the lowest quartile of length), compared with only 10% in CDC-injected rats (FIG. 16Biii). In contrast, 40% of heart cells in the CDC group were within the highest quartile of telomere length (compared with <10% in PBS-injected animals). Findings were similar when telomere length was evaluated specifically in cardiomyocytes (FIG. 16C), with longer mean length in CDC-injected rats (P<0.0001 vs. PBS, FIG. 16Cii) and an inverse telomere length distribution between the two groups (P<0.0001, FIG. 16Ciii).

Example 35

Cardiosphere-Derived Cells Cause Favourable Systemic Effects

Aging is associated with a marked decrease of exercise capacity (P<0.001, see Supplementary material online, FIG. 20M). In the aged rats, treadmill exercise capacity increased by 25% in the month after CDC injection (107.8±25.5 m to 128.6±12.4 m; P<0.05), but changed little in PBS-injected old animals (FIG. 17A). Weight loss secondary to sarcopenia or cachexia, compounded by surgery, also appeared to be responsive to CDCs: PBS-injected rats lost 30% more body weight in the post-operative month compared with CDC-transplanted animals (P=0.05, FIG. 17B). As systemic biomarkers of inflammation, interleukins (IL) 6, and 1b are known components of the senescence-associated secretory phenotype (SASP) which is implicated in propagation of the aging process. Serum levels of these ILs and other inflammatory cytokines were higher in old rats than in young animals (FIG. 22A), but CDC therapy lowered IL-1b and IL-6 levels (by 25% and 60%, respectively) compared with control rats at the study end point (FIG. 17C). In eight animals, serum samples were available both at baseline and study end point, showing a five-fold decrease of IL-6 levels in CDC-treated rats. Heart and renal functions are closely correlated in the clinical entity of cardio-renal syndrome, which is prominent in elderly patients. Both serum creatinine (sCr) and blood urea nitrogen (BUN) levels were higher in old than in young rats (FIG. 22C and FIG. 22D). Levels of sCr decreased in CDC-injected old rats (P<0.05) over the month post-intervention, despite less body weight loss than in PBS-injected animals. Taken together with the minimal decrease of BUN levels in the CDC group versus an increase in the control rats (FIG. 22B), estimated glomerular filtration rate increased in the CDC-transplanted animals (FIG. 17D). Also, the Inventors discovered an unexpected increase in the rate of hair regrowth after shaving in animals that had received CDCs relative to those injected with PBS (FIGS. 17E and 17F; FIG. 23). The improvements in exercise capacity, body mass, inflammatory cytokines, renal function and hair growth reveal that the rejuvenating benefits of CDCs are not limited to, or specific for, the cardiovascular system. Finally, serum levels of GDF 11, proposed as a systemic rejuvenating factor were comparable in the Inventors' experimental groups (FIG. 24), making it unlikely that this molecule plays an important role in CDC associated rejuvenation.

Example 36

Exosomes as Mediators of Anti-Senescent Effects of Cardiosphere-Derived Cells

The Inventors' data are consistent with the understanding that telomerase activation and related telomere elongation underlie the anti-senescent effects in old rats. Using human cells to exclude rodent-specific effects and to assay the potential anti-aging effects of young CDCs on old human heart cells, the Inventors primed CSPCs obtained from >55-year-old donors with young (donors<2 years of age) CDCs, resuspended in serum free conditioned media, using a transwell co-culture system.

Telomerase was almost inactive in old CSPCs but its activity increased four-fold after 96 h of transwell culture with young CDCs, compared with control (FIG. 18A). Many, if not most, effects of CDCs are mediated by secreted exosomes, microvesicles, or both. A blocker of exosome release, GW4869 (20 uM), abrogated the telomerase-activating effect of CDCs (FIG. 18A). Furthermore, old CSPCs primed with exosomes isolated from young CDCs (CDC-XO) exhibited a sixfold increase of telomerase activity (FIG. 6A). Both lines of evidence support the notion that exosomes, microvesicles, or both mediate young CDC-induced telomerase activation.

One of the main functions of telomerase is telomere lengthening with associated cellular rejuvenation. The Inventors further tested both effects in old CSPCs. Telomeres were longer (FIG. 18B) and the number of senescence-associated b-galactosidase positive (SAGALþ) CSPCs were lower (FIG. 18C) in young CDC-XO primed cells compared with control cells after 96 h. To investigate whether these effects are seen in working myocardial cells, the Inventors tested the effects of young CDC-XOon ventricular cardiomyocytes isolated from old (24 month old) rats (FIG. 25). The proportion of senescent SA-GALþ cells was lower in CDC-XO-primed cardiomyocytes than in control cells (P<0.05; FIG. 25A), accompanied by a two-fold increase of borderline statistical significance in telomerase activity after 72 h (FIG. 25B). The Inventors analyzed short- and long-term survival of a-sarcomeric actinin positive cardiomyocytes and observed a progressive decrease in the number of cells in the control group after 24 h, but preservation of the initial number of plated cardiomyocytes in the CDC-XO-primed group (FIG. 25C).

Example 37

Discussion

Here the Inventors discovered the ability of cell therapy to attenuate age-related diastolic dysfunction and achieve favorable structural changes. Unexpectedly, the Inventors also found broadly favorable effects of CDCs in old animals, despite the fact that the cells were delivered to the heart. The in vivo findings are supported by in vitro demonstration of novel exosome-mediated anti-senescent properties, yielding mechanistic insights into the anti-aging effects of young CDCs (FIG. 19). Cardiac and vascular aging prominently affect diastolic function.

Left ventricular diastolic stiffness increases with normal aging in humans. Longitudinal echocardiographic assessments reveal prominent age-related myocardial hypertrophy. Aging hearts exhibit myocyte hypertrophy, increased myocyte apoptosis, interstitial and subendocardial fibrosis, and amyloid deposition as consequences of multiple senescence-related pathways. Cardiosphere-derived cells increased telomere length, recapitulated a young gene expression pattern, decreased interstitial fibrosis and attenuated hypertrophy. Meanwhile, diastolic function improved, in association with lower levels of circulating BNP in CDC-injected rats. Telomere shortening is a biomarker of lifetime stress, and telomere attrition is responsible for accelerated aging. Moreover, telomere dysfunction is a popular target for interventions to augment the regenerative capacity of mammalian hearts, given that telomeres figure prominently in cardiomyocyte cell-cycle arrest after birth. Here, telomere length of heart cells globally, and of cardiomyocytes specifically, was greater in old animals transplanted with CDCs obtained from very young rats compared with placebo (PBS). Telomerase is activated in the neonatal mammalian heart and is required for heart regeneration in zebrafish. The Inventors found that telomerase activity was increased in old human heart progenitor cells and in senescent rat cardiomyocytes primed with young CDCs. These effects were mediated in a paracrine manner by secreted CDC-derived exosomes. Telomerase activation was associated with telomere elongation, decreased cell senescence and cardioprotection in culture. The Inventors' results indicate that telomere elongation with CDCs is not exclusive to cardiomyocytes. Although non-cardiomyocyte heart cell populations were not specifically characterized in this study, rejuvenation of any type of cell, defined by the presence of longer telomeres, will likely be beneficial from a functional point of view. Specifically, senescence of fibroblasts may contribute to diastolic dysfunction by favouring their transformation into proinflammatory myofibroblasts, with consequent adverse extracellular matrix remodelling and secretion of inflammatory cytokines.

Circulating levels of inflammatory cytokines IL-1b and IL-6 were decreased, accompanied by an increase of anti-inflammatory IL-10 levels in old CDC-treated animals. Thus, CDCs antagonize the SASP, which contributes to a spiral of increasing inflammation, dysfunction, and age-related diseases. Attenuation of SASP may underlie the FIG.

19 depiction of heart aging and proposed mechanisms whereby young CDCs exert anti-senescent effects. The process of aging is depicted in the upper row. Transplanted CDCs secrete exosomes (CDC-XO), microvesicles, or both which lead to cellular rejuvenation. In the heart, left ventricular hypertrophy (LVH) is attenuated and fibrosis is decreased, leading to improved diastolic function.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of cardiosphere-derived cells, the use of alternative sources such as cells derived directly from heart biopsies (explant-derived cells), or from self-assembling clusters of heart-derived cells (cardiospheres), extracellular vesicles such as exosomes, microvesicles, or both produced by such cells, method of isolating, characterizing or altering extracellular vesicles such as exosomes, microvesicles, or both produced by such cells, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treating age-related stiffness of a heart comprising:
    selecting a subject in need of treatment;
    administering a composition to the subject, wherein administration of the composition reduces stiffness in the heart of the subject, the composition comprising cardiosphere-derived cells (CDCs);
    wherein the CDCs are from a donor that is younger than the subject.

2. The method of claim 1, wherein the CDCs are from human pediatric subjects.

3. The method of claim 1, wherein the composition is capable of increasing telomerase (TASE) activity.

4. The method of claim 1, wherein the composition is capable of maintaining or extending telomere length in the subject.

5. The method of claim 1, wherein the composition is capable of reducing serum marker levels.

6. The method of claim 5, wherein the serum markers comprise one or more of: brain natriuretic peptide (BNP), creatinine, C-reactive protein (CRP), IL-1b, and IL-6.

7. The method of claim 1, wherein administration of the composition comprises intramyocardial or intraventricular injection.

8. A method of treating age-related hypertrophy of a heart comprising:
    selecting a subject in need of treatment;
    administering a composition to the subject, wherein administration of the composition reduces age-related hypertrophy of the heart of the subject, the composition comprising cardiosphere-derived cells (CDCs);
    wherein the CDCs, are from a donor that is younger than the subject.

9. The method of claim 8, wherein the CDCs are from human pediatric subjects.

10. The method of claim 1, wherein treatment with the composition also results in a decrease of one or more of: cardiomyopathies, atherosclerosis, coronary artery disease, and diastolic dysfunction.

11. The method of claim 1, wherein treatment with the composition also results in a decrease of one or more of: hair loss, frailty, age-related cognitive decline, age-related sexual dysfunction, and progeria.

12. The method of claim 1, wherein administration of the composition comprises delivery to a site of diseased or dysfunctional tissue.

13. The method of claim 1, wherein the composition reduces senescence associated beta-galactosidase (SA-β-GAL) expressing senescent cells of the subject.

14. The method of claim 1, wherein the composition increases expression of telomerase reverse transcriptase (TERT) in the subject.

15. The method of claim 8, wherein the composition reduces senescence associated beta-galactosidase (SA-β-GAL) expressing senescent cells of the subject.

16. The method of claim 8, wherein the composition increases expression of telomerase reverse transcriptase (TERT) in the subject.

* * * * *